United States Patent [19]
Garini et al.

[11] Patent Number: 6,066,459
[45] Date of Patent: May 23, 2000

[54] METHOD FOR SIMULTANEOUS DETECTION OF MULTIPLE FLUOROPHORES FOR IN SITU HYBRIDIZATION AND MULTICOLOR CHROMOSOME PAINTING AND BANDING

[75] Inventors: Yuval Garini, Mizpe Koranit; Dario Cabib, Timrat; Robert A. Buckwald, Ramat Yishay, all of Israel; Thomas Ried, Bethesda, Md.; Dirk G. Soenksen, Carlsbad, Calif.

[73] Assignee: Applied Spectral Imaging Ltd., Migdal, Israel

[21] Appl. No.: 09/100,104

[22] Filed: Jun. 19, 1998

Related U.S. Application Data

[63] Continuation of application No. 08/635,820, Apr. 22, 1996, Pat. No. 5,817,462, which is a continuation-in-part of application No. 08/575,191, Dec. 20, 1995, Pat. No. 5,936,731, which is a continuation-in-part of application No. 08/571,047, Dec. 12, 1995, Pat. No. 5,784,162, which is a continuation-in-part of application No. 08/392,019, Feb. 21, 1995, Pat. No. 5,539,517, which is a continuation-in-part of application No. 08/107,673, Aug. 18, 1992, abandoned.

[51] Int. Cl.[7] .............................. C12Q 1/68; C07H 21/04
[52] U.S. Cl. .......................... 435/6; 536/24.3; 536/24.31
[58] Field of Search ............................. 435/6; 536/24.3, 536/24.31

[56] References Cited

U.S. PATENT DOCUMENTS

| | | | |
|---|---|---|---|
| 4,976,542 | 12/1990 | Smith | 356/346 |
| 5,377,003 | 12/1994 | Lewis et al. | 356/300 |
| 5,539,517 | 7/1996 | Cabib et al. | 356/346 |

OTHER PUBLICATIONS

Ried et al. Simultaneous visualization of seven different DNA probes by in situ hybridization using combinatorial fluorescence and digital imaging microscopy. Proc. Natl. Acad. Sci. vol. 89 pp. 1388–1392, 1992.

Jauch et al. Reconstruction of genomic rearrangements in great apes and gibbons by chromosome painting. Proc. Natl. Acad. Sci. USA vol. 89 pp. 8611–8615, 1992.

Schrock et al. "Multicolor Spectral Karyotyping of Human Chromosomes", *Science*, 273: 494–497, 1996.

Speicher et al, "Karyotyping Human Chromosomes by Combinatorial Multi–Fluor FISH", *Nature Genetics*, vol. 12, 1996.

*Primary Examiner*—John S. Brusca
*Attorney, Agent, or Firm*—Mark M. Friedman

[57] ABSTRACT

A spectral imaging method for simultaneous detection of multiple fluorophores aimed at detecting and analyzing fluorescent in situ hybridizations employing numerous chromosome paints and/or loci specific probes each labeled with a different fluorophore or a combination of fluorophores for color karyotyping, and at multicolor chromosome banding, wherein each chromosome acquires a specifying banding pattern, which pattern is established using groups of chromosome fragments labeled with various fluorophore or combinations of fluorophores.

13 Claims, 26 Drawing Sheets

(9 of 26 Drawing Sheet(s) Filed in Color)

FIG. 10a
FIG. 10b
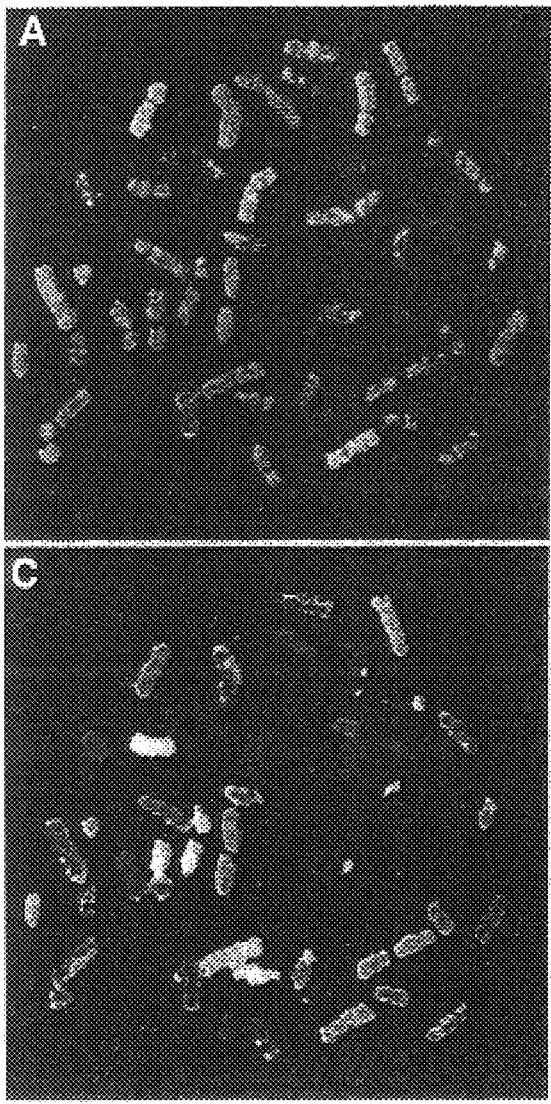
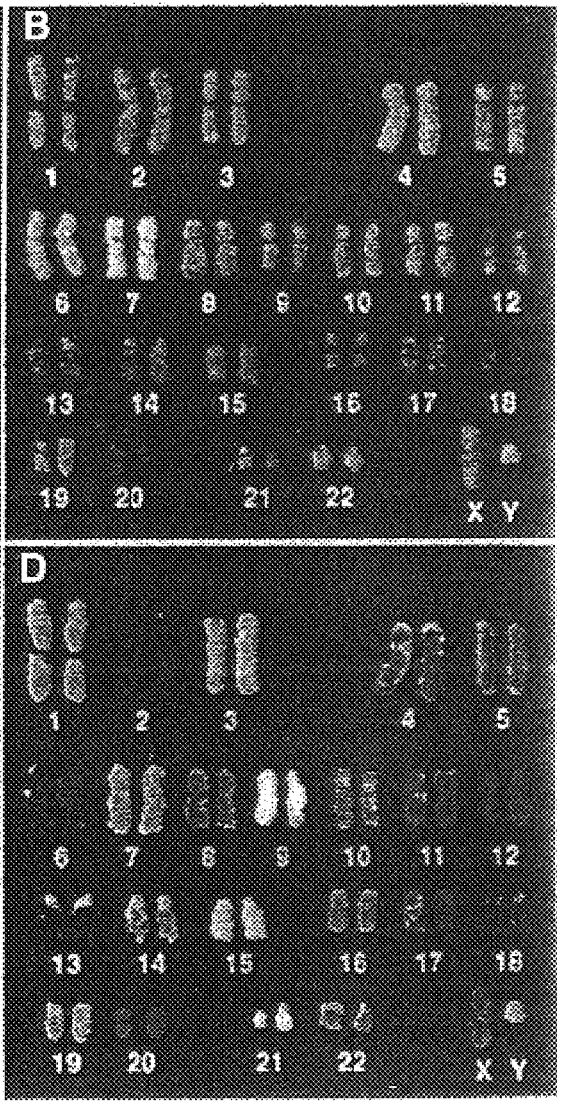
FIG. 10c
FIG. 10d
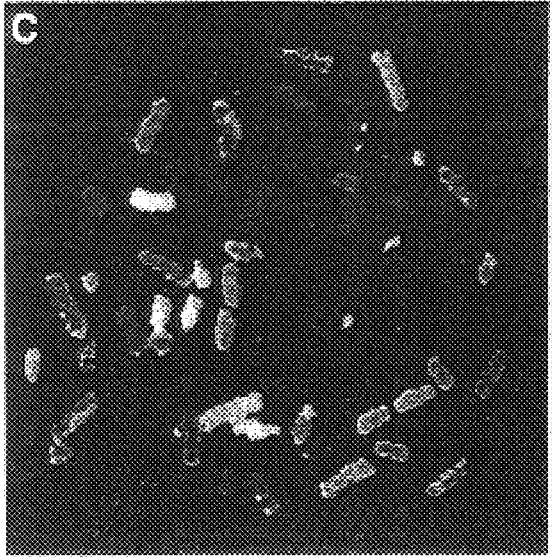
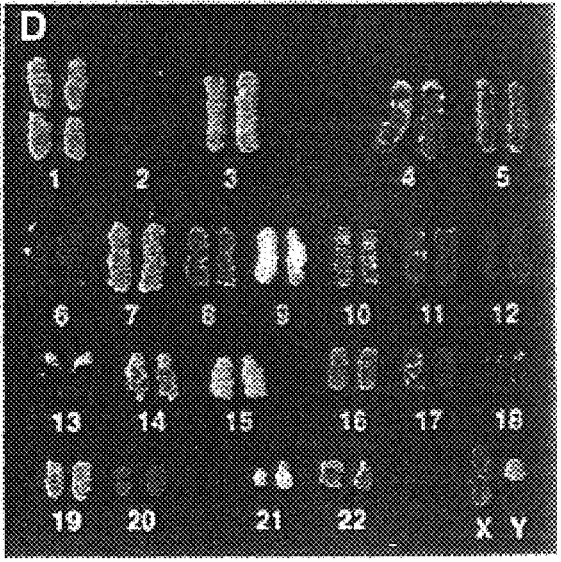

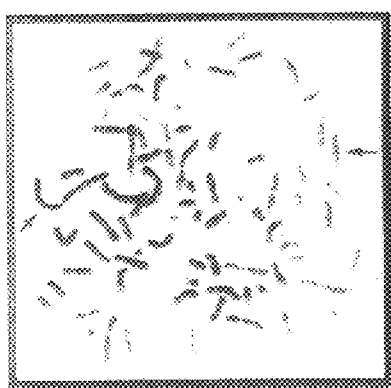 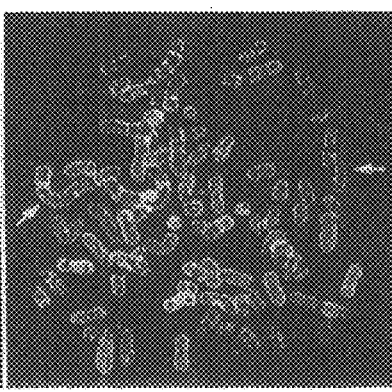 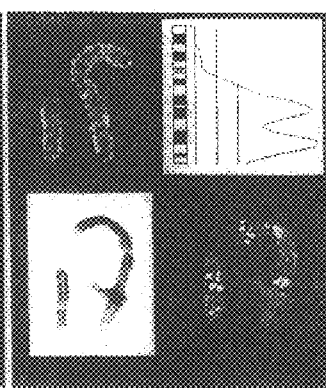

FIG. 17a
FIG. 17b
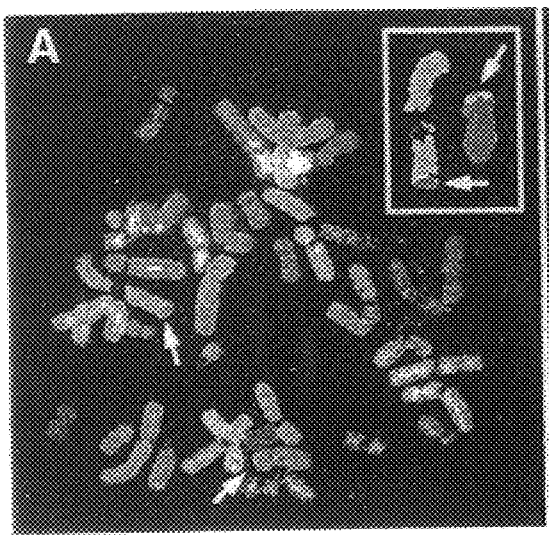
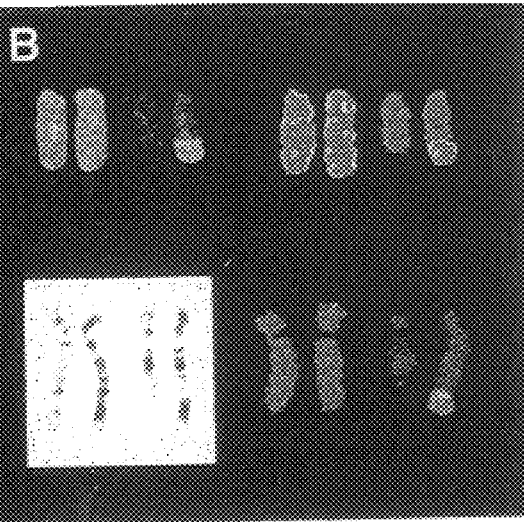

Chromosone: 5 2 10 13 16 7

SEQUENCE LISTING (1) GENERAL INFORMATION:

(iii) NUMBER OF SEQUENCES:3

(2) INFORMATION FOR SEQ ID NO:1:

(i) SEQUENCE CHARACTERISTICS:
      (A) LENGTH:22
      (B) TYPE:nucleic acid
      (C) STRANDEDNESS:single
      (D) TOPOLOGY:linear (xi) SEQUENCE DESCRIPTION: SEQ ID NO:1:

TCCCAAAGTG CTGGGATTAC AG                         22

(2) INFORMATION FOR SEQ ID NO:2:

(i) SEQUENCE CHARACTERISTICS:
      (A) LENGTH:17
      (B) TYPE:nucleic acid
      (C) STRANDEDNESS:single
      (D) TOPOLOGY:linear (xi) SEQUENCE DESCRIPTION: SEQ ID NO:2:

CTGCACTCCA GCCTGGG                             17

(2) INFORMATION FOR SEQ ID NO:3:

(i) SEQUENCE CHARACTERISTICS:
      (A) LENGTH:22

```
            (B) TYPE:nucleic acid
            (C) STRANDEDNESS:single
            (D) TOPOLOGY:linear (xi) SEQUENCE DESCRIPTION: SEQ ID NO:3:

CCGACTCGAG NNNNNNATGT GG                                                          22
```

METHOD FOR SIMULTANEOUS DETECTION OF MULTIPLE FLUOROPHORES FOR IN SITU HYBRIDIZATION AND MULTICOLOR CHROMOSOME PAINTING AND BANDING

This is a continuation of U.S. patent application Ser. No. 08/635,820, filed Apr. 22, 1996, now U.S. Pat. No. 5,817,462, issued Oct. 6, 1998, which is a continuation-in-part of U.S. patent application Ser. No. 08/575,191, filed Dec. 20, 1995, now U.S. Pat. No. 5,936,731, issued Aug. 10, 1999, which is a continuation-in-part of U.S. patent application Ser. No. 08/571,047, filed Dec. 12, 1995, now U.S. Pat. No. 5,784,162, issued Jul. 21, 1998, which is a continuation-in-part of U.S. patent application Ser. No. 08/392,019 filed Feb. 21, 1995, now U.S. Pat. No. 5,539,517, issued Jul. 23, 1996, which is a continuation-in-part of U.S. patent application Ser. No. 08/107,673, filed Aug. 18, 1992, now abandoned. The specifications of each of these applications are hereby incorporated by reference.

FIELD AND BACKGROUND OF THE INVENTION

The present invention relates in general to a method for simultaneous detection of multiple fluorophores. More particularly, the present invention relates to a spectral imaging method aimed at detecting and analyzing fluorescent in situ hybridizations employing numerous chromosome paints and/or loci specific probes each labeled with a different fluorophore or a combination of fluorophores. Further particularly, the present invention relates to a method of multicolor chromosome banding (i.e., bar-coding), wherein each chromosome acquires a specifying banding pattern, which pattern is established using groups of chromosome fragments labeled with a fluorophore or a combination of fluorophores, this method is referred to herein below also as hybridization based multicolor chromosome banding. The method of the present invention for simultaneous detection of multiple fluorophores is highly sensitive both in spatial and spectral resolutions and is capable of simultaneous detection of dozens of fluorophores and/or combinations of fluorophores, therefore, the method of the present invention can be used for the detection of fluorescently painted complete sets of chromosomes, multiple loci and/or chromosome specific multicolor banding patterns from a species such as human, and to provide a complete multicolor karyotype, wherein each chromosome is identified due to a specifying color, and a complete multicolor chromosome banding pattern, wherein each chromosome is identified according to a specifying multicolor banding pattern.

A spectrometer is an apparatus designed to accept light, to separate (disperse) it into its component wavelengths, and measure the lights spectrum, that is the intensity of the light as a function of its wavelength. An imaging spectrometer is one which collects incident light from a scene and measures the spectra of each pixel (i.e., picture element) thereof.

Spectroscopy is a well known analytical tool which has been used for decades in science and industry to characterize materials and processes based on the spectral signatures of chemical constituents. The physical basis of spectroscopy is the interaction of light with matter. Traditionally, spectroscopy is the measurement of the light intensity emitted, transmitted, scattered or reflected from a sample, as a function of wavelength, at high spectral resolution, but without any spatial information.

Spectral imaging, on the other hand, which is a combination of high resolution spectroscopy and high resolution imaging (i.e., spatial information) has yet not been used for analyzing biological samples. The closest work so far described concerns either obtaining high spatial resolution information from a biological sample yet providing only limited spectral information, for example, when high spatial resolution imaging is performed with one or several discrete band-pass filters [See, Andersson-Engels et al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

As will be described in great details below, combining spectroscopy with imaging is useful for various biological research and medical applications and is referred to hereinbelow as spectral bio-imaging. One example for the usefulness of spectral bio-imaging concerns detection of specific cellular constituents (e.g., proteins, nucleic acid sequences, etc.) after being labeled (i.e., tagged) with fluorescent probes. In this direction spectral imaging can be used to identify and map several fluorophores simultaneously in one measurement. In fact, the inherently high spectral resolution of spectral imaging according to the present invention is ideally suited for 'sorting out' fluorescent probes (or other chemical constituents) with overlapping spectra.

Conceptually, a spectral bio-imaging system consists of (1) a measurement system, and (2) an analysis software. The measurement system includes all of the optics, electronics and the manner in which the sample is illuminated (e.g., light source selection), the mode of measurement (e.g., fluorescence), as well as the calibration best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features. However, the high cost, size and configuration of remote sensing spectral imaging systems (e.g., Landsat, AVIRIS) has limited their use to air and satellite-borne applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30].

There are three basic types of spectral dispersion methods that might be considered for a spectral bio-imaging system: (i) spectral grating, (ii) spectral filters and (iii) interferometric spectroscopy. As will be described below, the latter is best suited to implement the method of the present invention, yet as will be appreciated by one ordinarily skilled in the art, grating and filters based spectral bio-imaging systems may also be found useful in some applications.

In a grating (i.e., monochromator) based systems, also known as slit-type imaging spectrometers, such as for example the DILOR system: [see, Valisa et al. (September 1995) presentation at the SPIE Conference European Medical Optics Week, BiOS Europe '95, Barcelona, Spain], only one axis of a CCD (charge coupled device) array detector (the spatial axis) provides real imagery data, while a second (spectral) axis is used for sampling the intensity of the light which is dispersed by the grating as function of wavelength.

The system also has a slit in a first focal plane, limiting the field of view at any given time to a line of pixels. Therefore, a full image can only be obtained after scanning the grating or the incoming beam in a direction parallel to the spectral axis of the CCD in a method known in the literature as line scanning. The inability to visualize the two-dimensional image before the whole measurement is completed, makes it impossible to choose, prior to making the measurement, a desired region of interest from within the field of view and/or to optimize the system focus, exposure time, etc. Grating based spectral imagers arc in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using acousto-optic tunable filters (AOTF) or liquid-crystal tunable filter (LCTF), see below. Similarly to the slit type imaging spectrometers equipped with a grating as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD.

The sensitivity advantage that interferometric spectroscopy has over the filter and grating method is known in the art as the multiplex or Fellgett advantage [see, Chamberlain (1979) The principles of interferometric spectroscopy, John Wiley and Sons, pp. 16–18 and p. 263].

Tunable filters, such as AOTFs and LCTFs have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda max=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

A method and apparatus for spectral analysis of images which have advantages in the above respects is disclosed in U.S. Pat. No. 5,539,517 to Cabib et al., filed Feb. 21, 1995, which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed. Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measuring time and/or substantially increasing the signal-to-noise ratio (i.e., sensitivity).

Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$. However, whereas in the conventional grating method the energy seen by every detector at any time is of the order of 1/n of the total, because the wavelength resolution is 1/n of the range, in a method according to the invention described in U.S. Pat. No. 5,539,517 the energy is of the order of unity, because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. Pat. No. 5,539,517, all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fiber optics for industrial monitoring and medical imaging, diagnosis, therapy and others.

In a continuation application (U.S. Pat. No. 5,784,162 to Cabib et al., filed Dec. 12, 1995, which is incorporated by reference as if fully set forth herein) the objective was to provide spectral imaging methods for biological research, medical diagnostics and therapy, which methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions. In U.S. Pat. No. 5,784,162, the use of the spectral imaging apparatus described in U.S. Pat. No. 5,539,517 for interphase fluorescent in situ hybridization of as much as six loci specific probes (each loci located on a different chromosome) was demonstrated, as well as additional biological and medical applications.

In a continuation application (U.S. Pat. No. 5,936,731, to Cabib et al., filed Dec. 20, 1995, which is incorporated by reference as if fully set forth herein) the objective was to provide a method for simultaneous detection of multiple fluorophores for detecting and analyzing fluorescent in situ hybridizations employing numerous chromosome paints and/or loci specific probes, each labeled with a different fluorophore or a combination of fluorophores. The method according to this invention is highly sensitive both in spatial and spectral resolutions and is capable of simultaneous detection of dozens of fluorophores and/or combinations of fluorophores, therefore it can be used for the detection of fluorescently painted complete sets of chromosomes and/or multiple loci from a species such as human and to provide a complete color karyotype.

Spectral bio-imaging systems are potentially useful in all applications in which subtle spectral differences exist between chemical constituents whose spatial distribution and organization within an image are of interest. The measurement can be carried out using virtually any optical system attached to the system described in U.S. Pat. Ser. No. 5,539,517, for example, a fluorescence microscope combined with administered fluorescent fluorophores or combinations of fluorophores.

Fluorescence measurements can be made with any standard filter cube (consisting of a barrier filter, excitation filter and a dichroic mirror), or any customized filter cube or combinations of filter cubes for special applications, provided the emission spectra fall within the spectral range of the system sensitivity.

One of the major benefits of the Human Genome Project (HGP) has been the isolation of a large number of nucleic acid probes for disease genes and other chromosome regions and structures. This has stimulated interest in DNA diagnostics as the number and types of tests that can be developed is dependent upon these probes. In recent years there has been particular interest in fluorescent in situ hybridization (FISH) which is the process of marking with a fluorescent moiety conjugated to a specific nucleic acid molecule complementary to an examined chromosome region (collectively referred herein as a probe), followed by visualization of the fluorescent moiety by fluorescence microscopy.

There is a clear trend for employing FISH technology in the clinic in parallel to its traditional employment in the basic research laboratory. FISH may be considered an advanced approach to cytogenetics and it is clear that the amount of information about chromosomes that may be gained from FISH far outdistances that obtained from standard karyotyping by the presently used DNA banding methods (e.g., G- and R-banding). In addition, diagnostics information may be gained much more rapidly using techniques such as interphase cytogenetics as compared to classical (metaphase) cytogenetics, since cell culturing and synchronization can be omitted.

According to the present invention provided is a FISH imaging method, capable of simultaneously acquiring fluorescence spectra from all pixels of a field of view of a fluorescence microscope and simultaneously detect the location of dozens of probes in a single measurement. In conjunction with the availability of chromosome specific probes (i.e., chromosome paints) and chromosome fragments specific probes (e.g., YAC contigs, BAC contigs and radiation hybrid cell lines), and novel labeling strategies, the method is able to create a FISH karyotype with each chromosome being painted with a different color (i.e., 24 different colors for a human male karyotype, 23 for a female) and/or a multicolor chromosome banding karyotype, wherein each chromosome acquires a multicolor specifying banding pattern, which pattern is established using chromosome fragments labeled with a fluorophore or a combination of fluorophores. This method results in extremely high sample throughput and allows analysis of an exceedingly high number of differently labeled probes.

There is thus a widely recognized need for, and it would be highly advantageous to have a spectral imaging method for detecting and analyzing fluorescent in situ hybridizations employing numerous chromosome paints, loci specific probes and chromosome fragments probes, labeled with various fluorophore or combinations of fluorophores, for the obtainment of a complete multicolor karyotype, wherein each chromosome is identified due to a specifying color, a complete multicolor chromosome banding pattern, wherein each chromosome is identified according to a specifying multicolor banding pattern, and/or simultaneous multiple loci mapping.

SUMMARY OF THE INVENTION

According to the present invention there is provided a spectral imaging method aimed at detecting and analyzing fluorescent in situ hybridizations employing numerous chromosome paints and/or loci specific probes each labeled with a different fluorophore or a combination of fluorophores, and at multicolor chromosome banding (i.e., bar-coding), wherein each chromosome acquires a specifying banding pattern, which pattern is established using groups of chromosome fragments labeled with a fluorophore or a combination of fluorophores.

According to further features in preferred embodiments of the invention described below, the method comprising the steps of (a) for multicolor chromosome painting, providing a cell nucleus having chromosomes, the chromosomes being hybridized with at least one nucleic acid probe being labeled with at least one fluorophore, or (a') for multicolor chromosome banding, providing a cell nucleus of a first species having a genome and chromosomes, the chromosomes being hybridized with at least one group of chromosome fragments covering at least a fraction of the genome of the first species, each of the groups of fragments being labeled with at least one fluorophore; (b) viewing the cell nucleus through a fluorescence microscope, the fluorescence microscope being optically connected to an imaging spectrometer, the fluorescence microscope and the imaging spectrometer being for obtaining a spectrum of each pixel of the cell, wherein the obtainment of the spectrum of each pixel of the cell nucleus is by (i) collecting incident light simultaneously from all pixels of the cell nucleus using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the cell nucleus for the entire duration of the measurement, so that the real image of the cell nucleus is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating or translating one or more of the elements of the interferometer system, so that the optical path difference between the two coherent beams generated by the interferometer system is scanned simultaneously for all the pixels of the cell nucleus; and (v) recording signals of each of the detector elements as function of time using a recording device to form a first spectral cube of data; and (c) interpreting the first spectral cube of data using a mathematical algorithm.

According to still further features in the described preferred embodiments the fluorescence microscope is supplemented with a filter selected from the group consisting of a double dichroic band filter and a triple dichroic band filter.

According to still further features in the described preferred embodiments the at least one nucleic acid probe is selected from the group consisting of at least one locus, at least one fragmented chromosome, at least one yeast artificial chromosome including an insert, at least one plasmid including an insert, at least one cosmid including an insert, at least one phagemid including an insert, at least one viral vector including an insert, a complete genome of a species, a complete genome of a cancerous tissue and combinations thereof.

According to still further features in the described preferred embodiments labeling of nucleic acid probes and chromosomes fragments is by combinatorial labeling or hybridization strategies.

According to still further features in the described preferred embodiments the method is used for comparative genome hybridization.

According to still further features in the described preferred embodiments the cell nucleus is selected from the group consisting of a cell nucleus during interphase, a cell nucleus during mitosis and a cell nucleus during meiosis.

According to still further features in the described preferred embodiments the number of nucleic acid probes is selected from the group of numbers consisting of one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four and higher than twenty four, each of the probes includes a different fluorophore or a different combination of the fluorophores.

According to still further features in the described preferred embodiments the chromosomes are selected from the group consisting of interphase chromosomes, chromosomes during mitosis and chromosomes during meiosis.

According to still further features in the described preferred embodiments the mathematical algorithm is a point operation analysis of the spectrum of each of the pixels in the cell nucleus.

According to still further features in the described preferred embodiments the point operation analysis includes mapping the spectrum of each of the pixels in the cell nucleus into a scalar according to a transformation function.

According to still further features in the described preferred embodiments the point operation analysis includes mapping the spectrum of each of the pixels of the cell nucleus into another spectrum according to a transformation function.

According to still further features in the described preferred embodiments the mathematical algorithm is a morphological analysis, the morphological analysis determines the relative size of the chromosomes in the cell nucleus.

According to still further features in the described preferred embodiments the mathematical algorithm is a classification mapping analysis computing for the spectrum of each of the pixels a spectral difference from at least one reference spectrum.

According to still further features in the described preferred embodiments the classification mapping analysis results in generating a multicolor image, in which groups of pixels having a predetermined maximal spectral differences from one of the several reference spectra are colored with a predetermined artificial color.

According to still further features in the described preferred embodiments the spectral difference is a scalar defined as the integral over a predefined wavelength range of the absolute value of the difference between the spectrum of each of the pixels and one of the several reference spectra.

According to still further features in the described preferred embodiments the mathematical algorithm is a principal component analysis.

According to still further features in the described preferred embodiments the principal component analysis includes (a) building a covariant matrix for all of the pixels and the wavelengths of the measurement, including wavelengths of exciting sources when multiple wavelengths are used; (b) diagonalizing the covariant matrix and finding all independent orthogonal spectral base elements; and (c) finding which of the base elements or a combination thereof tag certain features in the cell nucleus.

According to still further features in the described preferred embodiments the mathematical algorithm is a linear combination analysis.

According to still further features in the described preferred embodiments the linear combination analysis is for spectral normalization.

According to still further features in the described preferred embodiments the linear combination analysis includes applying a given scalar to every wavelength of the spectra of each of the pixels by an arithmetical function, the function is selected from the group consisting of addition, subtraction, multiplication, division and combinations thereof.

According to still further features in the described preferred embodiments the linear combination analysis is for background subtraction in which a spectrum of a pixel located in a background region of the cell nucleus is subtracted from the spectra of the pixels of the cell nucleus.

According to still further features in the described preferred embodiments the linear combination analysis is for a calibration procedure in which a spectrum measured prior to viewing the cell nucleus is for dividing the spectra of the pixels of the cell nucleus.

According to still further features in the described preferred embodiments the mathematical algorithm computes a Red-Green-Blue color image using predefined wavelength ranges.

According to still further features in the described preferred embodiments the Red-Green-Blue color image is modified by a contrast stretching algorithm.

According to still further features in the described preferred embodiments the mathematical algorithm computes a ratio between intensities at two different wavelengths for each of the spectra of the pixels.

According to still further features in the described preferred embodiments the mathematical algorithm computes a ratio between intensities at two different wavelengths for each of the spectra of the pixels and paints each of the pixels in a lighter or darker artificial color, according to the computed ratio.

According to still further features in the described preferred embodiments the method is for an application selected from the group consisting of providing a color karyotype of embryonic cells, providing a color karyotype of white blood cells, providing a color karyotype of malignant cells and providing a color karyotype of cells examined for malignancy.

According to still further features in the described preferred embodiments providing the color karyotype of the cells examined for malignancy is for obtaining a color translocation map.

According to still further features in the described preferred embodiments providing the color karyotype of the malignant cells is for obtaining a color translocation map.

According to still further features in the described preferred embodiments the chromosomes are further stained with a conventional chromosome banding dye, the method further comprising obtaining a gray level banding image of the chromosomes.

According to still further features in the described preferred embodiments the conventional chromosome banding dye is DAPI.

According to still further features in the described preferred embodiments the chromosome fragments are from a source selected from the group consisting of radiation hybrid cell lines, YAC-clones, BAC-clones, size separated endonuclease digestion products of the genome of the species and microdissected chromosome fragments.

According to still further features in the described preferred embodiments the labeling of the fragments is by interspersed repetitive sequence—PCR.

According to still further features in the described preferred embodiments the interspersed repetitive sequence is Alu.

According to still further features in the described preferred embodiments the fluorophores are conjugated to a nucleotide or a nucleotide analog.

According to still further features in the described preferred embodiments the fraction is selected from the group consisting of 10–20%, 21–30%, 31–40%, 41–50%, 51–60%, 61–70%, 71–80%, 81–90% and 91–100%.

According to still further features in the described preferred embodiments the first species is selected from the group consisting of human and mouse.

According to still further features in the described preferred embodiments the chromosome fragments are of a second species.

According to still further features in the described preferred embodiments the chromosome fragments are grouped into groups, each of the groups is labeled with a different fluorophore or combination of fluorophores.

According to still further features in the described preferred embodiments the method is for an application selected from the group consisting of providing a color banding karyotype of embryonic cells, providing a color banding karyotype of white blood cells, providing a color banding karyotype of malignant cells and providing a color banding karyotype of cells examined for malignancy.

According to still further features in the described preferred embodiments the embryonic cells are selected from the group consisting of chorionic villi cells and embryonic cells isolated from a pregnant woman peripheral blood.

According to still further features in the described preferred embodiments the method is for detecting a trisomy of a genetic material selected from the group consisting of human chromosome 21, human chromosomal band 21q22, a fragment of human chromosomal band 21q22, human chromosome 18, a fragment of human chromosome 18, human chromosome 13 and a fragment of human chromosome 13.

According to still further features in the described preferred embodiments providing the color banding karyotype of the cells examined for malignancy, is for obtaining a color translocation map.

According to still further features in the described preferred embodiments providing the color banding karyotype of the malignant cells is for obtaining a color translocation map.

According to still further features in the described preferred embodiments the method is for detecting chromosomal aberrations.

According to still further features in the described preferred embodiments the chromosomal aberrations are selected from the group consisting of deletions, inversions, translocations and amplifications.

According to still further features in the described preferred embodiments the method is for detecting chromosomal aberrations selected from the group consisting of recurrent chromosomal aberrations and secondary chromosomal aberrations.

According to still further features in the described preferred embodiments the method is for detecting the stage of a malignancy.

According to still further features in the described preferred embodiments the detection of the stage of the malignancy is for selecting a treatment for the malignancy.

According to still further features in the described preferred embodiments the method is for following the efficiency of an anti-cancer treatment.

According to still further features in the described preferred embodiments the method is for detecting chromosomal aberrations following exposure to mitogenic agents.

The present invention successfully addresses the shortcomings of the presently known configurations by providing a method for in situ hybridization which is sensitive enough to simultaneously detect dozens of spectrally similar, yet some what different fluorescent probes, thus, the method of the present invention is capable of providing a color karyotype in which each chromosome pair appears in a different RGB or artificial color; simultaneous loci mapping of dozens of loci; a combination of color karyotyping and multiple loci mapping and multicolor chromosome banding.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention herein described, by way of example only, with reference to the accompanying drawings, wherein:

FIGS. 10a, 10b, 10c and 10d are (a) an RGB image, (b) a color karyotype derived from it, (c) a classification mapping of the image under a, and (d) a color karyotype derived from c, respectively, of the 24 human male chromosomes (1–22, X and Y) each of the chromosomes was painted using a different chromosome paint as detailed in Tables 3 and 4 below, obtained using the method of the present invention, all images are presented in black and white.

FIGS. 12a, 12b, 12c, 12d and 12e are (a) a DAPI R-banding photograph of a first chromosome spread of breast cancer cell line SKBR3 obtained with a conventional fluorescence microscope, (b) an RGB color karyotype of the first spread obtained using the chromosome paints as in FIGS. 9a–b and the method of the present invention (presented in black and white), (c) a DAPI R-banding photograph obtained with the SpecraCube™ system of a second chromosome spread, (d) an RGB color karyotype of the first spread obtained using the chromosome paints as in FIGS. 9a–b and the method of the present invention (presented in black and white) and (e) an RGB color comparative genomic hybridization (CGH) of two marker chromosomes of the SKBR3 cell line marked with arrows in FIG. 12c and 12d, using DNA extracted from the cell line (upper part of e) and a dual-color FISH analysis with a chromosome painting probe for chromosome 8 (in blue) and a cosmid probe for the c-myc oncogene (in red) (lower part of e).

FIGS. 17a and 17b are color presentations of FIGS. 16a–b, respectively;

DESCRIPTION OF THE PREFERRED EMBODIMENTS

The present invention is of a spectral imaging method for detecting and analyzing fluorescent in situ hybridizations employing numerous chromosome paints, chromosome fragments and loci specific probes labeled with different fluorophore or a combination of fluorophores, the method is highly sensitive both in spatial and spectral resolutions and is capable of simultaneous detection of dozens of fluorophores or combinations of fluorophores. Therefore, the method of the present invention can be used for detection of fluorescently painted complete sets of chromosomes, multiple loci and/or chromosome specific multicolor banding (i.e., bar-coding) patterns from a species such as human, and to provide a complete multicolor karyotype, wherein each chromosome is identified due to a specifying color and a complete multicolor chromosome banding pattern, wherein each chromosome is identified according to a specifying multicolor banding pattern.

Figure 1:
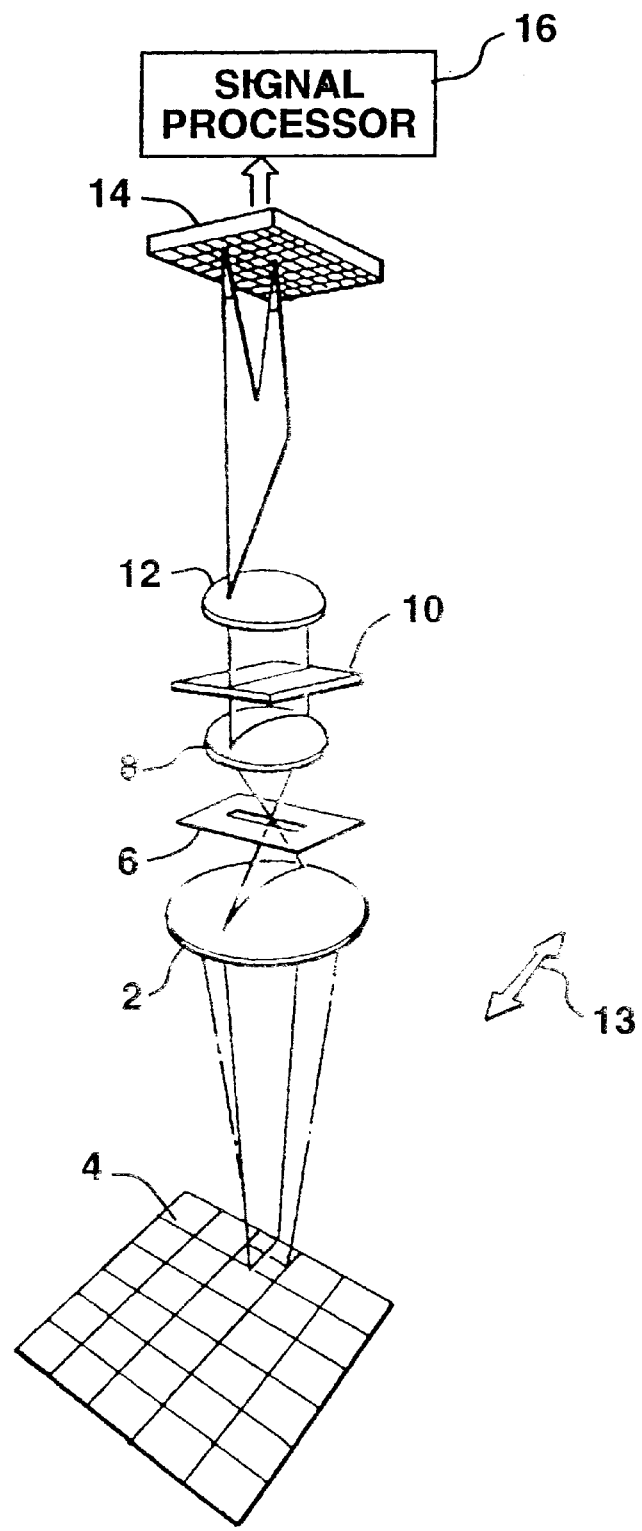
FIG. 1 illustrates a conventional (prior art) slit-type imaging spectrometer.

For purposes of better understanding the present invention, as illustrated in FIGS. 4–23 of the drawings, reference is first made to the construction and operation of a conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system as indicated at 2, for collecting the incident light from a scene, schematically indicated at 4 and focusing the substantially parallel light of the scene 4 onto a first focal plane occupied by a slit 6 to define the field of view. The light exiting from slit 6 is collimated in a collimator lens 8 and is passed through a spectral dispersion element 10 (e.g., a grating) to separate the various wavelengths. The output from spectral dispersion element 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., a raster movement or line scanning indicated by arrow 13) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time. This is necessary to separate the spectra of each pixel.

As mentioned in the background section and hereinabove, the disadvantage of the prior art method illustrated in FIG. 1 is that most of the pixels of one frame are not measured at any given time even though the optical system 2 actually collects energy from all of them simultaneously. As a result, the required frame time is significantly increased, and/or the signal-to-noise ratio (sensitivity) is substantially decreased with respect to a system which does not have the need for such a slit. Yet, as will be appreciated by one ordinarily skilled in the art, prior art slit-type imaging spectrometers such as for example the one shown in FIG. 1, and prior art filters based imaging spectrometers (not shown) may also be found useful for some applications of the method of the present invention as described hereinbelow.

Figure 2:
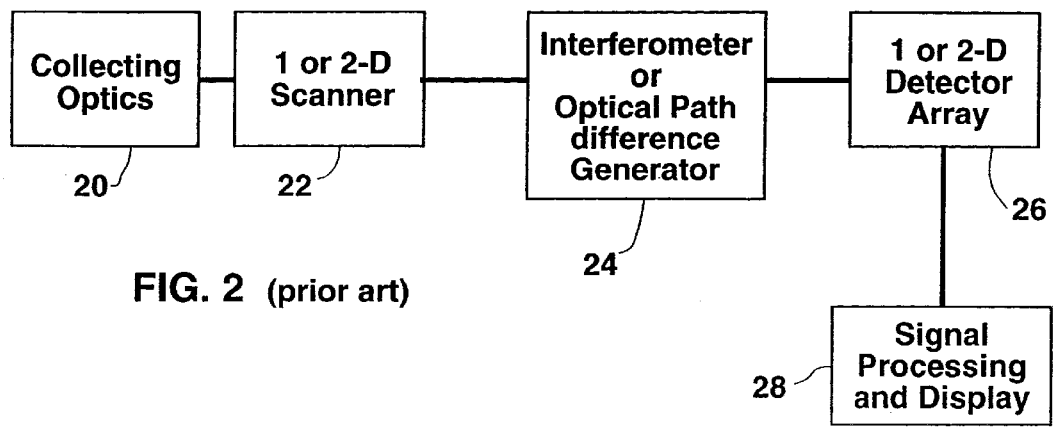
FIG. 2 is a block diagram illustrating the main components of an imaging spectrometer constructed in accordance with U.S. patent application Ser. No. 08/392,019 (prior art)

FIG. 2 is a block diagram illustrating the main components of an improved prior art imaging spectrometer disclosed in U.S. Pat. No. 5,539,517 to Cabib et al., filed Feb. 21st, 1995 which is incorporated by reference as if fully set forth herein. This imaging spectrometer is constructed highly suitable to implement the method of the present invention.

Thus, the prior art imaging spectrometer of FIG. 2 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, such as the four-mirror plus beamsplitter interferometer as further described in the cited U.S. Pat. application (see FIG. 14 there).

Figure 3:
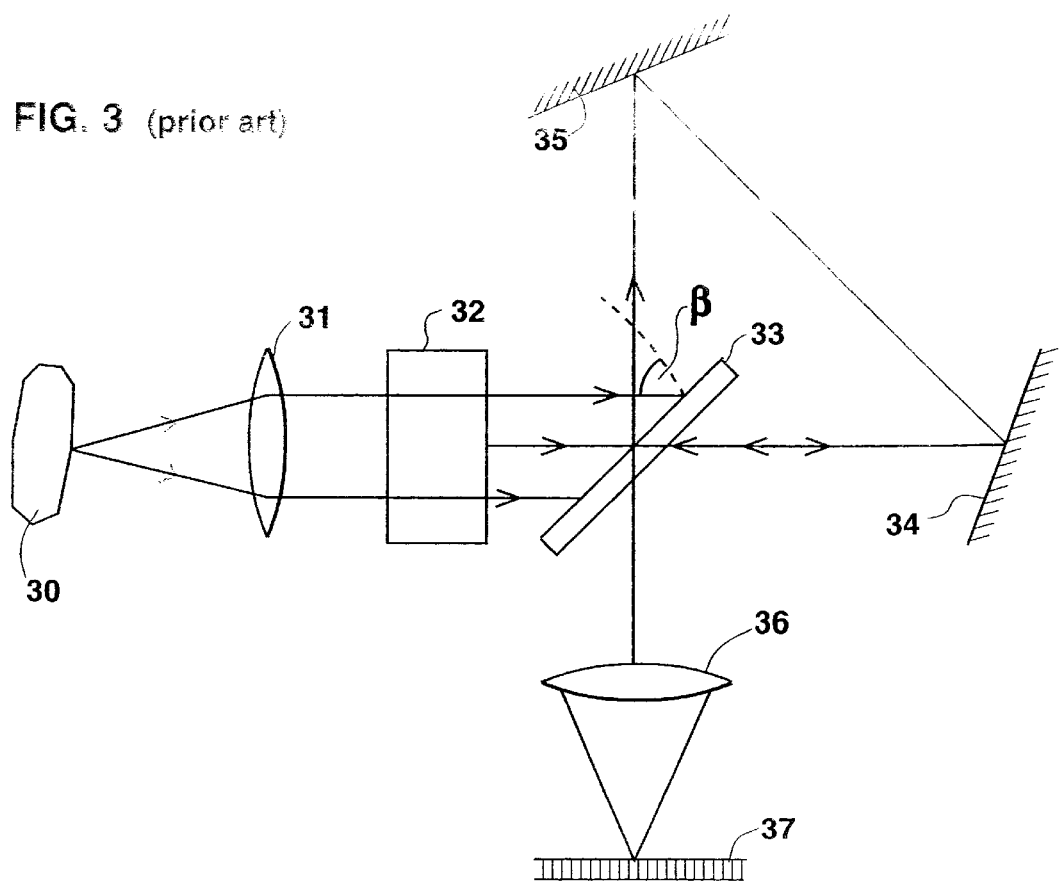
FIG. 3 illustrates a non-moving type interferometer, namely, a Sagnac interferometer, as used in an imaging spectrometer in accordance with U.S. patent application Ser. No. 08/392,019 (prior art)

FIG. 3 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 3, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle (θ) to the optical axis undergoes an OPD which is a function of the thickness of the beamsplitter 33, its index of refraction, and the angle θ. The OPD is proportional to θ for small angles. By applying the appropriate inversion, and by careful bookkeeping, the spectrum of every pixel is calculated.

In the configuration of FIG. 3 the ray which is incident on the beamsplitter at an angle β (β=45° in FIG. 3) goes through the interferometer with an OPD=0, whereas a ray which is incident at a general angle β−θ undergoes an OPD given by the following:

$$OPD(\beta,\theta,t,n)=t[(n^2-\sin^2(\beta+\theta))^{0.5}-(n^2-\sin^2(\beta-\theta))^{0.5}+2\sin\beta\sin\theta]\quad(1)$$

where β is the angle of incidence of the ray on the beamsplitter; θ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

An imaging spectrometer in accordance with the invention disclosed in U.S. Pat. No. 5,539,517 was developed by Applied Spectral Imaging Ltd., Industrial Park, Migdal Haemek, Israel and will be referred hereinbelow as SpectraCube™. The SpectraCube™ system optically connected to a variety of optical devices was used to implement the method of the present invention. The SpectraCube™ system has the following characteristics, listed hereinbelow in Table 1:

TABLE 1

| Character | Performance |
| --- | --- |
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

DISPLAY AND ANALYSIS OF SPECTRAL IMAGES a. General

As mentioned above, a spectral image is a three dimensional array of data, I(x,y,λ), that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set i.e., a spectral cube.

One possible type of analysis of a spectral cube is to use spectral and spatial data separately, i.e., to apply spectral algorithms to the spectral data and two-dimensional image processing algorithms to the spatial data.

As an example of a spectral algorithm, consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., I(x,y,λ)), is visualizing that data structure in a meaningful way. Unlike other types of 3D data such as tomographic data, D(x,y,z), obtained for example by a confocal microscope, where each point represents, in general, the intensity at a different location (x,y,z) in a tree-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x, y) = \int_{\lambda_1}^{\lambda_2} w(\lambda) \cdot I(x, y, \lambda) d\lambda \qquad (2)$$

Figure 4:
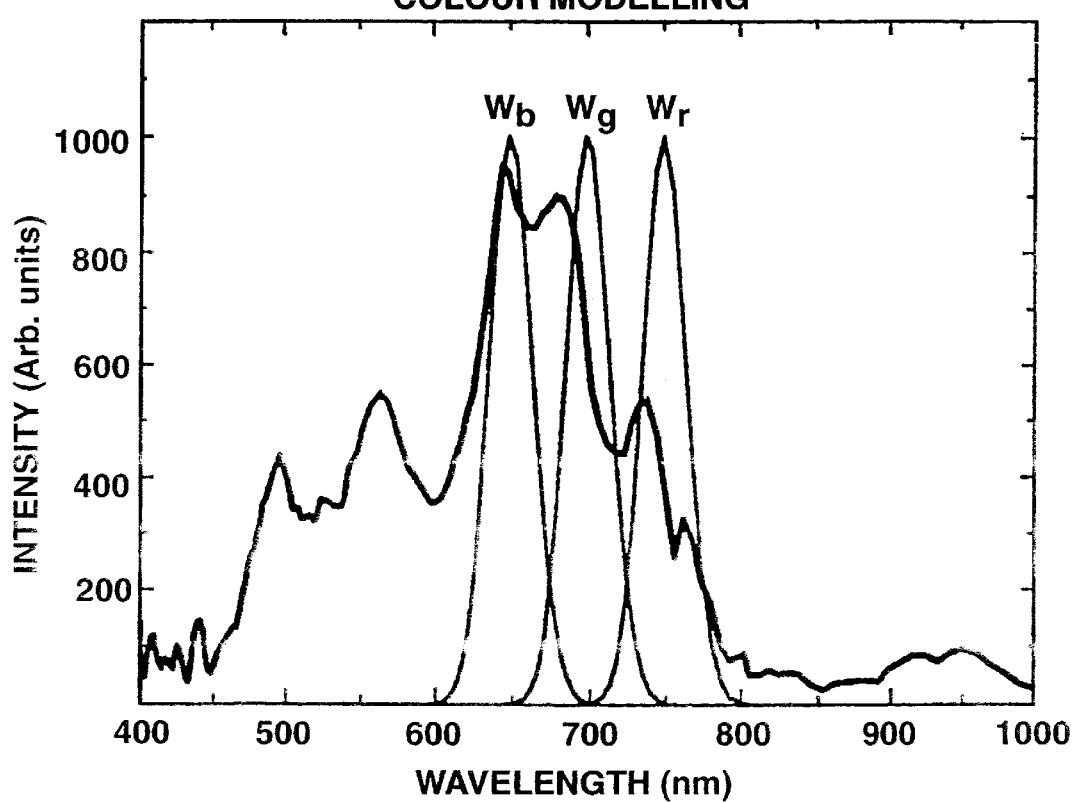
FIG. 4 shows a definition of pseudo-RGB (Red, Green and Blue) colors for emphasizing chosen spectral ranges. The intensity for each pseudo-color is calculated by integrating the area under the curve, after multiplying it by one of the curves.
Figure 5:
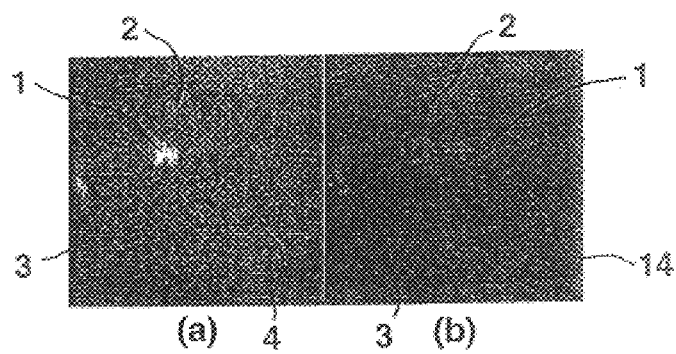
FIGS. 5a, 5b and 5c show interphase FISH performed with two different probes attached to Texas-Red and Rhodamine wherein (a) is an original image, the way it looks thorough a microscope; (b) is the same sample, after being measured and processed by the method of the present invention; and (c) are the fluorescence spectra of the Texas-Red and Rhodamine fluorophores.
Figure 5:
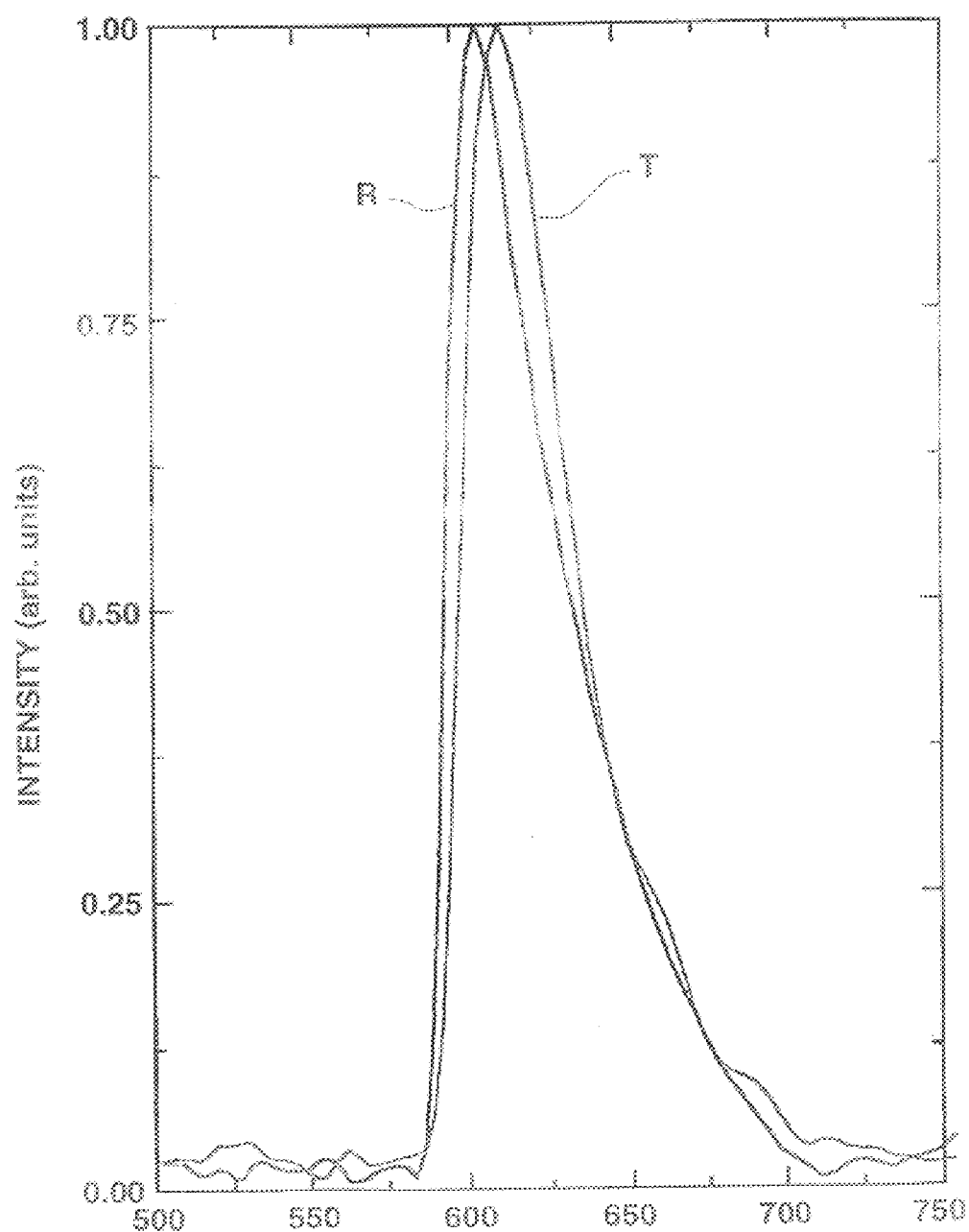

In equation 2, $w(\lambda)$ is a general weighting response function that provides maximum flexibility in computing a variety of gray scale images, all based on the integration of an appropriately weighted spectral image over some spectral range. For example, by evaluating equation 2 with three different weighting functions, $\{w_r(\lambda), w_g(\lambda), w_b(\lambda)\}$, corresponding to the tristimulus response functions for red (R), green (G) and blue (B), respectively, it is possible to display a conventional RGB color image. It is also possible to display meaningful non-conventional (pseudo) color images. FIG. 4 presents an example of the power of this simple algorithm. Consider choosing $\{w_r, w_g, w_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point Operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant. Additional examples include similarity and classification mapping as described hereinabove.

The concept of point operations can also be extended to spectral images: here each pixel has its own intensity function (spectrum), i.e., an n-dimensional vector $V_1(\lambda)$; $\lambda \in [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \in [\lambda_1, \lambda_n] \qquad (3)$$

Building a gray scale image according to Equation 3 is an example of this type of point operation. In the more general case, a point operation maps the spectrum (vector) of each pixel into another vector according to a transformation function:

$$V_2(l) = g(V_1(\lambda)); l \in [1, N], \lambda \in [\lambda_1, \lambda_n] \qquad (4),$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10} \frac{I(\lambda)}{I_0(\lambda)} = -\log_{10} \tau(\lambda) \qquad (5)$$

where $OD(\lambda)$ is the optical density as a function of wavelength, $I(\lambda)$ is the measured spectrum, $I_o(\lambda)$ is a measured reference spectrum, and $\tau(\lambda)$ is the spectral transmitance of the sample. Equation 5 is calculated for every pixel for every wavelength where $I_o(\lambda)$ is selected from (1) a pixel in the same spectral cube for which OD is calculated; (2) a corresponding pixel in a second cube; and (3) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known.

Additional examples include various linear combination analyses, such as for example: (1) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (2) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

c. Spatial-spectral Combined Operations

In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (1) classify each pixel in the image as belonging to one of k+1 classes (k cell types plus a background) according to its spectrum; (2) segment the image into the various cell types and count the number of cells from each type; and (3) sum the fluorescence energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; i=1, 2. . . . , k, $\lambda\epsilon[\lambda_1, \lambda_n]$, and the measured spectrum at each pixel (x, y) is $s_{x,y}(\lambda)$, $\lambda\epsilon[\lambda_1, \lambda_n]$, then the following algorithm is a possible method of classification (step 1 above):

Let $e^2_i$, be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2 \qquad (6)$$

where $R_\lambda$ is the spectral region of interest. Each point [pixel (x, y)] in the image can then be classified into one of the k+1 classes using the following criterion:

point(x,y) ∈ class k+1 if $e^2_i$>threshold for all i∈[1,k], whereas point(x,y) ∈ class ρ if $e^2_i$<threshold, and ρ is such that min[$e^2_i$]= $e^2_\rho$ (7)

Steps 2 and 3 above (image segmentation and calculation of average fluorescence intensity) are now straight-forward using standard computer vision operations on the synthetic image created in accordance with the algorithm described in equations 6 and 7.

Another approach is to express the measured spectrum $s_{x,y}(\lambda)$ at each pixel as a linear combination of the k known fluorescence spectra $s_i(\lambda)$; i=1, 2, . . . , k. In this case one would find the coefficient vector C=[$c_1$, $c_2$, . . . , $c_k$] that solves:

$$F = \min \sum_{\lambda \in R_\lambda} (s(\lambda) - \hat{s}(\lambda))^2 \qquad (8)$$

where $$\hat{s}(\lambda) = \sum_{i=1}^{k} c_i \cdot s_i(\lambda),$$

Solving for $$\frac{dF}{dc_i} = 0;$$

for i=1,2, . . . , k (i.e., find values of $c_i$ which minimize F) yields the matrix equation C=$A^{-1}B$ (9), where A is a square matrix of dimension k with elements $$a_{m,n} = \left[\sum_{\lambda \in R_\lambda} s_m(\lambda) \cdot s_n(\lambda)\right], \qquad (10)$$

and B is a vector defined as $$b_m = \left[\sum_{\lambda \in R_\lambda} s_m(\lambda) \cdot s(\lambda)\right], \quad m,n = 1, 2, \ldots, k. \qquad (11)$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases objects (e.g., cells) present in a spectral image differ from one another in chemical constituents and/or structure to some degree. Using a principal component analysis by producing covariance or correlation matrix enhances these small differences. A brief description of the principal component analysis using a covariance matrix is given below. For further details regarding the principal component analysis, the reader is referred to Gartens and Naes (1989) Multivariate Calibration, John Wiley & Sons, Great Britain; and to Esbensen et al., Eds. (1994) Multi variance analysis—in practice. Computer-aided modeling as CAMO, and the Unscrambler's User's guide, Trondheim, Norway.

Thus, the intensities of the pixels of the image at wavelength $\lambda_i$ (i=1, . . . N) are now considered a vector whose length is equal to the number of pixels q. Since there are N of these vectors, one for every wavelength of the measurement, these vectors can be arranged in a matrix B' with q rows, and N columns:

$$B' = \text{No. of pixels} \begin{pmatrix} \overset{\text{No. of wavelengths}}{B'_{11} \cdots B'_{1N}} \\ \vdots \qquad \vdots \\ B'_{q1} \cdots B'_{qN} \end{pmatrix} \quad (12)$$

For each of the columns of matrix B' defined is an average:

$$M_i = \frac{1}{q}\sum_{i=1}^{q} B'_{ji}; \ i = 1 \ldots N \quad (13)$$

and a second normalized matrix B defined as:

$$B = \text{No. of pixels} \begin{pmatrix} \overset{\text{No. of wavelengths}}{B'_{11}/M_1 \cdots B'_{1N}/M_N} \\ \vdots \qquad \vdots \\ B'_{q1}/M_1 \cdots B'_{qN}/M_N \end{pmatrix} \quad (14)$$

A covariance matrix C is defined for the matrix B: $C = B^T \cdot B$ of dimensions N×N. C is diagonalized, and eigenvectors and eigenvalues related by: $C \cdot V_i = \mu_i \cdot V_i$ where Vi are N orthogonal unit vectors and $\mu_i$ are the eigenvalues representing the variance in the direction of the i-th unit vector $V_i$. In general, the lowest components represent the highest variability as a function of pixels.

The products $BV_i$ (i=1, . . . N) are the projections of the spectral image onto the elements of the orthogonal basis, They are vectors with q elements (q=number of pixels), and can be displayed separately as black and white images. These images may reveal features not obvious from a regular black and white image filtered at a certain wavelength or wavelength range.

FLUORESCENCE MICROSCOPY a. General

The use of multiple dyes (i.e., fluorophores) [see, Jain (1989) Fundamentals of Digital Image Processing, Prentice-Hall International], is one of the most powerful and common tools for analyzing tissues and cells. Fluorescence microscopy is therefore one of the most important experimental methods used in light microscopy [Lakowicz (1983) Principles of fluorescence spectroscopy, Plenum Press, New York, London]. The power of fluorescent probes is mainly due to the great variety of biological structures to which specific dyes can be bound [Waggoner (1986) Applications of fluorescence in the biomedical sciences, Eds. Taylor et al., New York: Alan R. Liss, Inc. pp. 3–28]. For a detailed review of fluorescent probes see, Mason (editor) (1993) Fluorescent and Luminescent Probes for Biological Activity, Biological Techniques Series, edited by Sattelle, Academic Press Limited, London; and, Ploem and Tanke (1987) Introduction to Fluorescence Microscopy, Oxford University Press, Royal Microscopical Society.

The rapid development of new and more sophisticated multicolor fluorescent dye molecules will continue to create a need for more advanced fluorescence imaging techniques that can utilize the full potential of these dyes. For a discussion of the revolutionary impact fluorescent dyes have had, and will continue to have, on the way research is conducted today, refer to Taylor et al. (1992) The New Vision of Light Microscopy, American Scientist, Vol. 80, pp. 322–335.

A remarked improvement in multicolor fluorescent dyes is the introduction of combinatorial fluorescent strategies (e.g., combinatorial labeling and combinatorial hybridization) which employ various combinations of few basic fluorescent dyes (i.e., fluorophores). For combinatorial labeling see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein. For combinatorial hybridization see du-Manoir et al. (1993) Detection of complete and partial chromosome gains and losses by comparative genomic in situ hybridization. Hum. Genet. 90, 590–610, which is incorporated by reference as if fully set forth herein.

Spectral bio-imaging using the method of the present invention, provides several important advantages for fluorescence imaging applications over simple filter and grating based approaches. These advantages include the following: (1) measurement of the complete spectrum, providing much more quantitative insight into the actual behavior of dye molecules in the sample of interest; (2) ability to overcome many of the traditional problems arising from undesirable background luminescence; (3) undesirable or unpredictable spectral shifts that occur in the emission spectrum of a fluorescent probe, due to its micro-environment (e.g., temperature), can be taken into account in determining the probe concentration, whereas when the fluorescence intensity is only measured with for example a band-pass filter, such spectral shifts would not only go undetected but might cause significant errors in analyzing the probe concentration; and, (4) simplification of fluorescence image acquisition and, as will be shown below in detail, when used in conjunction with the appropriate spectral analysis algorithms it is possible to separate and map, in a single measurement, many spectrally overlapping fluorescent dyes. In fact, by applying sophisticated data analysis algorithms such as multivariate analysis, principal component regression and other classification algorithms [see, Martens and Naes (1989) Multivariate Calibration, John Wiley & Sons, Great Britain] it is possible to analyze many spectrally related parameters simultaneously.

Spectral bio-imaging according to the present invention provides means for eliminating problems associated with undesirable background luminescence as follows. Fluorescence imaging microscopy is typically performed by using a fluorescence filter cube which ensures that the sample is excited by the desired short wavelengths, and that only wavelengths in a limited spectral band corresponding to the fluorescence emission of the probe reach the detector (e.g., eye, camera, etc.) [Mason (editor) (1993) Fluorescent and Luminescent Probes for Biological Activity, Biological Techniques Series, edited by Sattelle, Academic Press Limited, London]. Since fluorescence intensities are usually several orders of magnitude below the intensity of the excitation source, such background luminescence can never be eliminated perfectly [Benson et al. (1985) Cell Biol. 100, pp. 1309–1323]. The three primary sources for undesirable background luminescence are: (1) radiation from the excitation source that is not completely blocked by the dichroic mirror coating and/or the filter; (2) auto-fluorescence of the sample, and sometimes also from the optical elements; and (3) selection of an inappropriate (or sub-optimal) combination of excitation filter, dichroic mirror and barrier filters. These sources can contribute significantly to the background fluorescence. The effects of sample auto-fluorescence can usually be reduced by selecting fluorescent probes whose absorption and emission bands do not overlap with those of the sample being measured. Similarly, by choosing optical elements that are appropriately coated to reduce auto-fluorescence, the effects of this type of auto-fluorescence can also be minimized.

In spite of the best filtering methods available, undesirable background luminescence makes it often difficult, and sometimes impossible, to bring out the relevant fluorescence signal from its background (noise). The spectral bio-imaging method of the present invention is able, on the other hand, to use spectral differences between (i) the spectral shape and spectral range of the fluorescent dye and (ii) the spectral shape and spectral range of the background luminescence (including auto-fluorescence), to eliminate the effects of undesirable background luminescence.

Thus, by applying the appropriate spectral image analysis methods to the emission spectra of fluorescent probes, it is possible to improve the signal-to-noise ratio, and hence the accuracy, of fluorescence imaging measurements. This advantage of the spectral bio-imaging approach is of particular importance for ratio imaging, when quantitation of the results is desired. In addition, the spectral bio-imaging system of the present invention can save time and effort that is otherwise spent in choosing the optimal filters for a filter based measurement.

The acquisition of multicolor fluorescence images can be greatly simplified when the power of spectral bio-imaging according to the method of the present invention, is combined with the appropriate fluorescent markers. In order to fully realize the benefits afforded by spectral bio-imaging, the reader is asked to consider the typical steps involved in using a filter based imaging method to measure the fluorescence from a sample containing multiple probes. First, probes with sufficiently different absorption and emission spectra must be selected. In today's practice, this requirement limits the number of fluorescent markers in a specimen to between three and five probes. Fluorescence images are then acquired, one image for each dye, by appropriately rotating two filter wheels, one for selecting the excitation wavelength and another for capturing the emission spectrum, or alternatively, rotating one filter wheel aimed at selecting the excitation wavelength, while capturing the emission spectrum is by a triple dichroic filter. Approaches in which tunable filters (no moving parts) are used to control the excitation and/or emission wavelength have also been proposed. Recently, multispectral interference filters have also been used to enable imaging multiple fluorophores. Means of changing the dichroic mirror (e.g., by changing filter cubes) is also required. It is also frequently necessary to readjust the focus of the image at each wavelength and sometimes even the CCD camera exposure time must be changed to achieve higher signal-to-noise ratios. Collectively, these limitations create a registration problem. The resulting monochrome images, each corresponding to the emission of a different fluorescent dye, are then pseudo-colored and superimposed (using a digital computer with readily available off-the-shelf software). The resulting image shows the location of several fluorescent markers, each colored with a different pseudo-color. Since slight changes in the position of the dichroic mirror will cause translational shifts in the digitized images, it is necessary to use multiple wavelength dichroic mirrors [for use of a dichroic with quadruple wavelength band-pass properties see, Hiraoka et al. (1992) Seminars in Cell Biology, Vol. 2, pp. 153–164] or to register the images prior to their superposition. The image registration approach is more common, despite the fact that image registration is a difficult problem which can be time consuming and often produces only marginally satisfactory results. These are technical challenges which must also be addressed when acquiring multicolor fluorescence images [Waggoner et al. (1989) Part B of Methods in Cell Biology, Vol. 30, Ch. 17, pp. 449–478, edited by Taylor and Wang, Academic Press Inc.].

The spectral bio-imaging method of the present invention thus overcome one of the fundamental limitations imposed by filter based approaches to fluorescence imaging. By enabling the simultaneous measurement of the emission spectrum of an unlimited number of fluorescent dyes (including dyes whose emission spectra overlap to a great extent, as demonstrated hereinbelow in the Examples section for the Texas-Red and Rhodamine fluorophores), spectral bio-imaging eliminates the need for sequentially acquiring images of the emissions of multiple fluorescent probes. The advantage of using a spectral bio-imaging system is greatest when the used fluorescent probes can be excited by a common excitation source. In this case, a single spectral image acquisition can capture the fluorescence emission of an almost unlimited number of dyes and the need to (1) select non-overlapping dyes; (2) change filter cubes; (3) change excitation or emission filters; (4) optimize the focus and/or exposure time or (5) register the images, is eliminated. The challenge, of course, is to select suitable dyes that can be excited with a common source. Dyes which are excited by fluorescence energy that is transferred to/from one another are thus ideally suited for multi-color fluorescence imaging using a spectral bio-imaging system. Clearly, the use of dyes with similar emission properties will make visual detection (e.g., under the microscope) more difficult; however, this limitation is solved using the spectral bio-imaging method of the present invention.

Specifically, having measured the spectrum with the SpectraCube™ system, it is possible to distinguish among many different spectra, even if there are only slight spectral differences amongst them.

In principle, it is better to use a spectral range which is as broad as possible because then the range in which spectral changes can be observed is larger and the result is more accurate. On the other hand, if one wants to use few fluorophores each having a different colors emission simultaneously, one must make sure that each one of those fluorophores is excited at the right spectral range and that one could detect its emission at the right spectral range. Using a triple band filter enables to excite at three different excitation bands simultaneously and to detect the emission at three different bands as well. On the other hand, dividing the spectral range to six bands results in very narrow bands. A narrow band means that only very few measurement points fall in the band when measured by the system. On the other hand, when using a double band, the spectrum is divided only to four and therefore the width of each band is larger. This means that more measurement points are found for each measured fluorophore, and therefore the ability to differentiate amongst similar fluorophore increases. Therefore, it is presently preferred to employ a double band filter mounted onto the fluorescent microscope for implementing the method of the present invention using the SpectraCube™ system.

b. Spectral Identification of Multiple Fluorophores

The use of the spectral bio-imaging method according to the present invention enables the simultaneous measurement of many dyes (i.e., fluorophores) in one measurement. There is no restriction on the type of dye, even dyes that overlap spectrally (e.g., Rhodamine and Texas-Red) can be identified as will be exemplified below (see, Example 2 and 3) by applying suitable algorithms (e.g., linear combination for background subtraction, etc.) and their occurrence mapped in an image. However, if many dyes are to be used simultaneously, careful consideration should be given to their excitation wavelengths, fluorescence intensities and emission spectra. When this is done properly, the results can be analyzed quantitatively as well. For example, the relative concentration of several proteins can be mapped in a single measurement using suitable fluorescently tagged antibodies which specifically bind to these proteins. By using standard calibrated dyes, the absolute concentrations can also be determined.

One important example where the detection of multiple fluorescent probes can be a significant advantage is FISH (fluorescent in situ hybridization) [Emanuel (1993) Growth Genetics and Hormones 9, pp. 6–12], which is used to analyze genes at the chromosome level, and find possible genetic defects such as gene/chromosome amplification, deletion, translocation, rearrangement and other abnormalities.

Certain diseases and disorders, including many cancers and birth defects, are genetic disorders caused by defects in one or more genes. Many other diseases are known or believed to have a genetic component(s), that is, there exists genetic defect(s) that does not alone cause the disease but contributes to it, or increases the probability of developing the disease later in life, phenomena known in the art as multifactorial diseases and genetic predispositions. Correlation of visible genetic defects with known diseases would allow doctors to make definitive diagnoses, and permit early detection and treatment of many diseases. Genetic counseling could alert prospective parents and at-risk individuals to the possibility of potentially serious medical problems in the future, permitting appropriate intervention.

More than 5,000 genetic disorders have now been identified, many of which are associated with multiple genetic defects. After the discovery that chromosomes are the carriers of hereditary information, scientists reasoned that it should be possible to document visible defects in chromosomes that were responsible for specific disorders. In the 1960's, staining techniques were developed for microscopy-based classification of metaphase chromosomes spread onto glass slides. For several decades, visual analysis of chromosomes banding patterns has been used to correlate human genetic disorders with observed structural abnormalities in metaphase chromosomes. Chromosomes are typically examined by brightfield microscopy after Giemsa staining (G-banding), or examined by fluorescence microscopy after fluorescence staining (R-banding), to reveal characteristic light and dark bands along their length. Careful comparison of a patient's banding pattern with those of normal chromosomes can reveal abnormalities such as translocations (exchange of genetic material between or within chromosomes), deletions (missing chromosomes or fragments of chromosomes), additions, inversions and other defects that cause deformities and genetic diseases.

However, many serious genetic diseases, such as for example cystic fibrosis (CF) and many others, are caused by mutations that involve addition, deletion or substitution of only one or a few nucleotides. Such small defects are not detectable by the chromosomal banding techniques described above, and for many years cytogeneticists have been working to develop techniques for locating and quantifying minute defects.

Fluorescent in situ hybridization (FISH) has evolved over the past 25 years through the improvement of a number of complementary techniques. Its emergence has been driven by the desire of cytogeneticists to develop better tools for mapping the precise location of genes on chromosomes, and to detect very small genetic defects not visible by gross staining of chromosomes. The human genome project (HGP), a bold initiative to identify and map all human genes, has identified interest in FISH and has hastened the development of much-needed DNA probes. Current FISH techniques have also been made possible by the concurrent development of powerful immunological probes, a growing variety of excellent fluorescent dyes for microscopy and spectroscopy, and dramatic improvements in the objectives, illuminators and filters used for fluorescence microscopy.

The power and utility of FISH is due to many factors: (1) FISH can be used not only on isolated chromosomes and nucleus, but also whole cells within fixed, paraffin-embedded tissue sections; (2) it can detect relatively small defects (ability of detecting smaller defects being constantly increased); (3) it can provide results relatively quickly; (4) its moderate cost allows it to be used in most diagnostic and research laboratories; (5) adaptation can be developed for various probes and specimen types; and, (6) high specificity and sensitivity can be achieved (7) within a short time, typically in the range two hours.

Many FISH applications require only that the cytogeneticist look through the eyepieces of a microscope, or at the image on the monitor, to determine whether a fluorescent label is present or absent. With somewhat more complex specimens, a simple count of one or two colored labels may be done. However, the ability to process digital images and extract numerical data from them adds a vast new set of capabilities to FISH techniques. An appropriate imaging method, such as the method of the present invention, can enhance very faint FISH images so that labeled chromosomes and loci are clearly identifiable. Under readily achieved experimental conditions, the number of labeled sites can be automatically counted. In addition, the intensity at each labeled site can be measured and the amount of DNA calculated to reveal, for example, the number of copies present of a particular gene. Emerging techniques such as multicolor FISH employ color image analysis to detect and quantify multiple (3,4,5 and more) fluorescent probes.

As discussed above, FISH can provide information on the location of the labeled probe, the number of labeled sites on each chromosome, and the intensity of labeling (the amount of genetic material) at each site. Centromeric (repetitive DNA) probes and chromosome paints are used to tag and count the number of copies present of each targeted chromosome. Locus-specific probes are used to map the location of small regions of genetic material. These types of probes can be used on intact interphase nucleus as well as metaphase chromosome spreads, and can be counted visually or automatically by a suitable algorithm. They are routinely used to identify genetic diseases characterized by having too many or too few copies of a specific chromosome, chromosome fragment, or gene.

In very early stages of some cancers, long before the cells are recognizably abnormal, there may be an increase in the number of specific genes, phenomenon known in the art as gene amplification, that are detectable using locus-specific probes as homogeneously stained regions (HSR) and/or double minute chromosomes. Using FISH to detect chromosome abnormalities in cancerous cells may point out the developmental stage the disease have reached and therefore to select the most suitable treatment(s), many of which are stage specific in their effectiveness. Thereby precious time is saved and patient's suffering is minimized, selecting the most effective stage specific treatment.

It is possible to uniformly label the entire surface of one specific chromosome by isolating the chromosome (using flow cytometry, for example), physically (e.g., by sonication) or enzymatically (e.g., by endonucleases) chopping it up, and generating a set of probes against all of the fragments. Whole chromosome probes, also known as chromosome paints, fluorescently label all copies of their target chromosome. One important application of chromosome painting is the detection of translocation of genetic material between two chromosomes, as characteristically occurs in early stages of certain cancers, yet other chromosome aberrations are also detectable.

For example, if chromosome A is specifically labeled with a green paint and chromosome B is labeled with a red paint, any translocation of genetic material from A to B will appear as a green area on a red chromosome (and vice versa). Typically, chromosome paints generated from normal chromosomes are used to detect deletions or translocations on abnormal (patient) chromosomes. Reverse chromosome painting uses probes generated from an abnormal chromosome to identify DNA from various normal chromosomes which contributed material to the abnormal chromosome. The method of the present invention, as exemplified hereinbelow in the Examples section, enables to paint the 24 different chromosomes comprising the human karyotype (i.e., genome) each in a different color and simultaneously detect, identify and meaningfully display a color human karyotype, using a single hybridization followed by a single measurement.

Comparative genomic hybridization (CGH) is a variation of reverse chromosome painting in which two cocktails of DNA probes are generated from entire sets of chromosomes. One cocktail is generated from a set of normal chromosomes, and another from a set of abnormal (e.g., tumor) chromosomes. The two sets of probes are generated using different reporter molecules so that, for example, normal DNA will exhibit red fluorescence, and abnormal DNA will exhibit green fluorescence. A normal metaphase spread is hybridized simultaneously with both cocktails, and currently evaluated using color image analysis. Regions of normal chromosomes that fluoresce more intensely green than red indicate that DNA amplification (multiple gene copies) has occurred at that gene in the patient's abnormal cells. Regions with more red than green fluorescence (decreased green/red ratio) indicate sites of genetic deletions in the patient's chromosomes, and regions with equal green and red fluorescence indicate that no gross DNA changes have occurred at that site. For further details regarding CGH, see du-Manoir et al. (1993) Detection of complete and partial chromosome gains and losses by comparative genomic in situ hybridization. Hum. Genet. 90, 590–610. CGH and related techniques are more complex than previous labeling techniques, yet they offer the ability to detect and quantify more subtle and extensive genetic alterations than were previously possible. The method of the present invention is highly suitable for these types of analyses.

From what has been said above, it follows that karyotyping, translocation/rearrangement detection, chromosome deletion/amplification, and gene mapping will greatly benefit by the use of the sensitive, quantitative, spectral imaging method of the present invention that builds a whole spectral image at relatively high spectral resolution, instead of a simple color fluorescence image. This is because such method decreases the sample preparation time and is able to distinguish between a hybridized fluorescent probe from one that is residual in the background (by small spectral shifts), and is able to measure simultaneously a large number of probes, which large number is the first time to be achieved in a single measurement.

Thus one of the objectives of the present invention is to provide a FISH imaging method designed to exploit the advances in probe technology. According to the present invention there is a possibility of greatly increasing the number of probes that can be analyzed in any given chromosome analysis, as well as dramatically increasing the speed and degree of automatization at which this information can be acquired as compared with prior art methods.

The FISH imaging method of the present invention exploit the advantages of the SpectraCube™ system, that is capable of simultaneously acquire fluorescence spectra from all pixels of the microscope field of view and detect the location of many fluorescent probes in a single experiment. In conjunction with the availability of chromosome specific probes and novel labeling strategies, and as is exemplified in the Examples below, the method is capable of creating a FISH karyotype with each chromosome being painted with a different color (i.e., 24 different colors for a human karyotype). This method result in extremely high sample throughput and allow analysis of essentially unlimited number of probes.

As delineated above, the key concepts of the present invention is the use of many fluorescent probes in FISH assays. Numerous methods are available to label DNA probes for use in FISH, including indirect methods whereby a hapten such as biotin or digoxigenin is incorporated into DNA using enzymatic reactions. Following hybridization to a metaphase chromosome spread or interphase nucleus, a fluorescent label is attached to the hybrid through the use of immunological methods. More recently, fluorescent dyes have been directly incorporated into probes and detected without the use of an intermediate step. Standard FISH dyes include fluorescein, rhodamine, Texas-Red and cascade blue, and multiprobe FISH analysis can be accomplished by labeling different probes with different haptens or fluorescent dyes and combinations thereof, known in the art as combinatorial labeling [see, Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. Alternatively, a pool of a given probe may be divided into sub-pools, each labeled with a different fluorophore, after which the sub-pools are regrouped to yield otherwise similar hybridization results, a method known in the art as combinatorial hybridization [see, du-Manoir et al. (1993) Detection of complete and partial chromosome gains and losses by comparative genomic in situ hybridization. Hum. Genet. 90, 590–610, which is incorporated by reference as if fully set forth herein]. According to both labeling strategies obtained are combinatorial probes. Thus, when the term "combination of fluorophores" is used herein in this document and especially in the claims below, it refers both to combinatorial labeling and to combinatorial hybridization as described above.

Fluorescence is a form of luminescence which occurs after photons of light are absorbed by a molecule known as a fluorophore at the ground electronic state. The molecule is raised to an excited state as a result of electron transfer to a higher energy orbit. This excess energy is lost when the electron returns to the original ground state, releasing a quantum of light. The fluorescence light is of longer wavelength than the absorbed light. This shift is limited, causing the emission to be close to the excitation wavelength. Because of this, the fluorophores which can be excited in one spectral range emit in a similar spectral range. For example if the excitation is in the blue range the emission is expected in the green. So if one wants to use many different probes which emit different spectra it is evident that they must be close in wavelength, and also often overlap; as a consequence, spectral resolution is of critical importance to be able to discriminate between the different probes.

According to the method of the present invention, individual probes (a probe as referred to herein in this document also refers to a combinatorial probe) are assigned a pseudo-color (i.e., by an RGB algorithm) or an artificial color (i.e., a predetermined color according to a classification algorithm such as classification mapping or principal component analysis as described above) and the information is displayed on a computer screen. The use of multicolor fluorescence opens up a possibility of extending FISH into important clinical applications which may benefit from multiple probes. Examples include aneuploidy and chromosome structural studies, detection of marker chromosomes, complete FISH karyotypes and multicolor chromosome banding. Since multiple information may be gained from a single hybridization, throughput is increased and internal standards may be used in order to assess gene dosage effects or to determine the extent of deletions.

The method of the present invention, utilizes detection of fluorescence excited by a white or coherent monochromatic light source in few narrow spectral bands and a sensor with cooled CCD. Thus, multiple spectra, each representing a different probe, may be simultaneously measured. This, in turn, increases the speed and accuracy of image acquisition, compared to conventional approaches which take multiple snapshots of chromosomes and then reconstruct the image, a process which is time consuming and generates artifactual results, all as described above. Hence, the present invention represents a highly significant progress over the state-of-the-art cytogenetic imaging, because it allows more sensitive, rapid and accurate detection of multiple probes.

Another objective of the method of the present invention is the generation of a multicolor banding pattern of chromosomes (i.e., bar-coding, multicolor banding karyotype) based on FISH and spectral imaging. For details regarding chromosome bar coding the reader is referred to C. Lengauer et al. (1993) Hum. Molec. Genet. 5, 505–512.

The first goal of the human genome project (HGP) is about to be completed. This goal is the generation of a physical map of the human genome. The term physical map refers to the cloning of the entire genome in large insert vectors such as YAC-clones or BAC-clones and the mapping of these clones by means of genetic, cytogenetic and physical mapping. Two major sources of human DNA were used for this endeavor, radiation hybrid cell lines and YAC-contigs that contain overlapping clones for all human chromosomes. The completion of this map allows to retrieve for virtually every region in the genome specific clones that are required to identify genes that are causally involved in inherited or acquired genetic diseases including cancer. By combining FISH with multiple YAC- or BAC-clones or radiation hybrids and spectral imaging it is possible to generate a multicolor banding pattern for all human chromosomes that will ultimately link the genetic and the cytogenetic map.

As an example, consider the use of a radiation hybrid panel (Stanford panel) [see, Barret J. H. (1992) Genetic mapping based on radiation hybrids. Genomics 13, 95–103].
Each individual panel of the Stanford panel contains a set of DNA fragments with an average fragment size of ca. 5,000 Kbp. Each individual panel covers ca. 20% of the human genome. The cohyhridization of fluorescent probes derived from five such panels would therefore result in coverage of most of the genome and thus labeling of all human chromosomes. However, the fragments are randomly distributed in the individual panels. Therefore, the number of panels that are required for a complete coverage of the human genome is higher (e.g., 6–10 panels).

In the following description assumed is that five individual panels are used. The chromosome fragments of each of the panels are labeled with a different fluorophore (or a different combination of fluorophores, e.g., combinatorial labeling or hybridization strategies) by for example directly incorporating dUTP-conjugated fluorophores using primers derived from interspersed repetitive sequences (IRS, e.g., Alu sequences) in a method known in the art as IRS-PCR approach such as Alu-PCR, which guarantees an exclusive amplification and labeling of human sequences only. If DNA from a species other than human is to be thus amplified and or labeled, a species specific interspersed repetitive sequence (IRS) characterizing the genome of that species is to be used to derive suitable PCR primers. A single separate hybridization of one of the individual panels would give a banding pattern of a chromosome spread in one color with a coverage of about 20% of the genome and an average band size of 5,000 Kbp. Due to the random overlap of individual chromosome fragments in the five hybrid panels, the cohybridization of five differentially labeled groups (each group is represented by a single panel) of fragments would result in a banding pattern including bands that have pure colors, bands that include a combination of two, three, four, as well as five colors each, collectively 31 possible color combinations, which combinations can be distinguished using spectral imaging.

The generation of a multicolor high resolution banding pattern of chromosomes has two distinct advantages as compared to the use of chromosome painting probes (i.e., chromosome paints) as follows.

Chromosome painting is a well suited tool to detect interchromosomal aberrations such as translocation or homogeneously staining regions as well as additional chromosomes material such as marker chromosomes or double minute chromosomes. Intrachromosomal aberrations such as deletions and duplications would be detected only if the size of the aberrations affect the length of the chromosomes, whereas chromosomal inversions are not detectable at all by this method. However utilizing a multicolor banding pattern, inter- as well as intrachromosomal aberrations could be diagnosed because they would affect the sequence of the chromosomal bands.

One major advantage of multicolor high resolution banding pattern using pre-mapped DNA fragments (e.g., YAC-clones and radiation hybrids cell lines) is the possibility to integrate the genetic and the cytogenetic map. Each multicolor band is characterized by a specific set of sequence tagged sites. These are PCR products that occur only once in the genome.

Following is a description of the usefulness of the integrated cytogenetic and genetic map. For example, the lack of a specific color band on a chromosome derived from a tumor cell is indicative of a microdeletion that often reflects the loss of a tumor suppressor gene. The knowledge of the sequence target sites (STS's) that are specific for this band would allow to screen any large insert clone collection and retrieve a number of specific clones that are highly likely to contain the gene that is deleted in the described example.

It should be mentioned that with the large scale sequencing efforts now underway and with the integration of expressed tagged sites (loci that are known to contain a gene) the value of a hybridization based multicolor banding pattern would increase even more.

It is also conceivable that such a multicolor banding pattern could be readily automated. Despite considerable efforts automation of cytogenetic diagnosis based on conventional chromosome bands was so far not successful. The approach described hereinabove will not only be applicable for the generation of a hybridization based banding pattern of human chromosomes but also for other mammalian (e.g., mouse) and non-mammalian species. This will be particularly useful for the analysis in animal models of human diseases including cancer.

In analogy to the scenario described for the radiation hybrid panels, a multicolor banding pattern for all human chromosome could be achieved by cohybridization of a set on individual large insert clones such as YAC-clones, P1-clones, BAC-clones or, depending on the resolution that is desired the use of contigs (overlapping clones) from these sources. In further analogy to the use of radiation hybrid panels, a multicolor banding pattern could be introduced by deliberately labeling overlapping clones or contigs with different fluorophores. All advantages of the hybridization based chromosome banding approach has as compared to the use of chromosome paints or to conventional chromosome banding described above, applies to usage of large inserts clones as well. It will be appreciated by one ordinarily skilled in the art that the retrieval of clones involved in chromosome breakpoints or in chromosomal deletion would be even more straightforward than with the use of radiation hybrid panels.

Another source of chromosome fragments suitable for use for multicolor chromosome banding are fragments obtained by microdissection of chromosomes. Microdissected chromosomes fragments are generated by manual or laser micromanipulation of chromosome spreads as well known in the art. The fragments thus produced are typically multiplied by polymerase chain reaction using for example degenerated oligonucleotides primers (DOP) in a method known in the art as DOP-PCR, or using primers derived from interspersed repetitive sequences (IRS, e.g., Alu sequences) in a method known in the art as IRS-PCR.

Yet, an additional source of chromosome fragments suitable for use for multicolor chromosome banding are fragments generated by DNA restriction approaches that generate large DNA fragments and electrophoresis approaches capable of size separating large DNA fragments. As far as generating large DNA fragments by DNA restriction two approaches may be considered. According to the first, a partial digestion by an endonuclease (e.g., frequent or rare cutter) is used, whereas according to the second, a complete digestion by a rare cutter endonuclease (e.g., NotI), is used. The later is presently preferred since a complete digestion can be repeated to yield identical results in independent trials, whereas partial digestion is random in nature. Electrophoresis approaches capable of size separating large DNA fragments are well known in the art and include pulse field gel electrophoresis (PFGE). Thus, for example, extracting DNA from consecutive regions along a PFGE lane, labeling the DNA extracted from each of the regions using a different fluorophore and cohybridizing thus formed probes to chromosomes, would result in a multicolor banding pattern of the chromosomes similarly to as described above. Large DNA fragments may additionally be obtained via gradient centrifugation such as sucrose or cesium chloride gradients as well known in the art. Nevertheless, it will be appreciated that using these approaches do not provide a possibility to integrate the genetic and the cytogenetic map as described above and is therefore presently less favorable.

The generation of a multicolor banding pattern of chromosomes (i.e., multicolor banding karyotype) based on fluorescent in situ hybridization and spectral imaging can be used for various practical applications. These include for example (i) screen for chromosomal aberrations using for example specifically tailored clone sets; (ii) screening for telomeric deletions, which are otherwise difficult of detection; (iii) screening for chromosomal aneuploidies during prenatal diagnosis; (iv) screening for recurrent chromosomal breakpoints; (v) multicolor comparative genomic hybridization; (vii) combining multicolor FISH with other measurements of cytological and immunohistochemical stains for multiparameter analysis of tumor cells; (viii) combining multicolor banding patterns with conventional R- or G-bands; (ix) analysis of genetic aberrations directly in interphase cells; and (x) screening for chromosomal aberrations in radiation or mutagen exposed populations.

Following is a brief summary of likely applications of spectral bio-imaging in the field of molecular cytogenetics. Two major fields of cytogenetics in which spectral bio-imaging will have considerable impact with particular emphasis on diagnostic applications are: (i) clinical cytogenetics and (ii) tumor cytogenetics.

About 400,000 cases in both clinical and cancer cytogenetics are analyzed each year in the United States alone, using chromosome banding analysis. Chromosome painting could be performed in addition to conventional banding analysis and would help to identify marker chromosomes that cannot be characterized using banding alone.

Conventional chromosome banding analysis (conventional karyotyping) is still the most frequently used diagnostic procedure for detection of chromosomal aberrations in pre- and postnatal diagnostic. This includes the diagnosis of numerical aberrations like trisomy for chromosome 21 (and less frequently chromosome 13, 18, X, and Y). Conventional chromosomes banding analysis is used because it is so far the only screening test (or genome scanning method) available for chromosomal aberrations detection. This means that the entire chromosome complement, i.e., genome, can be assessed using a single experiment. This also explains why targeted FISH-procedures, these are experiments with probes specific for, e.g., chromosome 21, are used only as complementary methods. Using targeted FISH-procedures, chromosomal aberrations on chromosomes other than the one to which the probe is directed, escape the detection. On the other hand, the simultaneous painting of all chromosomes, according to the method of the present invention, and the possibility to distinguish all chromosomes by means of different spectra would circumvent these limitations of FISH analysis. It is conceivable that genome painting will become an important, if not mandatory, additional diagnostic method in prenatal diagnosis. This is even more likely because the spectral bio-imaging method of the present invention when applied using appropriate filters can detect both FISH fluorophores and DAPI counterstain in a single measurement and thus to provide a multicolor FISH image and a DAPI banding image of the same chromosome spread in a single measurement. Thus, the well established backbone of cytogenetic information is maintained and can be displayed together with the painting patterns. In this regard, it is noteworthy to mention that an automated identification of chromosomes will become possible. This goal could not be satisfactorily achieved with conventional banding methods alone.

In the field of postnatal cytogenetic diagnosis spectral bio-imaging based chromosome painting will become tremendously helpful in identifying marker chromosomes. The diagnostic obstacle here is to ascertain whether discrete, small chromosomal fragments that are translocated and give rise to an aberrant chromosome are balanced (i.e., no copy number change) or unbalanced, leading to partial trisomies or monosomies that are a major source of human malformation and mental retardation syndromes, many of which remain cryptic in origin.

All the above mentioned approaches utilize chromosome painting probes. With specific probe sets in combination with spectral bio-imaging a hybridization based chromosome banding is possible. Those probes can be chosen with unprecedented resolution or can be tailored to address specific diagnostic problems like the microdeletions of telomere sequences that are a yet underestimated cause of genetically caused diseases.

Probes that are useful in the attempts to generate a multicolor banding pattern off the entire chromosome complement (i.e., genome) are either microdissection libraries that contain chromosome band specific sequences, YAC (or other) contigs, radiation induced hybrid cell lines with a specific and known representation of human sequences or large chromosome fragments generated by endonuclease digestion followed by PFGE size separation, that produce a fixed multicolor banding pattern along all chromosomes. The change in the color pattern would indicate, with high resolution, the presence of chromosomal aberration(s). It is clear that such an approach is highly flexible in its design, and could be easily automated.

Acquired chromosomal aberrations are predominantly associated with malignant transformations. Roughly, two malignancies can be discerned: (i) hematological malignancies and (ii) solid tumors. Since the cells from hematological malignancies are easily cultured in vitro, the chromosome banding analysis of those tumors is one of the success stories in cytogenetic and genetic cancer research. Two well known examples include the identification of the Philadelphia chromosome in chronic lymphatic leukemia (CLL) and the a specific chromosomal aberration in Burkitt's lymphoma. Many more tumor specific chromosomal aberrations were described in hematological malignancies in the last decade and are used as a diagnostic and research tool. In many cases the delineation of a recurrent chromosomal aberration has allowed to identify on a molecular basis the mechanism of malignant transformation. Disturbingly, less is known in the field of solid tumors (such as breast, colon, brain lung and others tumors). This discrepancy is even more disturbing because solid tumors play a much higher role in human morbidity than hematological malignancies. The discrepancy is mainly due to technical difficulties common in solid tumor cytogenetics. Solid tumors cells are often difficult to culture, the chromosome preparations are of poor quality, preventing a high resolution cytogenetic analysis, and secondary chromosomal aberration, not necessarily related to tumor initiation or progression are a common feature of these tumors. The availability of a hybridization based chromosomal screening test (i.e., chromosome painting) fills in a methodological gap and is as described above desperately required. Partly, comparative genomic hybridization helps in this respect. However, structural chromosomal aberration cannot be detected and always displays as average of chromosomal aberration in a cell mixture. It is very likely to predict that hybridization based karyotyping would become a widespread method for the delineation of recurrent chromosomal aberrations in solid tumors, both in basic research and in the diagnostic laboratory. Again, refinements of the technique, that would employ region or band specific probes are going to increase the resolution dramatically.

The generation of a multicolor banding pattern of chromosomes (i.e., multicolor banding karyotype) and chromosome painting based on FISH and spectral imaging, can be used for various additional applications. These include for example (i) biological dosimetry, wherein screening of metaphase plates from individuals exposed to radiation or chemicals known to induce chromosomal aberrations is performed to establish damages; (ii) chromosome evolution, wherein FISH is used to reconstruct chromosomal rearrangements that occurred during evolution; (iii) the analysis of chromosomal aberrations in animal models of human diseases, in particular cancer, would be greatly facilitated using hybridization based karyotyping; (iv) interphase cytogenetics, wherein the simultaneous enumeration of chromosome copy number in intact interphase cells has application for the detection of aneuploidies in prenatal diagnosis and in cancer research and diagnostic of minimal residual diseases, in combination with confocal laser scanning microscopy this would become a splendid research tool for the analysis of the architecture of the interphase chromatin; (v) cytological diagnosis, wherein complementation of histochemical diagnosis by using multiprobe FISH directly on tissue section and nucleus, possibly in combination with confocal laser scanning microscopy or deconvolution algorithms.

Thus, according to the present invention there is provided a fluorescent in situ hybridization method which method includes the steps of (a) providing a cell nucleus having chromosomes, the chromosomes being hybridized with at least one nucleic acid probe being labeled with at least one fluorophore; (b) viewing the cell nucleus through a fluorescence microscope, the fluorescence microscope being optically connected to an imaging spectrometer, the fluorescence microscope and the imaging spectrometer being for obtaining a spectrum of each pixel of the cell nucleus.

Further according to the present invention there is provided a method for hybridization based multicolor chromosome banding, which method includes the steps of (a) providing a cell nucleus of a first species having a genome and chromosomes, the chromosomes being hybridized with at least one group of chromosome fragments covering at least a fraction of the genome of the first species, the fragments being labeled with at least one fluorophore; and (b) viewing the cell nucleus through a fluorescence microscope, the fluorescence microscope being optically connected to an imaging spectrometer, the fluorescence microscope and the imaging spectrometer being for obtaining a spectrum of each pixel of the cell nucleus.

It will be appreciated by one ordinarily skilled in the art that any imaging spectrometer may be suitable to implement the methods of the present invention. These include grating and filters based imaging spectrometers as described in the background section above. Yet, for reasons described above, it is presently preferred that an interferometric based imaging spectrometers will be employed.

Thus, obtaining a spectrum of each pixel of said cell nucleus is preferably by (i) collecting incident light simultaneously from all pixels of the cell nucleus using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the cell nucleus for the entire duration of the measurement and so that the real image of the cell nucleus is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) rotating or translating (i.e., scanning) one or more of the elements of the interferometer system, so that the optical path difference between the two coherent beams generated by the interferometer system is scanned simultaneously for all the pixels of the cell nucleus; and (v) recording signals of each of the detector elements as function of time using a recording device to form a first spectral cube of data; the methods further includes the step of (c) interpreting the first spectral cube of data using a mathematical algorithm.

The nucleic acid probes may include loci, fragmented chromosomes, yeast artificial chromosomes each including an insert, plasmids, cosmids, phagemids or viral vectors each including an insert, complete (i.e., whole) genomes of a species or a cancerous tissue and combinations thereof. The cell nucleus may be a nucleus during interphase, a nucleus during and a nucleus during meiosis and accordingly the chromosomes may be interphase chromosomes, chromosomes during mitosis or chromosomes during meiosis. The number of nucleic acid probes may be one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four or greater than twenty four, each of the probes include a different fluorophore or a different combination of fluorophores (i.e., a combinatorial probe, obtained either by combinatorial labeling or hybridization strategies, as described above). According to a preferred embodiment the fluorophores are conjugated to a nucleotide or a nucleotide analog.

The mathematical algorithm may be: (a) a Red-Green-Blue color image computation using predefined wavelength ranges; (b) a classification mapping analysis computing for the spectrum of each of the pixels a spectral difference from at least one reference spectrum; (c) a linear combination analysis, the analysis is for a background subtraction combined with classification mapping analysis; (d) a principal component analysis; and (e) any other algorithm suitable for pixels classification according to their associated spectra.

The method of the present invention may be used for various research and medical applications. Thus, for example, the method may be used for (i) high resolution detection of telomere deletions, previously undetectable; (ii) for detecting chromosomal aberrations such as recurrent chromosomal aberrations and/or secondary chromosomal aberrations characterizing various malignancies; (iii) for detecting the stage of a malignancy according to the presence of recurrent chromosomal aberrations and/or secondary chromosomal aberrations; (iv) the detection of the stage of the malignancy may be used for selecting a treatment for the malignancy; (v) for following the efficiency of an anti-cancer treatments such as radiation and a chemotherapoietic treatment; and (vi) for detecting chromosomal aberrations following exposure to mitogenic agents such as, but not limited to, radiation and mitogenic chemicals such as occupational mitogenic chemicals for example petrochemicals and as best.

According to the method for hybridization based multi-color chromosome banding, the chromosome fragments may be of any suitable source. Preferably the fragments are derived from radiation hybrid cell lines such as human-hamster radiation hybrid cell lines, YAC-clones (e.g., contigs), BAC-clones, size separated endonuclease digestion products of a complete genome of a selected species or and microdissected chromosome fragments from that species. Yet other sources of chromosome fragments such as ones obtained by gradient centrifugation may be employed to implement the method of the present invention. Collectively the fragments may cover any fraction of the genome. Examples include a 10–20%, 21–30%, 31–40%, 41–50%, 51–60%, 61–70%, 71–80%, 81–90% and coverage. The method is preferably exercised on the human species, yet any desired species (e.g., mouse) may be the subject of analysis according to the method. Furthermore, the method may be exercised in an interspecies fashion wherein the chromosomes are from a first species (e.g., mouse, monkey, etc.) and the chromosome fragments are from a second species (e.g., human). In a preferred embodiment the chromosome fragments are grouped into groups, each of the groups is labeled with a different fluorophore or combination of fluorophores. Labeling of the chromosome fragments may be achieved by for example IRS-PCR such as Alu-PCR if the fragments are from human.

While the invention has been described with respect to a limited number of embodiments, it will be appreciated that many variations, modifications and other applications of the invention may be made.

Reference is now made to the following examples, which together with the above descriptions, illustrate the invention.

EXAMPLE 1

BRIEF DESCRIPTION OF EXPERIMENTAL PROTOCOLS

Alu-PCR of YAC Clones and Hybrid Cell Lines

Interspersed repetitive elements (IRS)-PCR (e.g., Alu-PCR) is a fast and reliable method to generate probe sequences for FISH from YAC-clones or hybrid cell lines, etc. Using this approach, the fluorescent background staining is lower as compared to the use of entire YAC or hybrid cell line DNA, labeled by, e.g., Nick-translation or random priming.

Furthermore, YAC-DNA embedded in agarose plugs, yeast colonies on agar-plates as well as purified YAC-DNA can be amplified. The protocol presented hereinbelow essentially follows the one described by Lengauer et al. Cancer Res. 52: 2590–2596 (1992), which is incorporated by reference as if fully set forth herein.

Solutions: 10×PCR-buffer (Perkin-Elmer II); 25 mM each dATP, dCTP, dGTP, dTTP (collectively dNTP); 50 $\mu$M Alu-Primer CL1 (5' TCC CAA AGT GCT GGG ATT ACA G 3', SEQ ID NO:1); 50 $\mu$M Alu-primer CL2 (5' CTG CAC TCC AGC CTG GG 3', SEQ ID NO:2).

Procedure: 100 ng DNA (or equivalent amount of DNA in agarose plugs or yeast colonies), 10 $\mu$l 10×PCR-buffer (Perkin-Elmer II), 10 $\mu$l 15 mM MgCl$_2$, 1 $\mu$l 25 mM dNTP, 0.5 $\mu$l 50 $\mu$M Primer CL1, 0.5 $\mu$l 50 $\mu$M Primer CL2, 0.5 $\mu$l Taq DNA Polymerase (Perkin-Elmer, 2.5 U), and ddH$_2$O to complete the reaction volume to 100 $\mu$l, were mixed and were subjected to 30 PCR cycles of 1 min at 96° C., 0.5 min at 37° C., and 6 min at 72° C. PCR results were viewed by ethidium bromide stained 1.2% agarose gel under U.V. illumination. PCR products were ethanol precipitated, redissolved in 50 $\mu$l ddH$_2$O and stored at 4° C. until use.

DOP-PCR for the Amplification of Minute Amounts of DNA

The sequence independent amplification of DNA, i.e., degenerated oligonucleotides primers (DOP)-PCR, was first described by Telenius et al. Genes Chromosomes Cancer 4: 257–263 (1992), which is incorporated by reference as if fully set forth herein. Meanwhile several modifications were published (Bohlander et al., Genomics 13: 1322–1324, 1992; Milan et al., Cytogenet. Cell Genet. 62: 139–141, 1993; Guan et al., Genomics 22: 101–107, 1994).

The protocol used for the amplification of minute amounts of DNA from few tumor cells basically follows the protocol described by Telenius et al. Slight modifications are described in Speicher et al., Hum. Mol. Genet. 2: 1907–1914 (1993), which is incorporated by reference as if fully set forth herein. Using this protocol a successful amplification of as little as 30 pg template DNA was achieved.

Solutions: 10×PCR-buffer (Perkin-Elmer II); 25 mM $MgCl_2$; 5 mM each dATP, dCTP, dGTP, dTTP (collectively dNTP); 17 $\mu$M 6-MW primer (5' CCG ACT CGA GNN NNN NAT GTG G 3', SEQ ID NO:3).

Procedure: 100 ng DNA (or less), 5 $\mu$l 10×PCR-buffer, 4 $\mu$l 25 mM $MgCl_2$, 2 $\mu$l 5 mM dNTP, 5 $\mu$l 6-MW-primer 17 $\mu$M (final concentration 1.7 $\mu$M), 0.5 $\mu$l Taq Polymerase (2.5 units), and $ddH_2O$ to complete the reaction volume to 50 $\mu$l, were mixed and were subjected to PCR cycles as follows. 10 min at 93° C., followed by five cycles of 1 min at 94° C., 1.5 min at 30° C., 3 min transition 30–72° C., and 3 min extension at 72° C., followed by 35 cycles of 1 min at 94° C., 1 min at 62° C., and 3 min at 72° C., with an addition of 1 sec/cycle to the extension step and a final extension of 10 min. PCR results were viewed by ethidium bromide stained 1.2% agarose gel under U.V. illumination. PCR products were ethanol precipitated, redissolved in 50 $\mu$l $ddH_2O$ and stored at 4° C. until use.

Labeling of Probes Using DOP-PCR or IRS-PCR

Solutions: 10×PCR-buffer (Perkin-Elmer II); 25 mM $MgCl_2$; 2 mM each dATP, dCTP, dGTP and 1.5 mM dTTP (collectively dNTP); suitable amount(s) of the relevant primer(s), e.g., 100 $\mu$M 6-MW primer for DOP-PCR; and 1 mM labeled-dUTP.

Procedure: 400–600 ng DNA, 10 $\mu$l 10×PCR-buffer, 8 $\mu$l 25 mM $MgCl_2$, 2 $\mu$l dNTP, 2–4 $\mu$l primer(s) depending on the primer(s) used, 2 $\mu$l Taq Polymerase (10 units), 5 $\mu$l 1 mM labeled-dUTP, and $ddH_2O$ to complete the reaction volume to 100 $\mu$l, were mixed and were subjected to 25 PCR cycles of 1 min at 94° C., 1 min at 56° C., and 4 min at 72° C., final extension for 20 min. Labeled PCR products were ethanol precipitation, dissolved in 50 $\mu$l $ddH_2O$ and stored at −20° C. until use.

Denaturation of probe and specimen.

Denaturation of probe: varying amounts of probe DNA were used depending on the type of probe. The amounts given below were used for a hybridization area of 18×18 $mm^2$. Prior to denaturation probes were resuspended in 10 $\mu$l hybridization solution (see below) in the following concentrations:

| | |
|---|---|
| Centromere specific DNA probes: | 1–2 ng/$\mu$l |
| Chromosome painting probes: | 20–40 ng/$\mu$l |
| Locus specific probes: | plasmid 10 ng/$\mu$l |
| | phage 20 ng/$\mu$l |
| | cosmid 5–8 ng/$\mu$l |
| | YAC or cell hybrids (Alu-PCR products) 10 ng/$\mu$l |
| | single copy cDNA probes 10 ng/$\mu$l |
| | Genomes (CGH) 20–50 ng/$\mu$l. |

Probe DNA was ethanol precipitated in the presence of carrier DNA and also, when complex probes such as chromosome paints were used, competitor DNA (e.g., human genomic DNA). The preferred carrier DNA was salmon sperm DNA at a final concentration (in the hybridization solution) of 100 ng/$\mu$l. The probe DNA was dried in a speed-vac, and resuspended in 5 $\mu$l formamide at room temperature on a vortex equipped with a tube carrier. After approximately 30 min of vortex, 5 $\mu$l of 20% dextran sulfate in 2×SSC were added. Probe DNA was denatured at 76° C. for 5 min, and quenched on ice. When complex probes (e.g. chromosome painting probes) were hybridized, a pre self-annealing step was included at 37° C. for 30 min. The DNA probes in CGH experiments were preannealed for 2 hours.

Denaturation of specimen: For most applications metaphase chromosomes can be used for the hybridization without any additional pretreatments. However, for some applications and if fluorescent background seems to be high, a pretreatment step might help. A pretreatment protocol that is used frequently when fluorescent background seems to be especially high is described hereinbelow.

Solutions: 20 mg/ml DNase free RNase-A in ddH2O; 10% Pepsin in $ddH_2O$; and 50 ml 1M $MgCl_2$+950 ml 1×PBS (1×PBS/$MgCl_2$).

Procedure: Slides were equilibrated in 2×SSC at room temperature and were subjected to RNase treatment followed by pepsin treatment as follows.

RNase was dilute 1:200 and 200 $\mu$l were applied onto the slides which were thereafter covered with a 24×60 $mm^2$ coverslips. Incubation was at 37° C. for 45–60 min after which coverslips were removed and slides were washed 3×5 min in 2×SSC at room temperature. 50 $\mu$l pepsin were added to 100 ml 37° C. prewarmed 0.01 M HCl (in coplin jar). RNase treated slides were incubated in the above pepsin-HCl solution in the coplin jar for 5–10 min at 37° C. and thereafter slides were washed 2×5 min in 1×PBS at room temperature with agitation and once in 1×PBS/$MgCl_2$ for 5 min. Following pepsin treatment, slides were postfixated in presence of formaldehyde as follows. A fresh solution of 1% formaldehyde in 1×PBS/$MgCl_2$ was prepared by adding 2.7 ml of 37% formaldehyde to 100 ml 1×PBS/$MgCl_2$. Slides were incubated in the formaldehyde solution for 10 min at room temperature. Thereafter, slides were washed 1×5 min in 1×PBS at room temperature under agitation. Slides were dehydrated in 70, 90, 100% Ethanol for 3 min each, and air dried.

The denaturation of the specimen is more critical than the denaturation of the probe DNA. Two goals need to be reached (i) the probe penetration should be optimal with a minimum of loss in specimen morphology, and (ii) a minimum of target sequence loss. The optimal denaturation time varies, between different specimen, e.g. metaphase chromosome and tissue sections, and from preparation to preparation. Therefore, for optimal performance, the conditions should be explored for each batch of specimen. In the following procedure, average times are given for metaphase chromosomes:

Solutions: Denaturation solution: 70% formamide, 2×SSC (stored at −20° C.); Ethanol series (70%, 90%, and 100%) in $ddH_2O$.

Procedure: 120 $\mu$l of the denaturation solution were applied onto the slides and they were covered with a 24×60 $mm^2$ coverslips. Slides were thereafter placed for 2 min (or more depending on the specimen) on a glass plate preheated to 80° C. in an oven. Coverslips were removed and slides were dehydrate through an ethanol series (70%, 90%, 100%) and air dried.

In Situ Hybridization

Hybridization takes place at 37° C. Certain probes, however, need higher hybridization temperatures. This applies in particular to repetitive DNA probes in order to ensure their chromosome specificity (alternatively, the stringency can be increased by decreasing the salt concentration in the hybridization solution, e.g. to 0.5×SSC final). Since during hybridization the coverslips are sealed with rubber cement, a moist chamber is not required. A hybridization time of 12 to 16 hours is sufficient for all locus specific probes, i.e., cosmid probes or phage clones. Chromosome painting is also done overnight, however, if chromosomes of distant species are to be painted with human probes, longer hybridization times (and higher probe concentrations) are preferred. When entire genomes are hybridized (e.g., CGH) the hybridization time is extended to 2 to 4 days.

Fluorescence Probe Detection

Fluorescence probe detection can be either direct or indirect. In the direct format, the probes were labeled with dUTP's linked to fluorochromes (i.e., fluorophores). These probes do not need immunological amplification steps. However, signals can be amplified with fluorochrome conjugated antibodies directed against the fluorochrome linked to the dUTP, e.g. FITC-conjugated rabbit anti-FITC. In general, directly labeled probes result in slightly decreased signal intensity, however, background fluorescence is lower as well. Many painting probes are available in the direct format and perform very well. The direct approach is described in detail in Wiegant et al., Nucl. Acids Res. 19:3237–3241, 1991 and Wiegant et al., Cytogenet. Cell Genet. 63:73–76, 1993, both are incorporated by reference as if fully set forth herein.

The indirect format employs dUTP's that are linked to haptens such as biotin, digoxigenin, dinitrophenol and the like. The probe sequences are either visualized via avidin conjugates to fluorochromes, or antibodies directed against digoxigenin and dinitrophenol. The biotin and the digoxigenin system perform excellent, both with respect to sensitivity and flexibility, and are the methods of choice for many applications. A routine double label detection is described below. A great variety of different fluorescent detection formats is available for visualizing biotin and digoxigenin labeled probes. Biotin and digoxigenin labeled probes have the distinct advantage that a signal amplification step can be performed easily. Biotin labeled probes can be amplified using the sandwich technique described by Pinkel et al. Proc. Natl. Acad. Sci. USA 83: 2934–2938 (1986), which is incorporated by reference as if fully set forth herein. Digoxigenin labeled probes can be detected either using antibodies against digoxigenin that are coupled to fuorochromes, or via a mouse antibody against digoxigenin that is subsequently visualized using antibodies against mouse. Avidin (or streptavidin) conjugates are commercially available with the following fluorochromes: AMCA, Cascade-Blue, FITC, Texas-Red, Rhodamine, TRITC, Cy3, Cy5. Antibodies against digoxigenin are commercially available with the following fluorochromes: anti dig FITC (Fab-fragments), anti dig rhodamine (Fab-fragments), mouse anti dig IgG, goat (sheep) anti mouse FITC, goat (sheep) anti mouse TRITC, goat (sheep) anti mouse Cy3, goat (sheep) anti mouse Cy5.

Probe detection and signal amplification: In the following, a typical detection and amplification procedure for two probes that are labeled with biotin and digoxigenin is described.

Solutions: Wash I: 50% formamide, 2×SSC, pH 7.0, prewarmed to 45° C. Wash II: 0.1×SSC, prewarmed to 60° C. Wash III: 4×SSC, 0.05% Tween, prewarmed to 37° C. Wash IV: 2×SSC, 0.025% Tween, prewarmed to 37° C. Buffer I: 4×SSC, 3% BSA, prewarmed to 37° C. Buffer II: 4×SSC, 1% BSA, prewarmed to 37° C. DAPI-stain: 50 ng/ml in 2×SSC (stored at 4° C. for up to 3 weeks), prewarmed to room temperature before use. Antifade solution: 2.3% DABCO (w/v) (Sigma D2522) dissolved in a solution consisting of 9:1 glycerin and 0.2 M Tris-Cl, pH 8.0. by warming to 70° C.

Procedure: After the hybridization, the slides were processed as described below. Since it is most important that slides do not dry at any point during the detection and washing steps, slides were kept in a floating box that contains a layer of moist paper towels in a covered water bath. Rubber cement was carefully removed. Coverslips were removed by agitating slides in wash I. Slides were washed 3×5 min in wash I, and then 3×5 min in wash II under gentle agitation. Thereafter, slides were incubated in wash III for 1 min and then in buffer I for 20 min, at 37° C. Slides were thereafter washed briefly in wash III.

All detection steps were performed at 37° C. in the (relative) dark. A dilution of avidin-FITC (1:400) in buffer II was prepared and 120 $\mu$l were added to the slides which were thereafter covered with 24×60 mm$^2$ coverslips. Slides were incubated at 37° C. for 30 min in dark environment in a moist chamber. For removal of coverslips, slides were dipped in a jar with buffer II and thereafter washed 3–5 min at 37° C. in buffer III. Meanwhile a dilution of biotinylated anti-avidin antibody (1:200) and mouse anti dig (1:500) in buffer II were prepared and 120 $\mu$l of each were added to the slides which were covered with coverslips as described. Slides were incubated for 30 min at 37° C. in the dark and then washed 3×5 min at 37° C. in wash III. Meanwhile a dilution of avidin-FITC (1:400) and goat anti mouse-Cy3 (1:400) were prepared and 120 $\mu$l of each were added to the slides, after which slides were treated as described above. If necessary, the Cy3 signal can be amplified as well by incubating the slides with an anti goat antibody conjugated to Cy3.

Counterstain with DAPI was performed for 5 min in 2×SSC. Propidium iodide can be an alternative or an additional DNA counterstain when the signal is solely detected with FITC in order to simultaneously visualize the chromosomes and the signal using a unspecific FITC filter or a double band pass filter for FITC and rhodamine. However, in any double label experiment using rhodamine, TRITC or Cy3, counterstaining with propidium iodide would negatively interfere with the signal detection due to overlapping spectra.

After DAPI counterstaining, slides were washed once in 2×SSC (2 min, room temperature), were applied 35 $\mu$l of antifade solution, and covered with clean 24×60 mm$^2$ coverslips avoiding formation of air bubbles. Slides were stored in the dark at 4° C. until subjected to spectral imaging.

EXAMPLE 2

IMPROVED FLUORESCENT IN SITU HYRIDIZATION (FISH) USING SPECTRACUBE™, A LINEAR COMBINATION ALGORITHM AND A CLASSIFICATION MAPPING ALGORITHM

Spectral bio-imaging using the SpectraCube™ system combined with the method of the present invention enhances the usefulness of FISH by allowing the simultaneous detection of a large number of probes, in a single measurement and with high accuracy. As a consequence, the efficiency and the reliability of detection of genetic abnormalities by FISH are greatly increased.

As detailed above, fluorescent in situ hybridization (FISH) plays an increasingly important role in many research and diagnostic areas. Since its first introduction in the 70's the FISH technique has made significant progress, enabling the detection and identification of single gene sequences, partial chromosome sequences and even whole chromosomes (i.e., chromosome painting). The many applications of FISH range from early detection of diseases, to prenatal diagnosis, aneusomy and others, to discover and perhaps in the future treat genetic diseases and abnormalities.

Due to the high sensitivity and selectivity of FISH, which is based on hybridization of homologous nucleic acid sequences, even short sequences as small as 1 kilobase (kb) can be observed (and this will probably improve with time to enable the detection of sequences as short as 15–30 base pairs and, as a consequence, of point mutations). FISH can be applied both to interphase and metaphase cells and even to whole tissues, enabling a broad range of applications both in the fields of cytogenetics and pathology. FISH is improving hand in hand with the improvements of DNA probes, fluorescent dyes (especially the introduction of combinatorial probes), fluorescence microscopy, high performance CCD cameras and imaging techniques.

The ability to detect many probes simultaneously has already been shown in the literature to make FISH an efficient diagnostic tool. However, the existing methods are cumbersome and difficult to use. As will be exemplified hereinbelow, the detection of many probes is greatly improved by the SpectraCube™ system combined with appropriate algorithms, because of its spectral resolution and sensitivity. To illustrate this capability, the reader is now referred to FIGS. 5a–c, which include an example of an interphase FISH measurement performed with chromosome 1 and chromosome 17 specific DNA probes tagged with the fluorophores Texas-Red and Rhodamine, respectively, whose fluorescence spectra are very similar. The chromosome 1 probe was a midsatellite probe for the subtelomeric region of the chromosome and was tagged with Texas-Red linked to the DNA probe via biotin post hybridization. The chromosome 17 probe was an α satellite probe for the centromeric region of the chromosome and was tagged with Rhodamine, linked to the second DNA probe via digoxigenin post hybridization. FIG. 5a shows the original image, the way it looks to the eye through the microscope; FIG. 5b shows the same sample, after being measured and processed by the SpectraCube™ system; and, FIG. 5c shows the fluorescence spectra of the Texas-Red (marked as T) and Rhodamine (marked as R) fluorophores.

As seen in FIG. 5c, the spectral peaks of Texas-Red and Rhodamine differ merely by 15 nm, and therefore it would be very difficult to distinguish between them using a filter-based system.

Looking at a color FISH image through a microscope as shown in FIG. 5a, the confidence level of recognizing the correct number of dots (marked 1–4) and of probe types appearing in the image is not particularly high. As shown in FIG. 5b, the SpectraCube™ system, on the other hand, taking advantage of the spectrum measured for each pixel, is able both to verify the existence of the dots, to count them exactly, and to discriminate between the different pairs with a high level of confidence, due to the small spectral difference between them. By artificial coloring of Texas-Red and Rhodamine fluorescence, as shown in FIG. 5c the location of probe specific fluorescence could be determined with high accuracy wherein dots 1 and 2 are of Texas-Red and dots 3 and 4 are of Rhodamine.

Figure 6A:
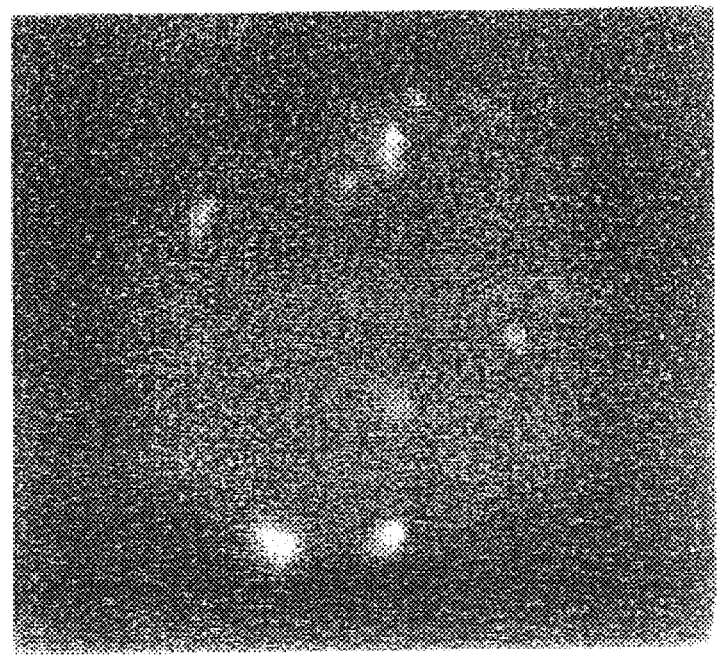
FIGS. 6a, 6b and 6c show interphase FISH performed with six different probes each labeled with a different fluorophore wherein (a) is an original image, the way it looks thorough a microscope, cells were counter stained with DAPI; (b) is the same sample, after being measured and processed by the method of the present invention; and (c) are the fluorescence spectra of the six fluorophores.
Figure 6B:
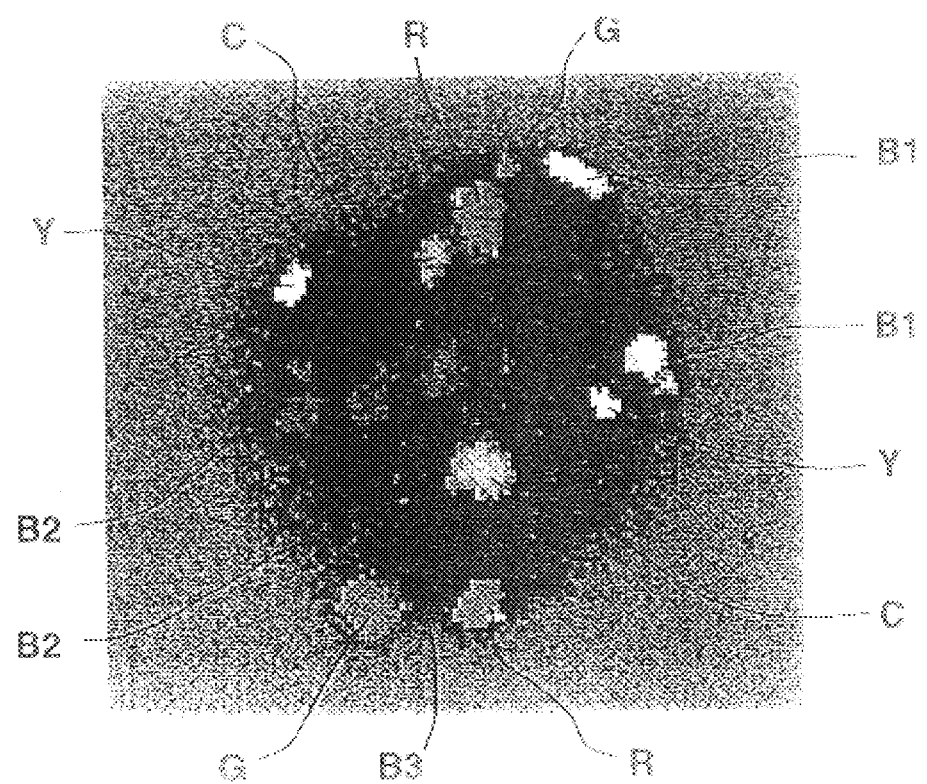

FIGS. 6a–b are an example of FISH measurement after hybridization of a nuclear DNA in interphase with six different probes. FIG. 6a shows the original image; FIG. 6b shows the SpectraCube™ measurement, spectral processing and artificial color display of all the detected pairs; and, FIG. 6c the spectra of the six fluorophores after hybridization (marked according to the chromosomes each of which labels: 1, 8, 10, 11, 17 and X), as detected through a triple dichroic filter using the SpectraCube™ system. (For details regarding flourophores, probes and chromosomes the reader is referred to the following description, Table 2 below and to Chroma Corp. Cat. No. 61502).

It is apparent from FIG. 6a, showing the original RGB image of the interphasic cell nucleus, that it is difficult to distinguish the colors from one another by eye or even by using a simple RGB color measurement. An experienced observer may, in the best case, detect three different colors of the six. FIG. 6b, however, shows the same sample shown in FIG. 6a, after processing the spectral data with proprietary classification algorithms for background subtraction and classification (see, details above), and the resulting dots have been highlighted with artificial colors as follows: brown—B1; cyan—C; blue—B2; yellow—Y; green—G; and red—R, while the background was given a black—B3, artificial color. As observed, it is possible to see all the six pairs of fluorophores and to easily differentiate among the pairs.

It should be further noted that one pair, the one highlighted in blue (B2), can hardly be noticed by eye, or by using a color camera; however, it is detected after applying a background subtraction algorithm on the spectral cube (compare FIGS. 6a with 6b).

The probes used were five α satellite probes for the centromeric regions of chromosomes 8, 10, 11, 17 and X, and a midsatellite probe for the subtelomeric region of chromosome 1. The fluorophores used to label each of the above chromosomes and the DAPI counter stain (backg.), their emission peak and artificial displayed color classification are summarized in Table 2.

Figure 6C:
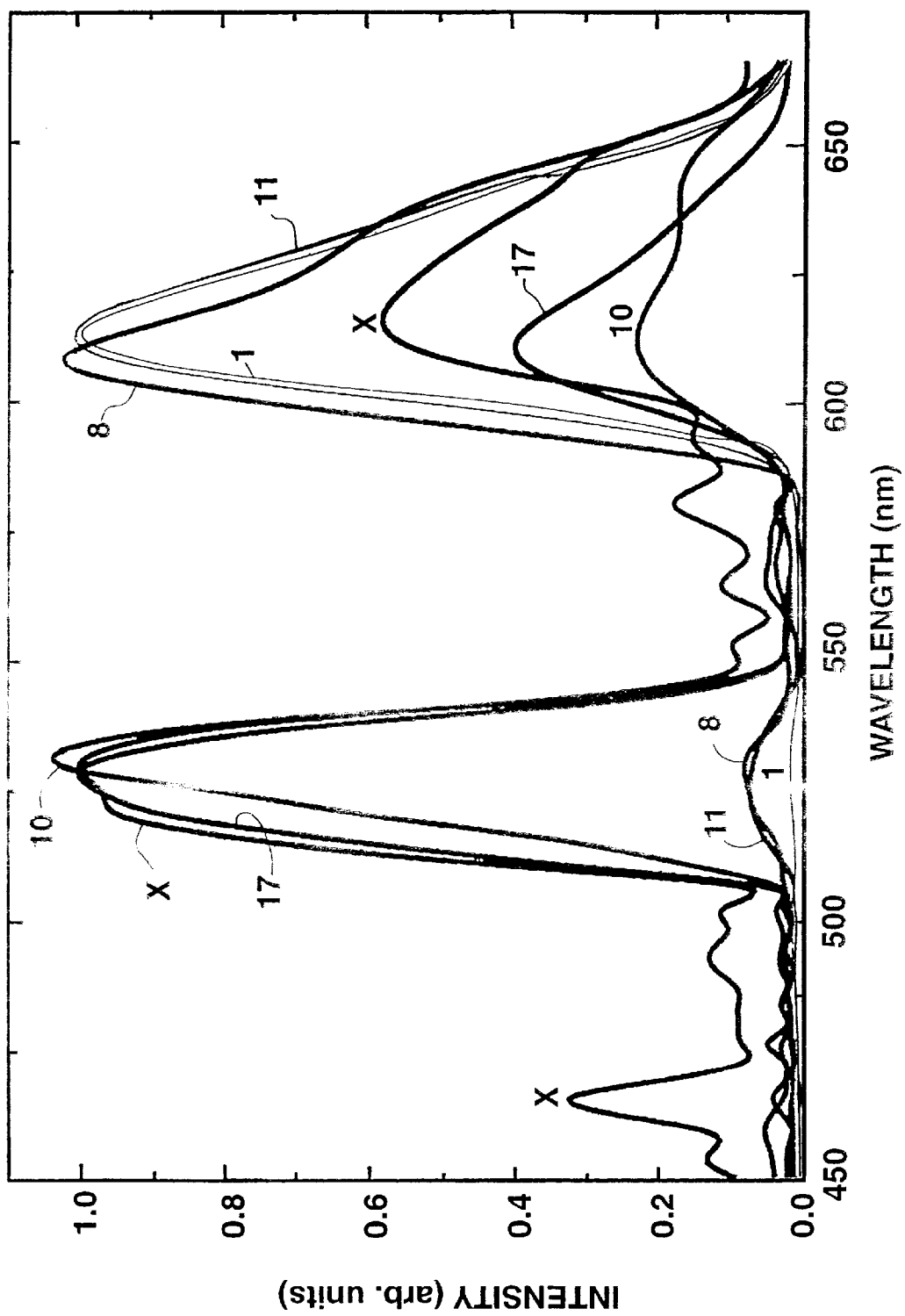
Figure 7A:
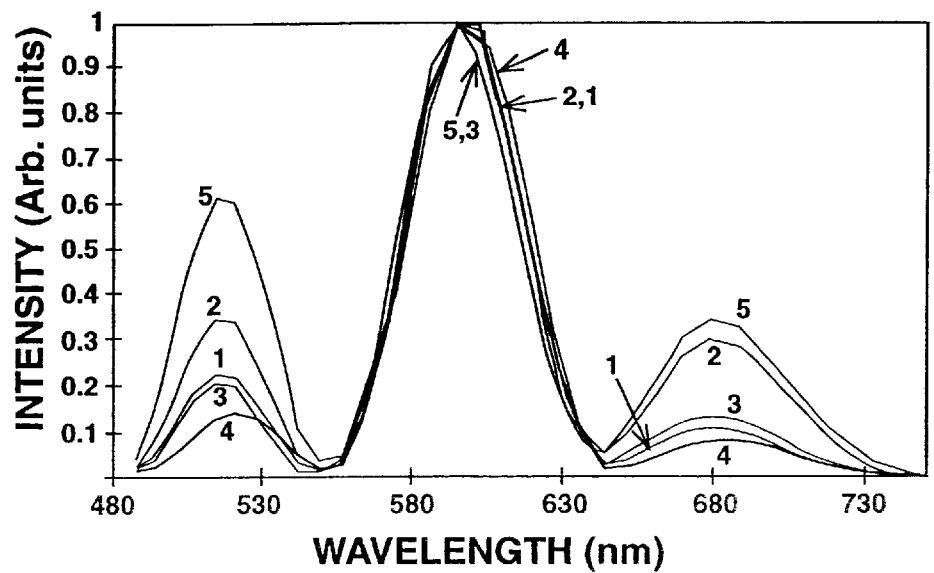
FIGS. 7a, 7b, 7c, 7d and 7e collectively show 24 normalized spectra of 24 pixels of the image of FIGS. 8a and 9a, each of the 24 pixels is derived from a different human chromosome (1–22, X and Y), each of the chromosomes was painted using a different chromosome paint as detailed in Tables 3 and 4 below.
Figure 7B:
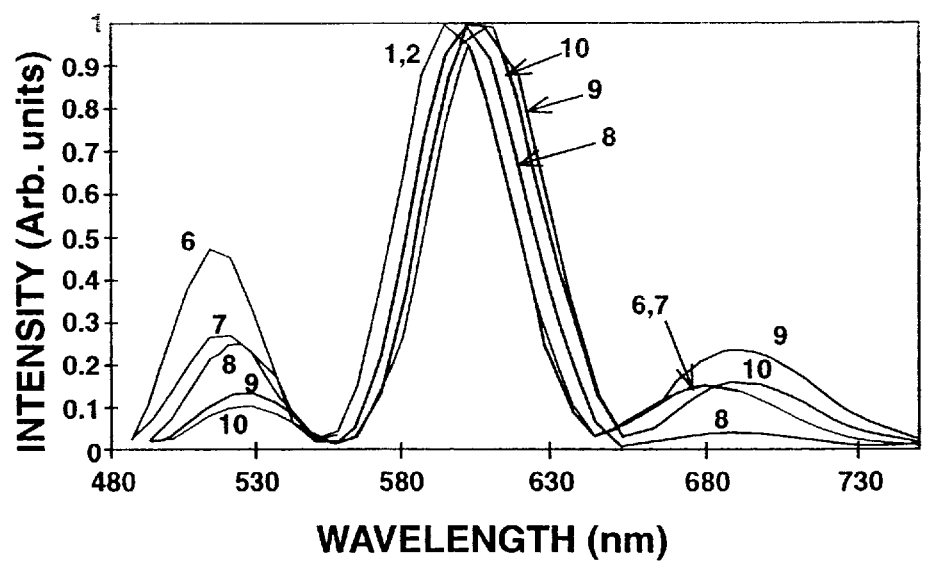
Figure 7C:
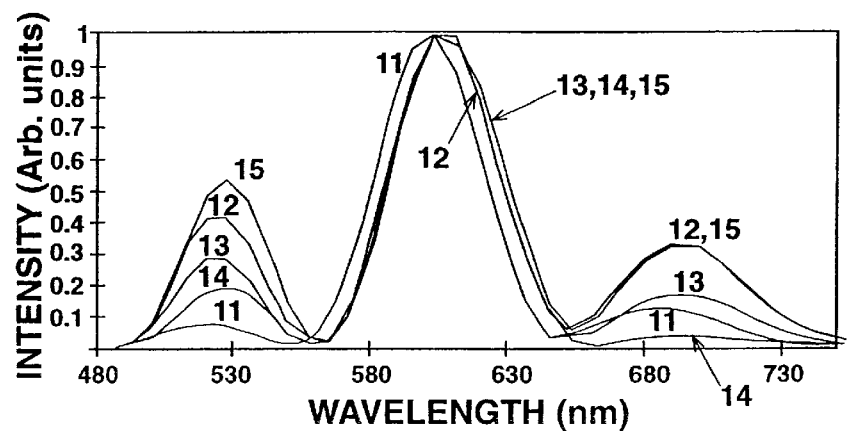
Figure 7D:
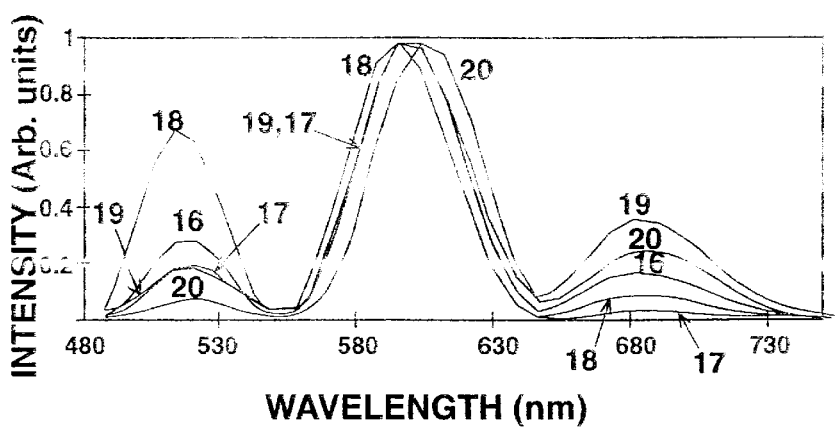
Figure 7E:
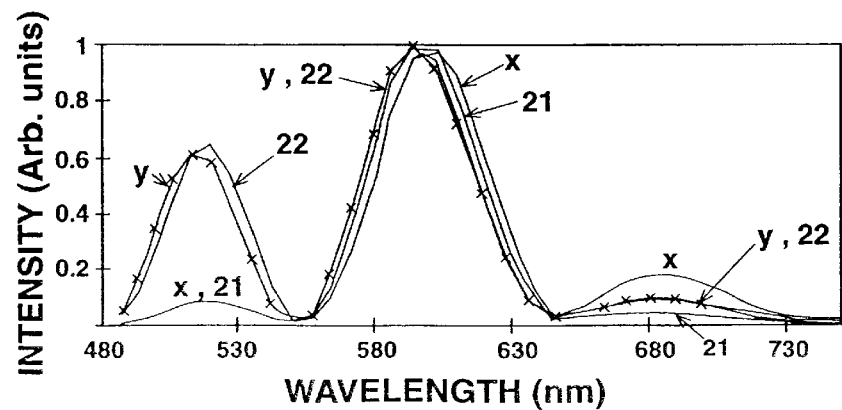

From the normalized spectral signatures of each of the six fluorophores shown in FIG. 6c, it is clear that a system based on filters measuring at a few relatively wide spectral ranges, is not able to differentiate reliably between the different probes species, because of the large overlap between the spectra. Such a system is more dependent on the absolute measurement of the intensity of each probe, and therefore it is more affected by background signals and noise. It should be further noted that spectral overlapping sometimes occurs also with auto-fluorescence originating from the cell itself. In this case too, the availability of spectral information for each pixel enables the elimination of the auto-fluorescence contribution, and yields more accurate results.

TABLE 2

| Chromosome | Fluorophore | Emission peak | Displayed color |
|---|---|---|---|
| 8 | SpectrumOrange ™[1] | 588 nm | Brown (B1) |
| 10 | SpectrumGreen ™[1] | 538 nm | Cyan (C) |
| x | Aqua[1] | 480 nm | Blue (B2) |
| 1 | Texas-Red[2] | 615 nm | Yellow (Y) |
| 17 | FITC[3] | 525 nm | Green (G) |
| 11 | Texas-Red[2] + FITC[3] | 615, 525 nm | Red (R1) |
| backg. | DAPI[4] | Black (B3) | |

[1]obtained as labeled deoxynucleotides from Vysis, Downers Grove, IL, U.S.;
[2]conjugated via anti-digoxigenin antibody to pre hybridized digoxigenin containing probes;
[3]fluorescein-5-iso-thiocyanate, conjugated via anti-biotin antibody to pre hybridized biotin containing probes;
[4]4',6-diamidino-2-phenylindole used for counter staining.

Having measured the full spectrum of each point on the image, may also help overcome specificity problems of the probes. In fact in some cases, a probe that matches a certain chromosome DNA sequence, has also a lower specificity to a different (usually similar) sequence, and it hybridizes with a lower probability to the second sequence too. This leads to the spurious appearance of too many probes of a certain type. However, the fluorescence spectrum in the second case is very slightly shifted with respect to the first one, due to a small change in the chemical environment of the probe. The SpectraCube™ system, thanks to its spectral resolution and sensitivity, may eliminate this artifact. A similar artifact exists for probes which are not washed out during sample preparation, and contribute to false positive diagnosis. The SpectraCube™ system combined with the method of the present invention, therefore, helps lowering the risk of wrong diagnosis.

Generalizing to a large number or similar dyes, the examples of FIGS. 5a–b and 6a–c show that it is possible to detect and distinguish a large number of probes, and, provided there are small spectral differences between them, the SpectraCube™ will detect and identify them in one measurement.

It is clear to one ordinarily skilled in the art that other and/or additional known and yet to be discovered or developed fluorophores and fluorophores combinations may be used in various FISH applications as detailed above to detect large number of loci simultaneously, to paint each chromosome of a karyotype in a distinguished color, etc. A list of flourophores used in state of the art cellular and molecular biology may be found in Kasten (1993) Introduction to fluorescent probes: Properties history and applications, in Fluorescent and luminescent probes for biological research, Mason Ed. Academic Press Limited, London, pp. 24–31. It is also clear to one ordinarily skilled in the art that other labeling techniques such as for example bioluminescent and chemoluminescent and also non-fluorescent labeling strategies may be similarly applied.

Thus, using the SpectraCube™ system for FISH analysis enjoys a major advantage as follows. The SpectraCube™ system, due to its high spectral resolution, enables simultaneous detection of numerous probes, whereas using conventional means to perform FISH (e.g., using a fluorescence microscope) limits the number of probes to be used in a single hybridization to two—four probes. Therefore, employing the SpectraCube™ system for FISH analyses save effort and time. Furthermore, while employing the SpectraCube™ system for FISH analysis a smaller number of cells are required for full analysis, an important feature in cases where the number of cells to be analyzed is limited.

EXAMPLE 3

SIMULTANEOUS VISUALIZATION OF ALL HUMAN CHROMOSOMES IN DIFFERENT COLORS USING FLUORESCENT IN SITU HYBRIDIZATION, SPECTRAL BIO-IMAGING AND RGB ALGORITHM

The emergence of multicolor FISH has broadened the applications of molecular cytogenetics in basic research and genetic diagnosis. All existing multicolor FISH techniques require the use of fluorescent probes whose emission spectra can be separated with optical filters [Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. This requirement limits the number of dyes which can be distinguished in a given sample. According to the present invention provided is a novel approach for FISH, employing the SpectraCube™ system and the method of the present invention to measure and analyze multiple spectrally overlapping labeled probes (single and combinatorial). In this Example, spectral bio-imaging which, as delineated above, is a combination of Fourier spectroscopy, CCD-imaging and optical microscopy enabling the measurement of definitive spectral data simultaneously at all points of a biological sample, was used to visualize hybridization based multicolor appearance of all (i.e., 24) types of human chromosomes and to generate a color map of the human karyotype.

For this purpose, 24 chromosome paints (1 through 22, X and Y, Table 4) each labeled with a different combination of five or less different flourophores according to the combinatorial hybridization approach (a through e, Table 3), (see Table 3 for the different fluorophores and their spectral characteristics and Table 4 for the assignment of the fluorophores listed in Table 3 to obtain the 24 chromosome paints), were simultaneously hybridized with human mitotic chromosome spreads of two non-related male white blood cells, prepared for hybridization essentially as described in Ried et al. [Ried et al., (1992) Simultaneous visualization of seven different DNA probes by in situ hybridization using combinatorial fluorescence and digital imaging microscopy. Proc. Natl. Acad. Sci. USA 89, 1388–1392]. Hybridized chromosomes were viewed through an inverted fluorescence microscope connected to the SpectraCube™ System and were analyzed.

TABLE 3

| Fluorophore | Symbol | Excitation (nm) |
|---|---|---|
| FITC or Spectrum Green | a | 475–495 |
| CY2 ™[1] | b | 475–495 |
| CY3 ™[1] | c | 540–570 |
| Texas-Red | d | 540–570 |
| CY5 ™[1] | e | 630–670 |

[1]from Amersham

TABLE 4

| Chromosome | Chromosome paint | Flourophores |
|---|---|---|
| human chromosome 1 | 1 | b,c,d |
| human chromosome 2 | 2 | a,d,e |
| human chromosome 3 | 3 | a,c,e |
| human chromosome 4 | 4 | a,c,d |
| human chromosome 5 | 5 | a,b,e |
| human chromosome 6 | 6 | a,b,d |
| human chromosome 7 | 7 | b,c,e |
| human chromosome 8 | 8 | a,b,c |
| human chromosome 9 | 9 | d,e |
| human chromosome 10 | 10 | c,e |
| human chromosome 11 | 11 | c,d |
| human chromosome 12 | 12 | b,e |
| human chromosome 13 | 13 | b,d |
| human chromosome 14 | 14 | b,c |
| human chromosome 15 | 15 | a,e |
| human chromosome 16 | 16 | a,d |
| human chromosome 17 | 17 | a,c |
| human chromosome 18 | 18 | a,b |
| human chromosome 19 | 19 | e |
| human chromosome 20 | 20 | d |
| human chromosome 21 | 21 | c |
| human chromosome 22 | 22 | b |

TABLE 4-continued

| Chromosome | Chromosome paint | Flourophores |
| --- | --- | --- |
| human chromosome X | X | c,d,e |
| human chromosome Y | Y | a |

With reference now to FIGS. 7a–e, 8a–b and 9a–b. FIGS. 7a–e show normalized spectra of 24 individual pixels, each of a different type of human chromosome (1–22, X and Y). Numbers 1–22 and letters X and Y, refer to the chromosome type of which each of the spectra presented were derived. Note that the spectrum obtained from each of the 24 human chromosomes, as shown in FIGS. 7a–e, differ from all other spectra. This difference may be large (compare, for example, the Ca. 530 nm emission peak of chromosome 15 and 11 in FIG. 7c) or small (compare, for example, the Ca. 530 nm emission peak of chromosome 22 and Y in FIG. 7e) and, in some spectral ranges may even disappear (compare, for example, the Ca. 680 nm emission peak of chromosome 22 and Y in FIG. 7e). Nevertheless, as further shown in FIGS. 7a–e, even a minor difference between very similar spectra can be detected using the SpectraCube™ system and the method of the present invention. It is however clear from this description that the ability of the method of the present invention to detect differences among spectra, to a large extent depends upon appropriate fluorophores and fluorophore combinations selected, yet, as will be appreciated by one ordinarily skilled in the art and even by one expert in the art, the ability herein demonstrated, far beyond exceeds that of any prior art cytogenetic technique.

Figure 8A:
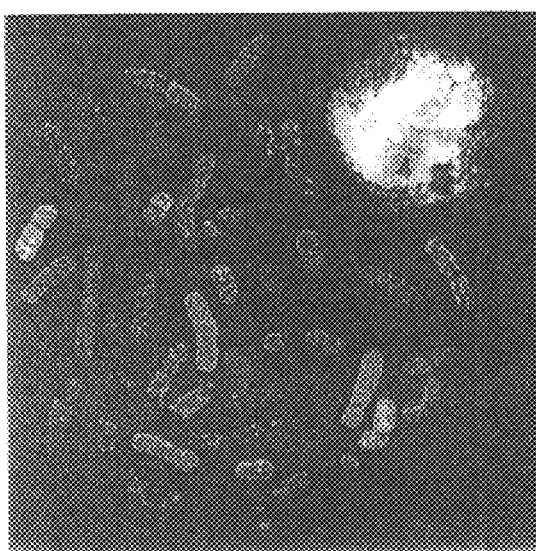
FIGS. 8a and 8b are an RGB image and a color karyotype (presented in black and white) derived from it, respectively, of the 24 human male chromosomes (1–22, X and Y) each of the chromosomes was painted using a different chromosome paint as detailed in Tables 3 and 4 below, obtained using the method of the present invention.
Figure 8B:
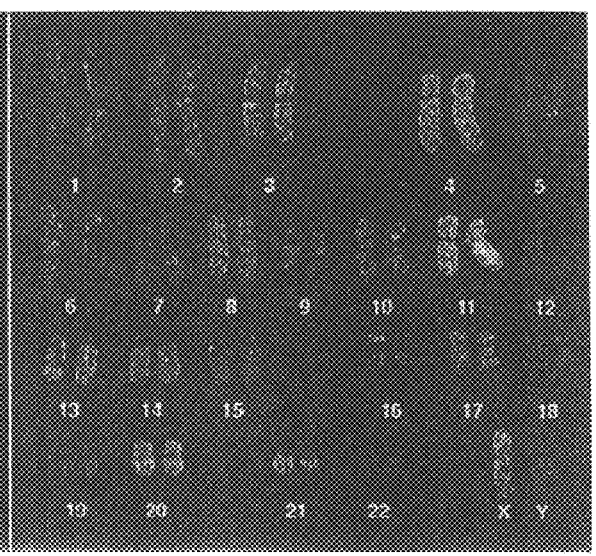

FIG. 8a shows an RGB image of thus described painted human chromosomes, whereas FIG. 8b shows a color human karyotype derived from the painted chromosomes of FIG. 8a. Since it is not possible to literally describe 24 different colors, colored FIGS. 9a and 9b which are otherwise identical to black and white FIGS. 8a and 8b, respectively, are also enclosed. Note that each of the chromosome pairs is painted in a different color and that the color karyotype (FIG. 9b) is readily derived from the color image (FIG. 9a).

Figure 9A:
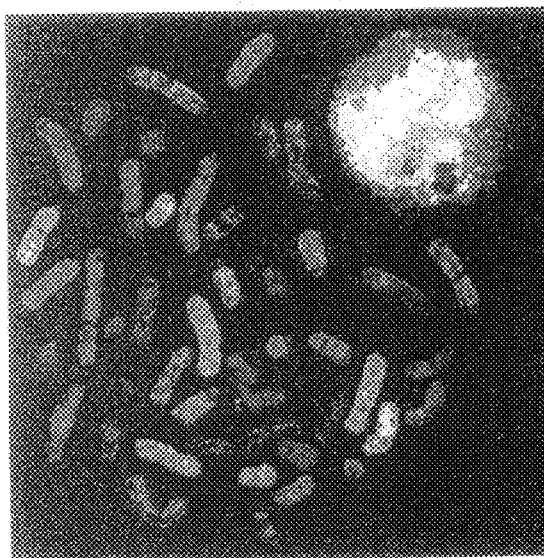
FIGS. 9a and 9b are color presentations of FIGS. 8a and 8b, respectively.

The algorithm used to obtain and display the image of FIGS. 8a and 9a was an RGB algorithm as described above and as exemplified in FIG. 4, wherein R=640–740 nm; G=550–640; and, B=530–550 nm. However to obtain a more unified image in terms of intensities, a special modification of the RGB values obtained was exercised. This modification, known in the color imaging art as "contrast stretching", [see for example, ENVI™ User's guide, The environment for visualizing images Version 1.1 July 1994 Edition, BSC limited Liability Company] includes (a) determining the distribution of each of the RGB values; (b) defining a look-up table for maximizing differences among intensities within the determined distribution; and (c) displaying the modified RGB image, now having a maximal color variation for each original different spectrum. This simple modification of the original RGB image is actually a limited version of a classification algorithm as described above.

With reference now to FIGS. 10a–d and 11a–d. FIG. 10a shows an RGB image of painted human chromosomes of another individual, whereas FIG. 10b shows a color human karyotype derived from the painted chromosomes of FIG. 10a. FIGS. 10c and 10d show a classification map of the painted human chromosomes and derived karyotype of FIGS. 10a and 10b, respectively. Since it is very difficult to literally describe 48 different colors and shades, colored FIGS. 11a–d which are otherwise identical to black and white FIGS. 10a–d, respectively, are also enclosed. Note that each of the chromosome pairs is painted in a different color and that the color karyotypes are readily derived from the color images, both for RGB and classification mapping algorithms.

In this Example, the use of 24 different single and combinatorial probes combined from five different basic fluorophores as prepared according to the combinatorial hybridization approach (a through e, Table 3) was demonstrated for human color chromosome karyotyping. Nevertheless, some other species have a greater number of chromosomes, which perhaps requires the use of more complicated combinatorial probes combined of more basic fluorophores. Yet, it should be noted that chromosomes, including human chromosomes, can also be classified to size groups, which, for some applications minimize the need for as many different colors since chromosomes belonging to different size groups may be similarly colored yet easily recognized according to their relative size. This could be achieved by manual inspection, or alternatively using any morphological algorithm. It is however clear to one ordinarily skilled in the art that other algorithms may equivalently or better suit the purpose of displaying similar images.

As detailed and exemplified hereinabove a principal component analysis may also be found suitable, wherein each meaningful component or combinations thereof will be attributed a different predetermined artificial color. Yet, additional algorithms capable of differentiating similar spectra and attributing a different predetermined artificial color (or pseudo color) to pixels having a different spectrum may also be found suitable for color karyotyping according to the method of the present invention.

EXAMPLE 4

DETECTION OF MULTIPLE CHROMOSOME TRANSLOCATIONS IN BREAST CANCER CELLS

As demonstrated, the method of the present invention can provide a complete color karyotype of normal blood cells. In many cases conventional karyotyping (e.g., using G-banding or R-banding techniques) is used to detect chromosomal aberrations such as translocations associated with genetic disorders (e.g., 21q22 trisomy in Down's syndrome, chromosome 18 (or a fragment thereof) trisomy and chromosome 13 (or a fragment thereof) trisomy) or malignancies (e.g., a translocation between the distal ends of chromosomes 9 and 22 in leukocytes from patients with chronic myelogenous leukemia and, a chromosomes 8 and 14 translocation in lymphocytes of patients with Burkitt's lymphoma). In this Example the capabilities of the SpectraCube™ system combined with the method of the present invention to detect multiple chromosome translocations in breast cancer cells is demonstrated.

Figure 9B:
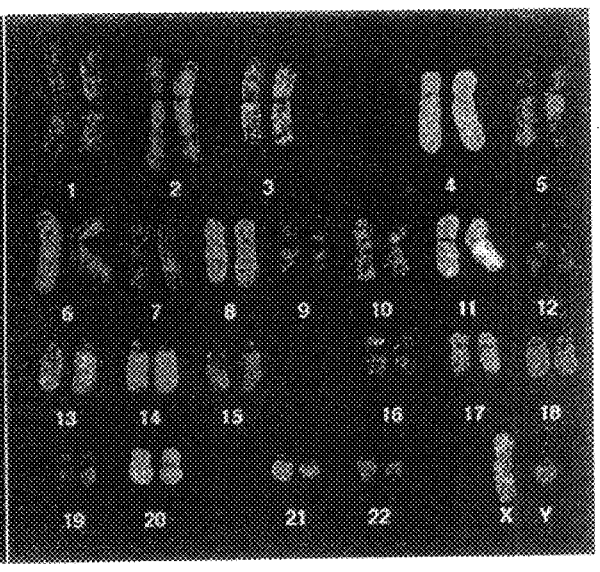
Figure 11A:
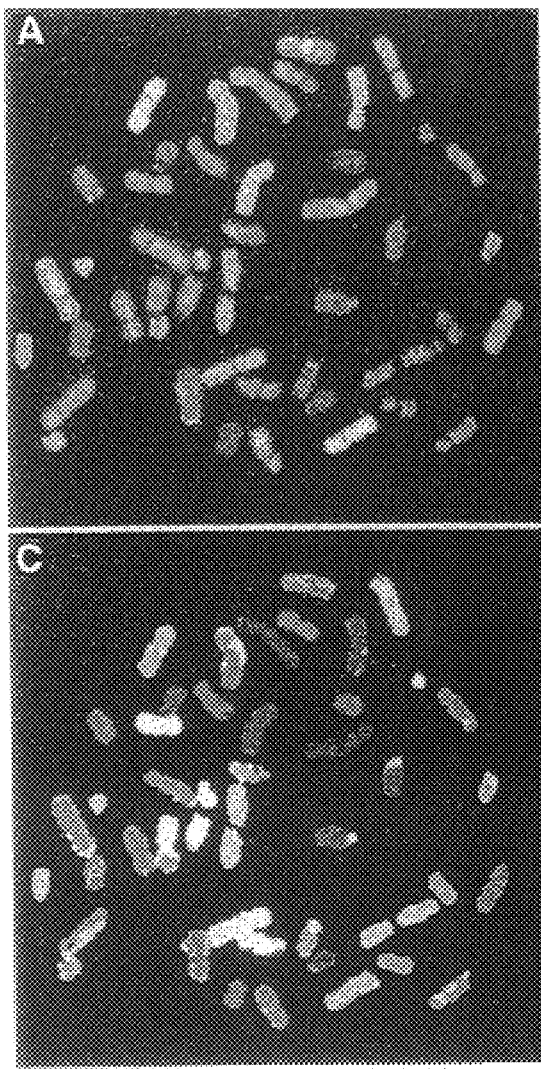
FIGS. 11a, 11b, 11c and 11d are color presentations of FIGS. 10a–d, respectively.
Figure 11B:
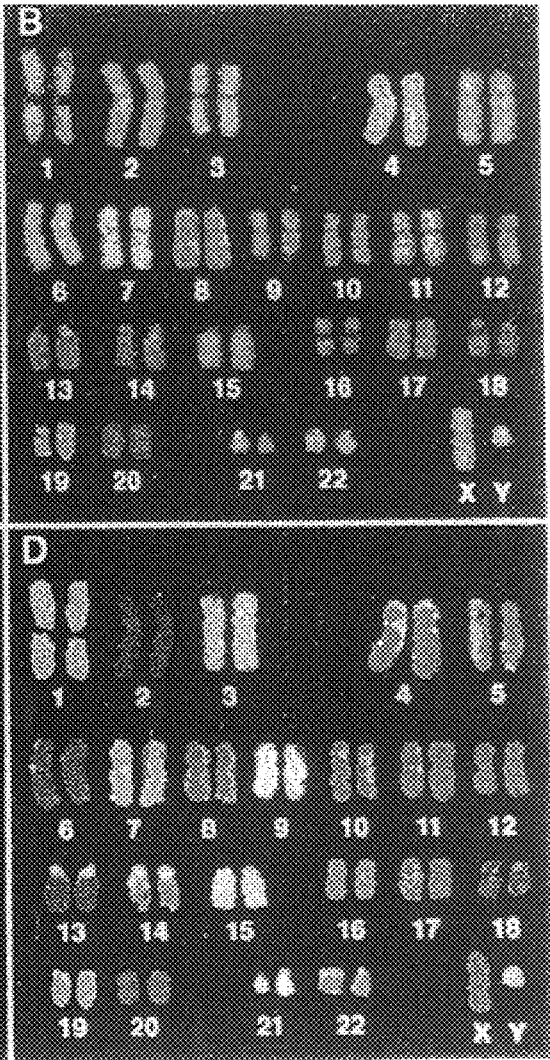
Figure 11C:
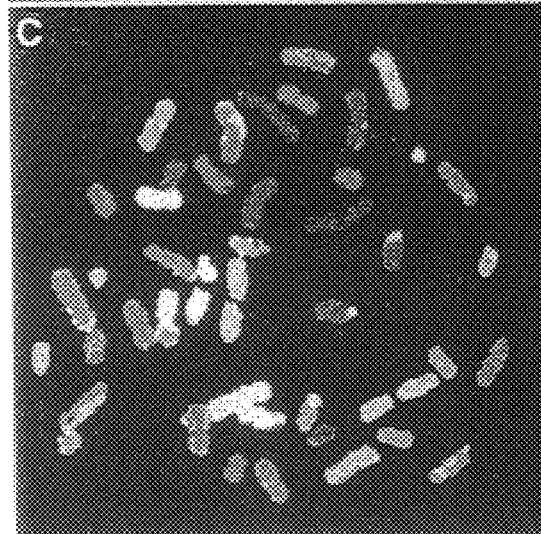
Figure 11D:
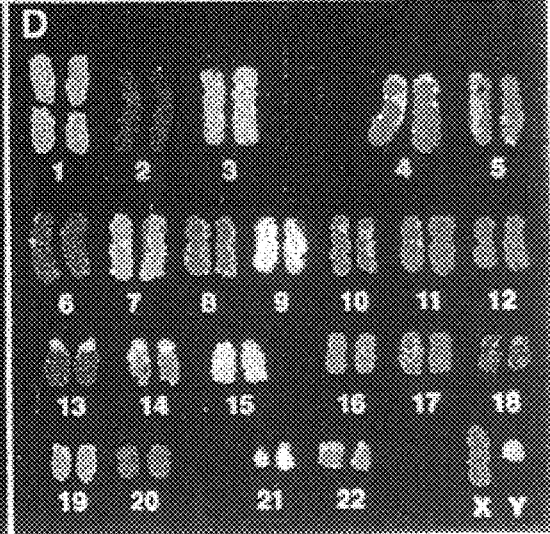
Figure 12A:
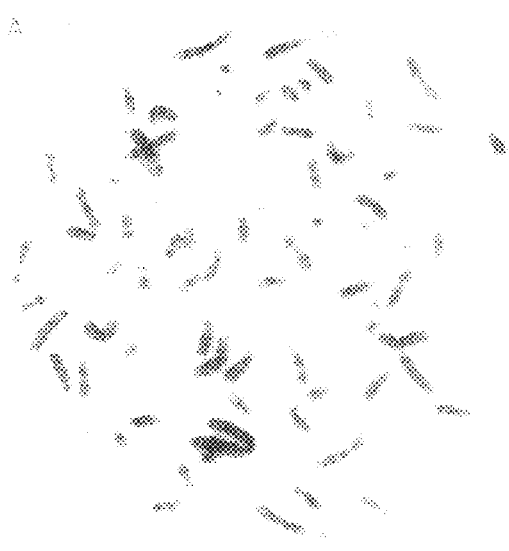
Figure 12B:
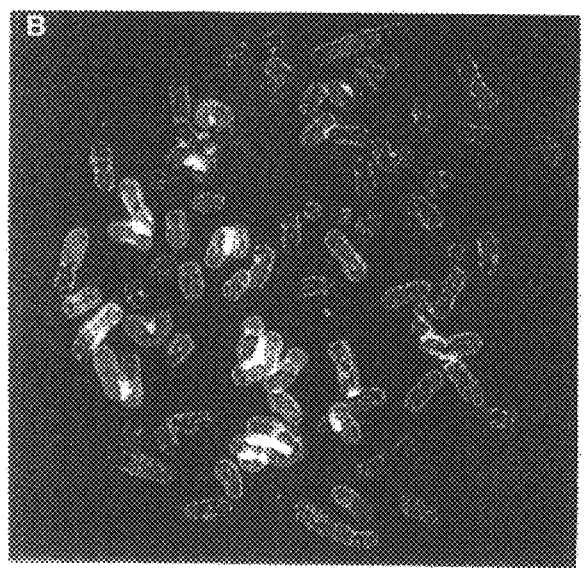
Figure 13A:
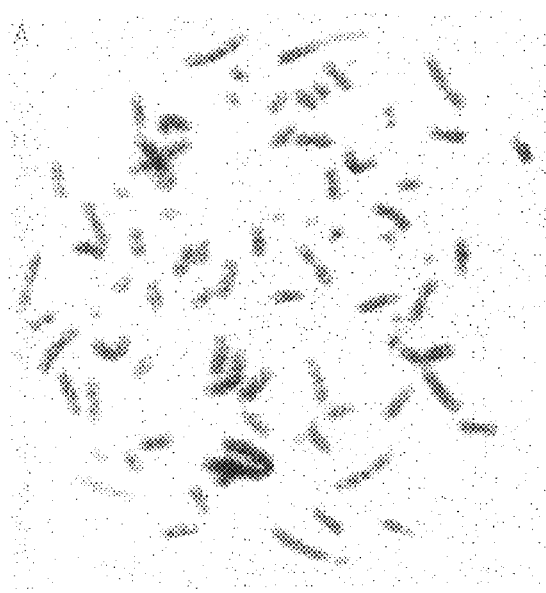
FIGS. 13a–e are original, more clear presentations and color presentations of FIGS. 12a–e.
Figure 13B:
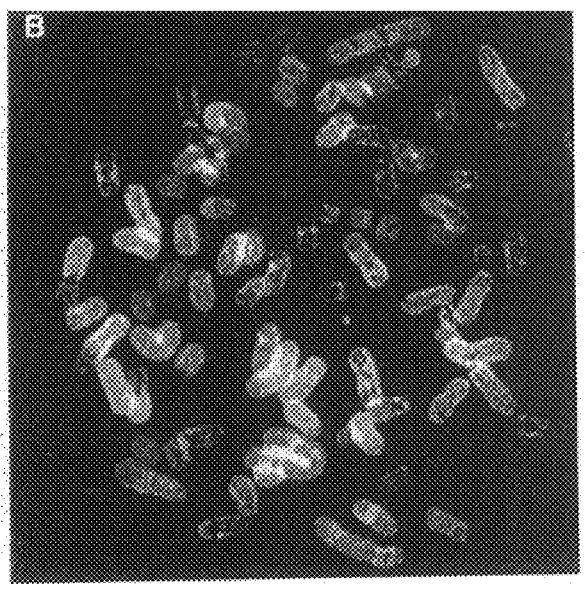
Figure 13C:
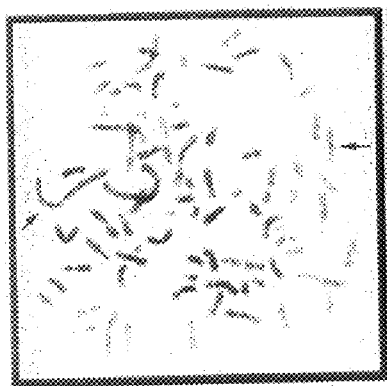
Figure 13D:
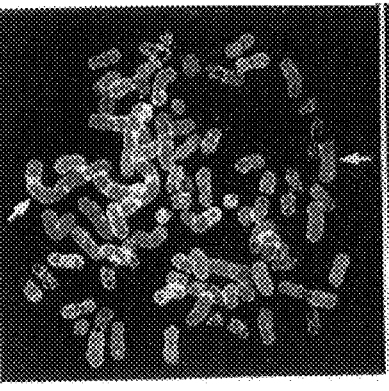
Figure 13E:
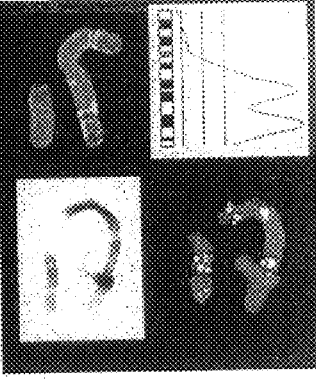
Figure 14:
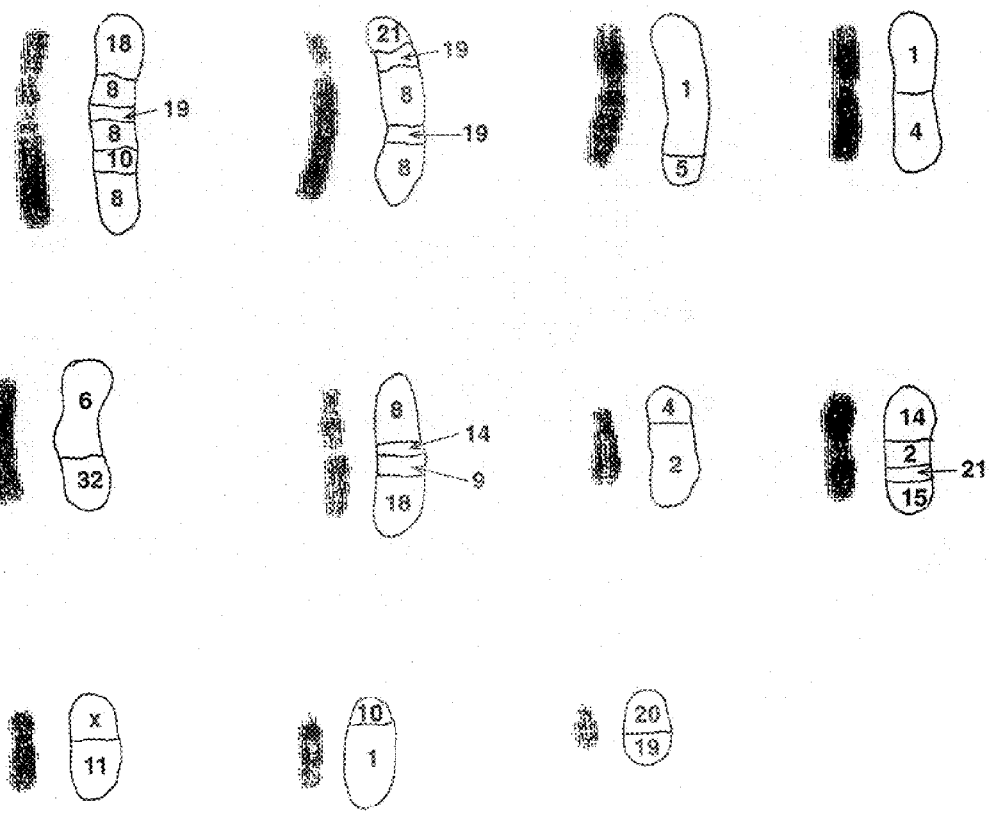
FIG. 14 is a comparative presentation of the DAPI R-banded and an interpreted outline of the painted translocated chromosomes presented in FIGS. 13a (left) and 13b (right), respectively, as was determined from FIG. 13b and interpreted using the color karyotype shown in FIG. 9b.
Figure 15:
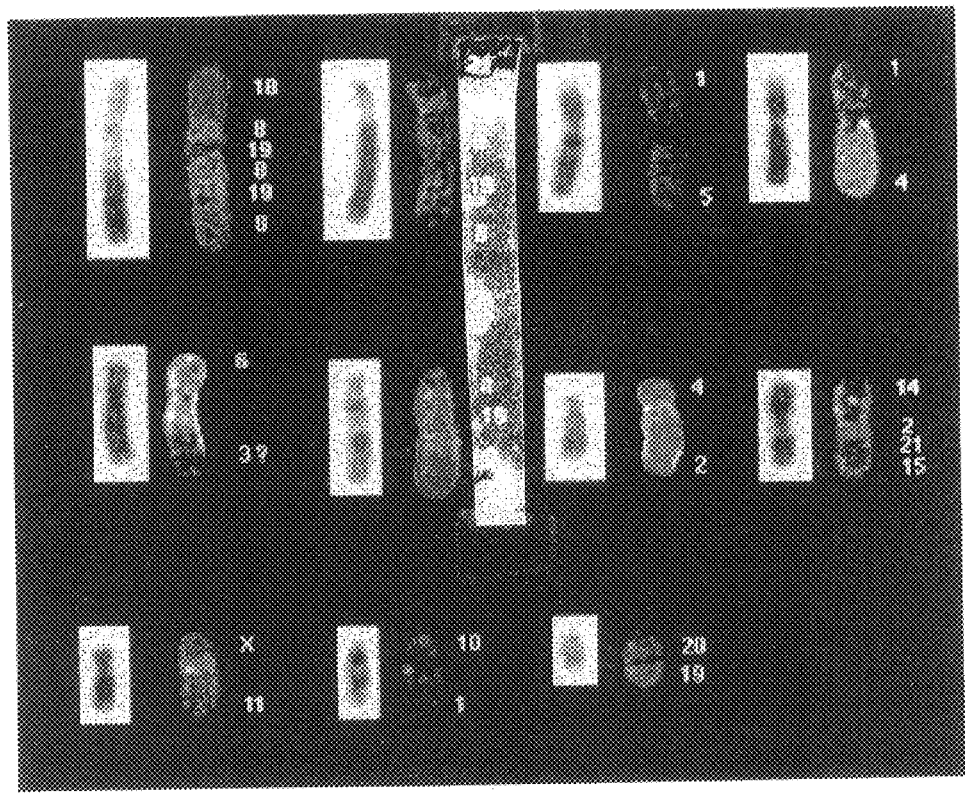
FIG. 15 is a color presentation of FIG. 14.

With reference now to FIGS. 12a–e, 13a–e 14 and 15. Chromosome spreads of breast cancer cell line SKBR3 were hybridized with the 24 chromosome paints (1 through 22, X and Y) as detailed in tables 3 and 4 above and were spectrally imaged as detailed under Example 2 above. FIGS. 12a and 13a and FIGS. 12c and 12d show DAPI R-banding of two chromosome spreads as was photographed using a conventional fluorescence microscope (12a, 13a) and as was imaged using the SpectraCube™ system with a DAPI filter (i.e., DAPI band pass filter cube) (12c, 13c). It will be appreciated that although the resulting karyotype as depicted from these Figures is abnormal to a large extent, it is impossible to identify specific translocations of chromosomes. FIGS. 12b and 13b and FIGS. 12d and 13d show (in black and white and color, respectively) RGB images of the same spreads as was obtained using the SpectraCube™ system and the method of the present invention. When compared with FIGS. 9a–b, presenting a normal human karyotype derived under otherwise identical experimental conditions, it is apparent that many of the aberrations containing chromosomes shown in FIGS. 12b and 13b contain parts of various normal human chromosomes. The translocated chromosomes (right) of FIGS. 12b and 13b, along with the R-banded chromosomes (left) are shown in FIGS. 14 and 15. Note that some of the translocated chromosomes shown in FIGS. 14 and 15 include fragments originated from two, three and even four different chromosomes. Further note that large stretches of chromosomal material is painted with the chromosome 8 paint, suggesting increased copy number for this chromosome.

With reference now to FIGS. 12e and 13e, increased copy numbers for chromosome 8q was confirmed using comparative genomic hybridization (CGH) [see, A. Kallioniemi et al., Science 258, 818 (1992); and du-Manoir et al. (1993) Detection of complete and partial chromosome gains and losses by comparative genomic in situ hybridization. Hum. Genet. 90, 590–610] with DNA extracted from this cell line (upper part of the Figures). Dual-color FISH with a painting probe for chromosome 8 (in blue) and a cosmid probe for the c-myc oncogene (in red) also confirmed the structure of the marker chromosome (lower part of the Figures). Please note the discrete excursion of the profile at chromosome band 8q24 the map position of the c-myc oncogene.

Since specific chromosome translocations and other chromosomal aberrations (e.g., gene amplification) were previously associated with early or stage specific malignancies and, since the method of the present invention tremendously increases the ability to detect and characterize such translocations and other aberrations, the ability of early detection and stage classification of malignancies exercising the method of the present invention will be benefited. Furthermore, using the method of the present invention will enable to establish yet new chromosome specific aberrations (e.g., translocations) recurrently associated with specific malignancies and eventually to provide a comprehensive guide for such translocations. In addition, such recurrent aberrations may lead to the isolation of genes that by being activated or alternatively inactivated are associated with the malignant processes.

In this context it is important to notice that the fluorophores employed in this and the former Example 2 (as listed in Table 3 and shown in FIGS. 7a–c) collectively emit in the 480–730 nm range. Thus DAPI can be simultaneously used for counter staining since its emission is in the blue, well below this spectral range. Thus, as shown in FIGS. 12a–b, 13a–b, 14 and 15, it is possible to simultaneously observe the very same chromosome spreads using the conventional monochromatic R-banding approach and the multi-color approach of the present invention. It is clear that the SpectraCube™ system is capable of providing a conventional DAPI R-banding image by limiting the examined spectral range to blue. Thus, for a comparative purpose a single chromosome spread may be viewed using the SpectraCube™ system and the method of the present invention as a DAPI R-banded karyotype as well as a color karyotype. Hence, when chromosome translocation events are studied according to the method of the present invention the DAPI R-banded karyotype can provide additional information and to precisely point out which region(s) (i.e., bands) of any specific chromosome are involved in a specific translocation event.

EXAMPLE 5

THE POTENTIAL OF SPECTRAL KARYOTYPING AS A SCREENING METHOD FOR CHROMOSOMAL ABERRATIONS

The potential of spectral karyotyping as a screening method for chromosomal aberrations was explored by analyzing five clinical samples provided by different laboratories. All samples were previously studied by conventional banding methods and/or conventional FISH with one or few individual chromosome painting probes. Spectral karyotyping was performed without prior knowledge of the chromosomal aberrations. In all cases G-banding and spectral karyotyping revealed consistent results. Examples are presented in FIGS. 16a–b (black and white) and 17a–b (color). In some cases, Giemsa-banding was not sufficient to entirely interpret the chromosomal aberrations. In these cases, the diagnosis of chromosomal aberrations by spectral karyotyping was confirmed using conventional dual-color FISH-analysis.

Figure 16A:
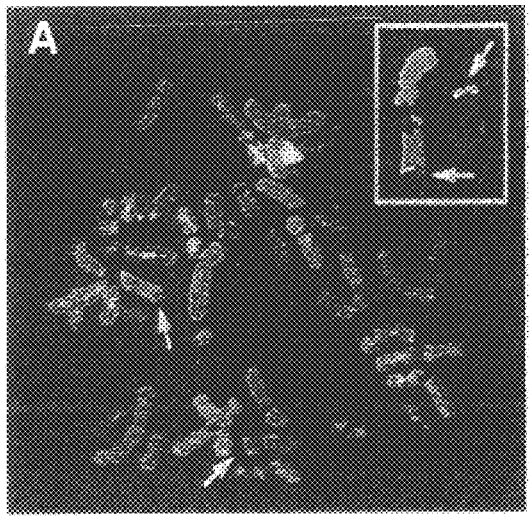
FIGS. 16a and 16b are (a) a RGB image of a chromosome spread having a translocation t(1;11)(q44;p15.3), the insert is a spectral-based classification of the translocated chromosomes, wherein chromosome 1 material is artificially colored in yellow and chromosome 11 material, in blue; (b) an RGB image of a translocation chromosome (translocation of a segment of chromosome 4 to chromosome 12) from a metaphase spread after spectral karyotyping according to the method of the present invention (right upper row) and the resulting artificial color image after applying a classification mapping algorithm (left upper row), and (b) a G-banding analysis (insert) and conventional dual-color FISH with painting probes for chromosome 4 (green) and 12 (red)

With reference now to FIGS. 16a and 17a, the smallest aberration analyzed was a translocation t(1;11)(q44;p15.3). The chromosomes were prepared from peripheral blood lymphocytes of a father of a child with mental retardation. The fragment that was translocated to chromosome 1 could be identified as chromosome 11 material (as indicated by an arrow). This translocation was reciprocal because a small fragment that corresponds to chromosome 1 was detected on the short arm of chromosome 11. The insert displays the result of a spectral-based classification of the translocated chromosomes, wherein chromosome 1 material is artificially colored in yellow and chromosome 11 material, in blue. The translocation segments on chromosomes 1 and 11 were confirmed using sub-telomere specific cosmid probes for chromosomes 1q and 1p (not shown).

Figure 16B:
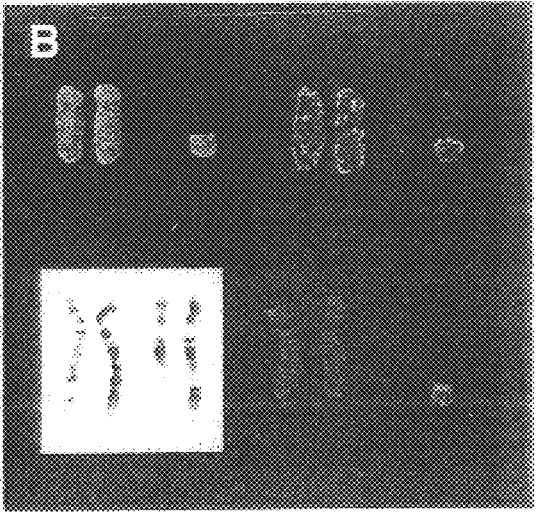

With reference now to FIGS. 16b and 17b. In another case, G-banding analysis suggested a translocation of a segment of chromosome 4 to chromosome 12. Spectral karyotyping unambiguously identified the origin of the additional chromosomal material as being derived from chromosome 4. Upper row of FIGS. 16b and 17b display an RGB image of the translocation chromosomes from a metaphase spread after spectral karyotyping according to the method of the present invention (right) and the resulting artificial color image after applying a classification mapping algorithm (left). Lower row of FIGS. 16b and 17b display a G-banding analysis (insert) and conventional dual-color FISH with painting probes for chromosome 4 (green) and 12 (red) which confirmed the unbalanced translocation as revealed by the method of the present invention.

Other cases not presented pictorially include (i) the diagnosis of a translocation t(8;13)(q24.1;q34); (ii) the diagnosis of a Klinefelter syndrome (karyotype 47, XXY); and (iii) the identification of the extra material that was present on a previously unidentified marker chromosome Xp+ was shown to be derived from the X-chromosome after spectral karyotyping.

EXAMPLE 6

THE USE OF THE METHOD OF THE PRESENT INVENTION FOR COMPARATIVE CYTOGENETICS

Figure 18:
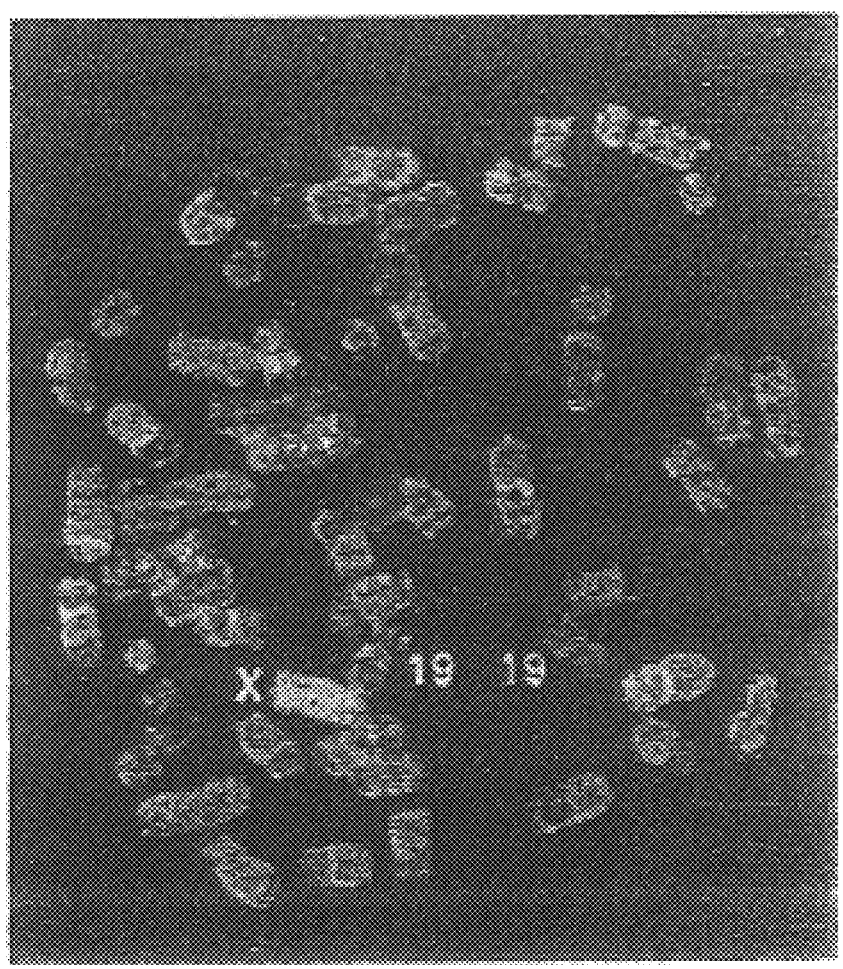
FIG. 18 is a multicolor spectral karyotype of the gibbon species *Hylobates concolor* after hybridization with human chromosome painting probes.
Figure 19:
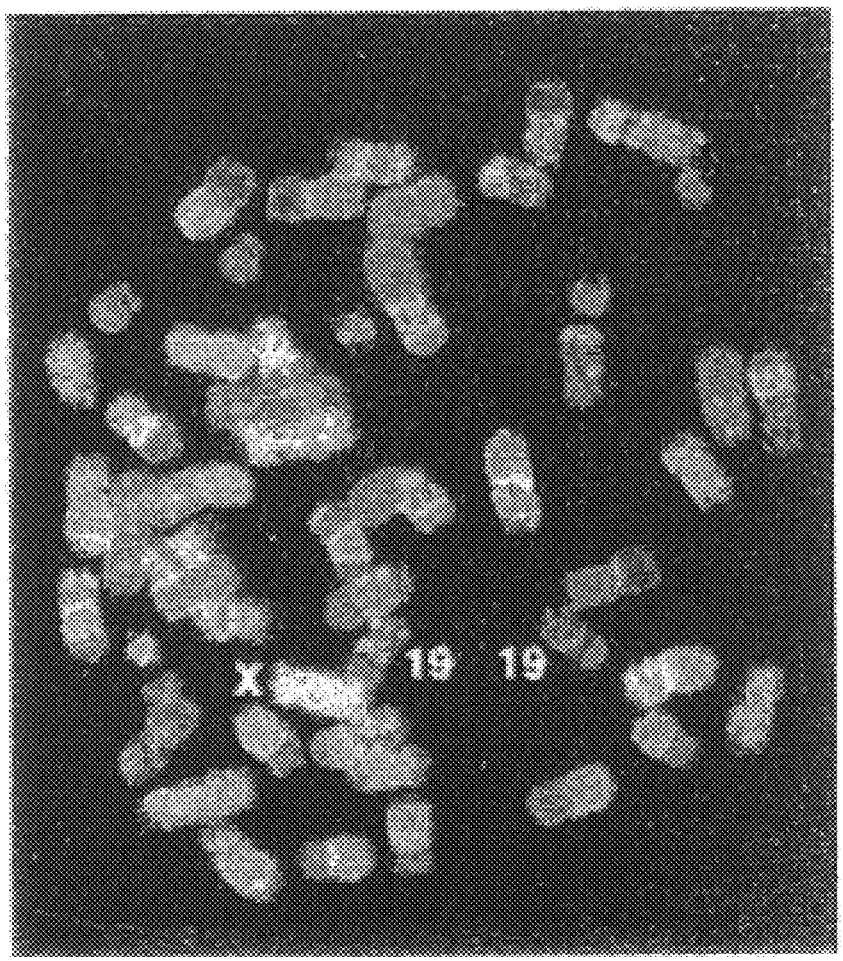
FIG. 19 is a color presentation of FIG. 18.

In addition to diagnostic applications in clinical and cancer cytogenetics as described above in examples 3 and 4, spectral karyotyping according to the method of the present invention is a versatile research tool for comparative cytogenetics [see, J. Weinberg and R. Stanyon (1995) Current opinion in genetics and development 5, 792–797]. Rearrangements which changed chromosome morphology during evolution can readily be visualized. For example, with reference now to FIGS. 18 and 19, using the human chromosome painting probes of Example 2, it was possible to reconstruct the highly rearranged karyotype of a gibbon species in a single hybridization. Thus, FIGS. 18 and 19 present a spectral karyotype of the gibbon species *Hylobates concolor* after hybridization with human painting probes. Note that the gibbon X-chromosome is entirely painted with the human X-chromosome. Most of the autosomes e.g., chromosomes 19, reveal a banding pattern reflecting multiple evolutionary chromosomal rearrangements.

Spectral karyotyping of the evolutionary rearranged chromosomes was consistent with results from previously performed conventional FISH-experiments and banding analysis [see, U. Koehler, F. Bigoni, J. Wienberg and R. Stanyon. Genomics 30, 287 (1995); and P. van Tuinen and D. H. Ledbetter. Am. J. Phys. Anthropol. 61, 453 (1983)]

EXAMPLE 7

ADDITIONAL FISH APPLICATIONS

From the above descriptions it is clear that (1) several types of probes may be used for FISH, these include loci specific probes, groups of chromosome fragments, chromosome paints and whole genomes (e.g., for CGH analysis); (2) the analyzed chromosomes may be during interphase, mitosis or meiosis; and, (3) dozens of probes of all types may be simultaneously hybridized to the chromosomes and, provided that each of the probes has a somewhat different spectrum, the SpectraCube™ system as used according to the method of the present invention can spectrally detect each of the probes and present its spatial arrangement by attributing pixels presenting each of the spectra an RGB color (i.e., pseudocolor) or a predetermined artificial color using any suitable classification algorithm (e.g., classification mapping or principal component analysis).

Thus, for example if the method of the present invention is to be used for mapping a newly isolated gene(s) (or other DNA sequences), a single procedure may be employed to map the gene(s) to their chromosomal bands. Exemplified for two new genes, to this end 26 different probes may be prepared as follows: 24 chromosome paints and two loci specific probes (i.e., the newly isolated genes fluorescently labeled). The probes are then mixed and simultaneously hybridized preferably to mitotic chromosomes which are also DAPI counter stained. The result is a 24 (for a male, or 23 for a female) color karyotype, similar to the one presented in FIG. 9b, on which two loci specific signals (dots attributed to the loci specific probes) in yet two different colors point out the chromosome locations of the newly isolated genes which are then associated with a specific chromosomal band by generating an R-banded image as explained above.

In many cases, few loci specific probes are mapped to a single chromosomal band, yet which is distal and which is proximal is not established. Using the method of the present invention to simultaneously detect each of the few probes as each appears in a different RGB or artificial color, will, in many cases, enable to determine the relative arrangement of closely mapped sequences.

The SpectraCube™ system and the method of the present invention may also be used to detect interphase chromosome three dimensional arrangements. The reader is referred again to FIGS. 8a and 9a. On the upper right corner presented is a nucleus during interphase (marked NI) hybridized with the chromosome paints listed in Table 4 above. Examination of the color pattern of this nucleus reveals a unique feature. Note for example that both the chromosome 2 pair (in red) are located in the lower part of the nucleus and that the chromosome 6 pair (in purple) are both located in the opposite pole. Little is so far known about the chromosome organization during interphase, yet it is reasonable to suspect that changes occur in the chromosome organization during interphase in malignant cells. Thus, the method of the present invention may be of great value for early detection of various malignancies, defining the stage of a malignant disease, and hence better adjust a treatment to examined patients, etc. It should be noted that using the SpectraCube™ system combined with the method of the present invention and a three dimensional reconstruction means (e.g., a confocal microscope) may be used to extract three dimensional information of chromosome organization during interphase.

Many cancers and genetic disorders are characterized by chromosome deletions, translocations and other rearrangements and gross abnormalities (e.g., gene amplification). As demonstrated in Example 3 above, using the method of the present invention will enhance the ability to detect such abnormalities. Furthermore, it is clear that the method of the present invention is highly suitable for comparative genomic hybridization (CGH) and for reverse chromosome painting as described above.

One of the common chromosomal aberrations is associated with Down's-syndrome. It was long ago established that Down's syndrome is associated with trisomy of chromosome 21. More careful examination revealed that a specific region of chromosome 21 (21q22) is always associated (i.e., appears in trisomy) with this common syndrome. However, in some cases the karyotype of individuals affected with Down's syndrome is apparently normal as determined by conventional G- or R-banding karyotyping techniques. The widely accepted explanation to this phenomenon is that in these cases the trisomy is of a fragment derived from the 21q22 chromosome region which fragment is small and below the resolution of the conventional banding techniques. However, using the SpectraCube™ system combined with the method of the present invention will enable to detect these so far undetectable chromosome 21 trisomies in embryonic cells obtained for example via chorionic villi sampling and to enable a more educated genetic counseling to high risk women. It should be noted that chromosome 13 and chromosome 18 or fragments thereof were also reported to appear in trisomies resulting in birth of strikingly abnormal children and that the method of the present invention can be similarly applied for a prenatal diagnosis of these devastating chromosome 13 or 18 trisomies.

The method of the present invention, combined with the rapidly developing techniques of separating embryonic cells from peripheral blood of a pregnant woman will be of great value for low-risk prenatal karyotyping for the detection of chromosome 21 trisomies and other, less frequent chromosome abnormalities.

Using the SpectraCube™ system and the method of the present invention combined with chromosome telomeres specific probes, each of the telomeres (48 in human males, 46 in females) appears in a different color, will enable a comparative study of all telomeres in an examined species.

In the study of evolutionary related species and in the study of model systems (for example mouse as a model system for human) it is in many cases required to obtain comparative genome maps in which chromosomes of two or more species are aligned according to their sequence similarities and thus their chromosome-borne genetic information. Using the method of the present invention will facilitate obtaining such comparative maps. Consider for example the preparation of a human-mouse chromosome comparative map. For this purpose a complete set of chromosome paints of one of the species (e.g., human) are to be simultaneously hybridized with chromosome spreads of the other species (mouse in the given example) and analyzed as described above. The result is an image of the mouse karyotype painted with the human chromosome paints. Thus, an alignment can be made between the karyotypes of the two species.

Many other applications for FISH were so far described in the art's literature. One example is in the study of gene expression wherein by using loci specific probes hybridized with interphase nuclei obtained at intervals from a synchronized cell culture one can determine their order of replication (i.e., replicated genes appear as four dots and non-replicated genes appear as two dots), wherein, as a rule of thumb, early replicating genes are expressed in the examined cells and late replicating genes are not. The method of the present invention is highly suitable for this type of analysis since dozens of probes each having a slightly different spectrum can be analyzed simultaneously in a single hybridization followed by a single imaging step to detect them all. In fact the method of the present invention can be used for any FISH application so far described or yet to be described.

EXAMPLE 8

MULTICOLOR CHROMOSOME BANDING—CHROMOSOME BAR-CODING

Figure 20:
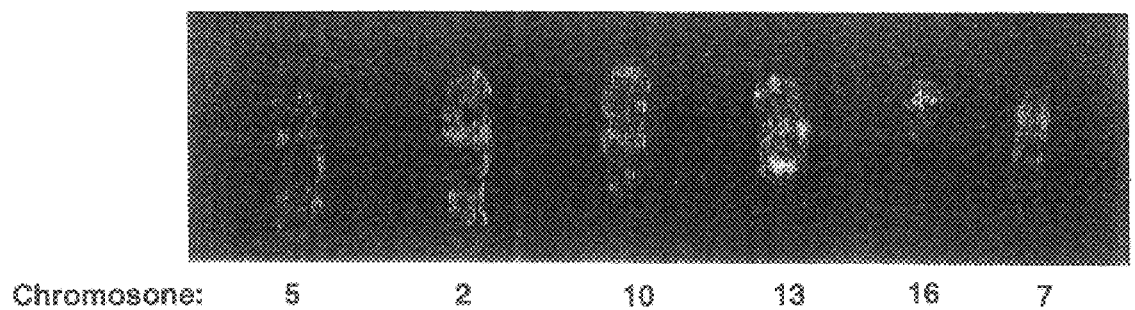
FIG. 20 present RGB images of few chromosomes with color bar-codes arranged along their longitudinal axes, as was obtained using the multicolor chromosome banding method of the present invention.
Figure 21:
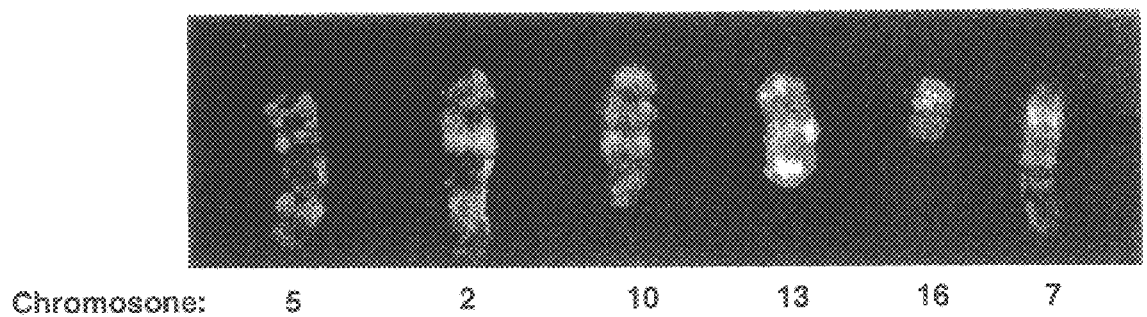
FIG. 21 is a color presentation of FIG. 20

With reference now to FIGS. 20 and 21, presented are RGB images of few chromosomes with color bar-codes arranged along their longitudinal axes, as was obtained using the SpectraCube™ system and the multicolor chromosome banding method of the present invention.

The bar codes shown in human chromosomes 5, 2, 10, 13, 16 and 7 were created using fluorescently labeled radiation hybrid chromosome fragments (for 5, 2, 10, 13 and 16) or YAC-clones (for 7) as a source for multi color chromosome fragments.

In all cases, two fluorophores having distinctly different colors, FITC (having a green fluorescence) and TRITC (tetramethylrhodamine-5-isothiocianate, having red fluorescence), were used to label the chromosome fragments according to the combinatorial hybridization approach.

For chromosomes 5, 2, 10, 13 and 16, the FITC and TRITC fluorophores were used to label two random fragment groups that were divided from a full set of radiation hybrid chromosome fragments (i.e., collectively covering the entire human genome). It will be appreciated that in such a case, the bar code which is created is random in nature and thus can not be predicted. Nevertheless, once the chromosome fragments source used for hybridization exists and measured, the same color bar-code (i.e., banding) pattern should follow for any other normal chromosomes hybridized with the same source of fragments and similarly measured.

The colors presented were picked using an RGB look-up-table that enhances the difference in the colors so that the bars with different colors are emphasized.

The color bar code along the short arm of chromosome 7 was created using six different YAC-clones previously mapped close to one another at known locations onto the short arm of human chromosome 7. These six YAC-clones were labeled with the above mentioned green and red fluorophores, in an alternating fashion according to their known chromosomal positions. The colors shown in the RGB image obtained were similarly chosen using a suitable RGB look-up-table for enhancing the result. Please note six different bars along the chromosome, each represents the hybridization of a different clone. As opposed to the above description concerning chromosomes 5, 2, 10, 13 and 16, in this case (i.e., chromosome 7), one can predict the banding pattern associated with the given chromosome, by selecting hybridization probes of known chromosomal origin.

This example can be extended using many YAC-clones covering all the chromosomes, and by using more fluorophore types, each characterized by a different fluorescence, to yield a complete multicolor banding karyotype of human or any other species.

The measurements were done using a fluorescent microscope supplemented with a custom design triple band filter from Chroma Technology (excitations: 455–485, 555–575, 630–650 nm, emissions: 500–550, 580–620, 660–740 nm) connected to the SpectraCube™ system, as described above. A Xenon light source was used for fluorophores excitation.

EXAMPLE 9

CHROMOSOME PAINTING AND/OR MULTICOLOR CHROMOSOME BANDING AND CONVENTIONAL CHROMOSOME BANDING

As mentioned, conventional chromosome banding (either G-banding or R-banding) is currently the main method used today in cytogenetics for various purposes such as for example detecting chromosome aberrations.

Conventional chromosome banding is actually the "cytogenetecists language", which is well known across the cytogenetic community.

One of the most important advantage of the method of the present invention is its ability to measure both conventional chromosome banding (e.g., R-banding using for example DAPI staining) and the spectral karyotyping (i.e., chromosome painting or multi color chromosome banding) of the same chromosome spreads.

The co-analysis of the two images thus obtained can lead to a classification of all the chromosomes together with the identification of both structural and numerical aberrations and can therefore assist cytogeneticists to acquire the new cytogenetic language associated with chromosome painting and multi color chromosome banding.

Figure 22A:
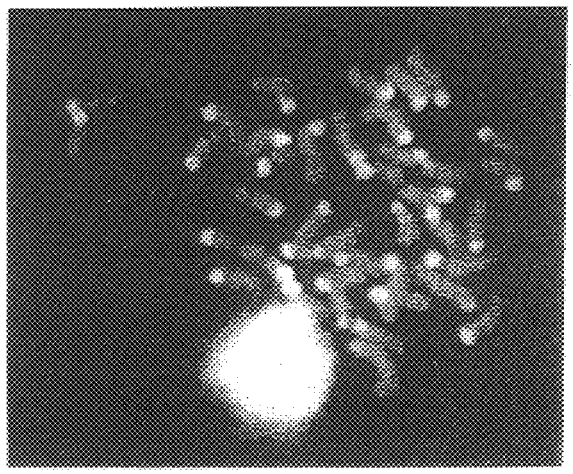
FIG. 22a, 22b and 22c are (a) a R-banding image using DAPI for chromosome staining, (b) a G-banding image obtained presenting the negative image of FIGS. 22a, and (c) a color karyotype RGB image using human chromosome paints of a single mouse chromosome spread, all obtained using the SpectraCube™ system.
Figure 22B:
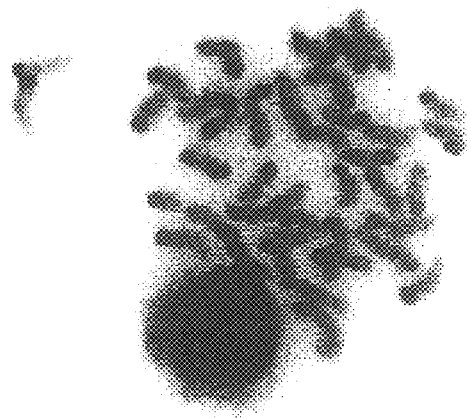
Figure 22C:
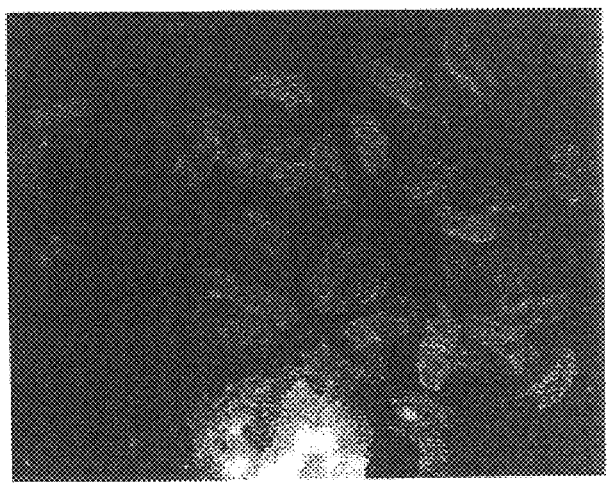
Figure 23A:
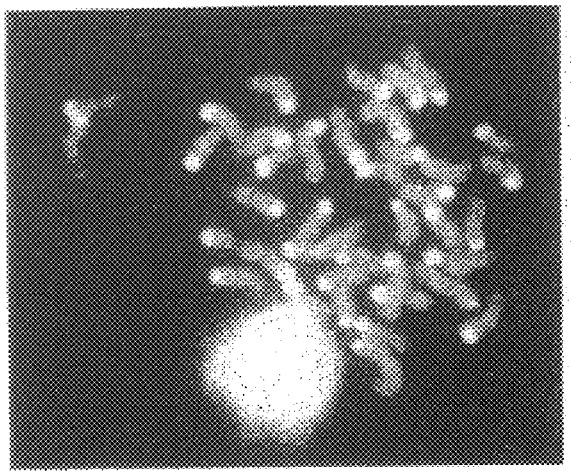
FIGS. 23a, 23b and 23c are original and color presentations of FIGS. 22a, 22b and 22c, respectively.

With reference now to FIGS. 22a–c and 23a–c, presented are a R-banding image (FIGS. 22a and 23a) using DAPI for chromosome staining, a G-banding image (FIGS. 22b and 23b) obtained presenting the negative image of FIGS. 22a and 23a, and a color karyotype RGB image (FIGS. 22c and 23c) of a single chromosome spread all obtained using the SpectraCube™ system.

Figure 23B:
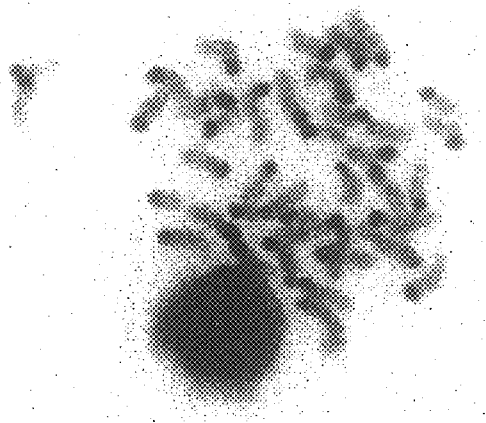

For G- or R-banding mouse chromosomes where stained with DAPI. For color karyotyping the DAPI stained chromosomes were thereafter hybridized with a complete set of human chromosome paints, as detailed under Tables 2 and 3 above. In order to achieve optimal spatial resolution, the objective used to acquire the DAPI images was x100 and the triple filter cube typically used for color karyotyping was replaced with a special DAPI band pass filter cube (excitation 350–400 nm, emission 400–450 nm). Such a filter cube is very common and exist for each microscope type and manufacturer. Then, by moving the scanner rapidly back and forth continually, the image was measured in an exposure time of about 5–15 seconds. The reason for moving the scanner as described was to eliminate fringes and to obtain clearer images. The relatively long exposure time is needed because usually the intensity of the DAPI dye is much less than that of the other fluorescent dyes. On the other hand DAPI is a stable fluorophore and does not bleach during time to the extent of other fluorophores such as ones used for color karyotyping. Obtained is a gray level image of DAPI R-banding (FIGS. 22a and 23a). In order to extract most of the information out of the DAPI R-banding image, the negative image was calculated, yielding the G-banding pattern which is more familiar to cytogeneticists (FIGS. 22b and 23b). This was done by using an invert function of the general form: $I'_{x,y}=N-I_{x,y}$, where N is the maximal dynamic range of the camera (in this case N=4,095), I is the positive intensity at each x,y location and I' is the calculated negative intensity at each x,y location. The result can be farther improved by enhancing the gray levels look-up-table.

Figure 23C:
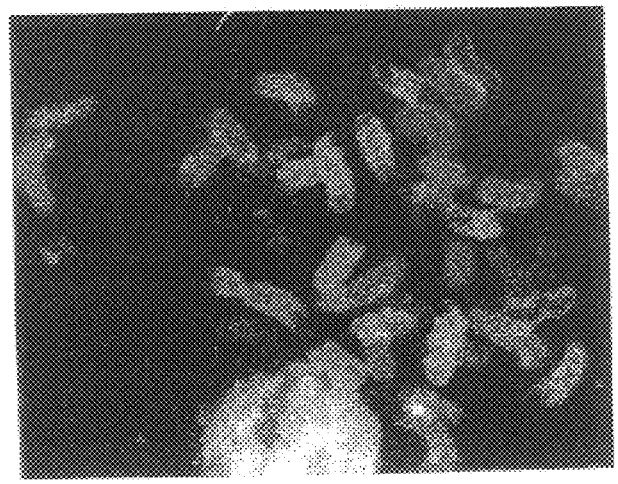

The color karyotype image of the same chromosome spread was also measured and is presented in FIGS. 22c and 23c. It can be clearly observed that the correlation of those images can lead to a high accuracy of chromosome identification. It will be appreciated that it is much harder to identify mouse chromosomes as compared with human chromosomes since they are more uniform in size and are less specifically banded using conventional chromosome banding techniques. As a result few scientists are capable of identifying mouse chromosomes. Nevertheless, using the color karyotyping and/or the multicolor banding method of the present invention, identifying the chromosomes becomes a simple task.

It will be further appreciated that using DAPI in combination with the fluorophores listed in Table 2 above is convenient since DAPI excitation and emission are characterized by wavelength in the blue range, whereas the other fluorophores are characterized by longer excitation and emission wavelengths. Thus, any other stain (i.e., conventional chromosome banding dye) having similar qualities may be employed for obtaining G- or R-banding of chromosomes as described above.

EXAMPLE 10

CHROMOSOME PAINTING AND/OR MULTICOLOR CHROMOSOME BANDING AND AUTOMATIC CHROMOSOME DETERMINATION

Once a given set of multi color probes is repeatedly used under identical conditions for either chromosome banding or chromosome painting as described hereinabove, a simple chromosomes classification algorithm attributing pixels having predetermined spectral characteristics to chromosomes can be used for automatic karyotyping. Extending this chromosome classification algorithm to also include a morphological algorithm, as well known in the art of automatic karyotyping, may achieve even better results.

Thus, reference hybridization results of normal chromosome spread are stored and used for spectral (and morphological) comparison with analyzed chromosome spreads, hybridized under otherwise identical conditions.

What is claimed is:

1. A method of hybridization based multicolor chromosome banding comprising the steps of:
   (a) providing a metaphase chromosome spread of a first species and chromosome paints of a second species, at least some of said chromosome paints being labeled with a different fluorophore or combination of fluorophores;
   (b) hybridizing said chromosome paints with said metaphase chromosome spread;
   (c) using a fluorescence microscope being optically coupled to a multiband collection device for collecting spectral data from said chromosome spread; and
   (d) based on said collected data calculating a color image in which pixels associated with each of said different fluorophores or combination of fluorophores are attributed distinctive colors, thereby a banded color image of said metaphase chromosome spread is obtainable;
   wherein said method is for an application selected from the group consisting of providing a color banding karyotype of embryonic cells, providing a color banding karotype of white blood cells, providing a color banding karyotype of malignant cells, providing a color banding karyotype of cells examined for malignancy, detecting the stage of a malignancy, following the efficiency of an anti-cancer treatment and detecting chromosomal aberrations following exposure to mitogenic agents.

2. A method as in claim 1, where in said fluorescence microscope is supplemented with a filter selected from the group consisting of a double band dichroic filter and a triple band dichroic filter.

3. A method as in claim 1, wherein said chromosome paints are labeled using a strategy selected from the group consisting of combinatorial labeling and combinatorial hybridization.

4. A method as in claim 1, wherein said chromosome paints are labeled by interspersed repetitive sequence—PCR.

5. A method as in claim 1, wherein said fluorophores are conjugated to a nucleotide or a nucleotide analog.

6. A method as in claim 1, wherein said first and second species are each independently selected from the group consisting of, human, mouse and monkey.

7. A method as in claim 1, wherein said embryonic cells are selected from the group consisting of chorionic villi cells and embryonic cells isolated from the peripheral blood of a pregnant woman.

8. A method as in claim 7, wherein said method is for detecting a trisomy of a genetic material selected from the group consisting of human chromosome 21, human chromosomal band 21q22, a fragment of human chromosomal band 21q22, human chromosome 18, a fragment of human chromosome 18, human chromosome 13 and a fragment of human chromosome 13.

9. A method as in claim 7, wherein said providing said color banding karyotype of said cells examined for malignancy, is for obtaining a color translocation map.

10. A method as in claim 1, wherein said detection of the stage of said malignancy is for selecting a treatment for said malignancy.

11. A method as in claim 1, wherein said metaphase chromosome spread is stained with a conventional chromosome banding dye, the method further comprising the step of obtaining a gray level banding image of said chromosomes.

12. A method as in claim 11, wherein said conventional chromosome banding dye is DAPI.

13. A method as in claim 1, wherein said multiband collection device is an imaging spectrometer.

* * * * *